(12) United States Patent
Ehrlich et al.

(10) Patent No.: US 8,936,762 B2
(45) Date of Patent: Jan. 20, 2015

(54) HIGH THROUGHPUT MULTICHANNEL READER AND USES THEREOF

(75) Inventors: Daniel J. Ehrlich, Somerville, MA (US); Brian McKenna, Scituate, MA (US)

(73) Assignee: Trustees of Boston University, Boston, MA (US)

(*) Notice: Subject to any disclaimer, the term of this patent is extended or adjusted under 35 U.S.C. 154(b) by 244 days.

(21) Appl. No.: 13/393,688

(22) PCT Filed: Sep. 1, 2010

(86) PCT No.: PCT/US2010/047552
§ 371 (c)(1),
(2), (4) Date: May 15, 2012

(87) PCT Pub. No.: WO2011/028818
PCT Pub. Date: Mar. 10, 2011

(65) Prior Publication Data
US 2012/0220022 A1    Aug. 30, 2012

Related U.S. Application Data

(60) Provisional application No. 61/238,894, filed on Sep. 1, 2009.

(51) Int. Cl.
*G01N 15/06* (2006.01)
*G01N 33/00* (2006.01)
(Continued)

(52) U.S. Cl.
CPC ........................ *G01N 15/14* (2013.01)
USPC .......... 422/400; 422/68.1; 422/502; 422/503; 422/509; 436/43; 436/174; 436/180; 436/164; 436/172

(58) Field of Classification Search
CPC .............. G01N 15/14; G01N 15/1425; G01N 15/1434; G01N 15/1463; G01N 15/147; G01N 15/1475; G01N 15/1484; B01L 3/5027; B01L 3/502707; B01L 3/502715; B01L 3/502776

USPC .......... 422/68.1, 502, 503, 509; 436/43, 174, 436/180, 164, 172
See application file for complete search history.

(56) References Cited

U.S. PATENT DOCUMENTS 6,620,591 B1    9/2003    Dunlay et al.
7,157,274 B2    1/2007    Bohm et al.
(Continued)

OTHER PUBLICATIONS

Aborn et al., Lab Chip, 5:669-674 (2005). "A 768-lane microfabricated system for high-throughput DNA sequencing."
(Continued)

*Primary Examiner* — Brian J Sines
(74) *Attorney, Agent, or Firm* — Nixon Peabody, LLP; Ronald I. Eisenstein

(57) ABSTRACT

The present invention relates generally to the field of high content screening of particles, e.g., cells in a flow cytometric system. In particular, the present invention relates to devices, methods and systems to obtain line-scan images of particles, e.g., cells, of a plurality of different samples simultaneously, where the line-scan images can be used to identify cells based on at least one of a variety of phenotypic characteristics such as shape, asymmetry, and intracellular information for cell sorting and selection. In some embodiments, the line-scan images are obtained as the particles, e.g., cells, in a plurality of different samples flow through a plurality of microchannels, reducing the need and time for focusing of the image detection system. In some embodiments, the laser spot size has a small spatial resolution for rapid capturing of images of cells. In some embodiments, the laser spot size has a larger spatial resolution for imaging of larger particles or cells, e.g., rare cells in a sample. In some embodiments, the devices, methods and systems are automated for a high-throughput, high content screening of particles such as cells in a plurality of samples.

28 Claims, 34 Drawing Sheets

(51) Int. Cl.
  G01N 33/48 (2006.01)
  G01N 15/14 (2006.01)

(56) References Cited

U.S. PATENT DOCUMENTS

| | | | |
|---|---|---|---|
| 2002/0123033 A1 | 9/2002 | Eyal et al. | |
| 2003/0032035 A1 | 2/2003 | Chatelain et al. | |
| 2003/0124516 A1 | 7/2003 | Chung et al. | |
| 2007/0154895 A1 | 7/2007 | Spaid et al. | |
| 2008/0070311 A1 | 3/2008 | Li | |
| 2009/0051912 A1 | 2/2009 | Salazar et al. | |
| 2009/0093001 A1 | 4/2009 | Hill et al. | |
| 2009/0185182 A1 | 7/2009 | Kim et al. | |
| 2009/0201504 A1 | 8/2009 | Ho et al. | |

OTHER PUBLICATIONS

Abramoff et al., Nuclear texture: Biophotonics Intern. 11:36-42 (2004). "Image Processing with ImageJ."
Bleicher et al., Nature Reviews Drug Discovery, 2:369-378 (2003). "Hit and Lead Generation: Beyond High Throughput Screening."
Boufounos et al., Hidden Markov models for DNA sequencing (poster presentation). Proceedings of the Workshop on Genomic Signal Processing and Statistics (GENSIPS), Oct. 12-13, 2002, Raleigh, NC (2002).
Boufounos et al., Journal of the Franklin Institute, 341:23-36 (2004). "Basecalling using hidden Markov models."
Bullen, Nature Reviews Drug Discovery, 7:54-67 (2008). "Microscopic imaging techniques for drug discovery."
Callewaert et al., Electrophoresis, 25:3128-3131 (2004). "Total serum protein N-glycome profiling on a capillary electrophoresis-microfluidics platform."
Carpenter et al., Nature Reviews Genetics, 5:11-22 (2004). "Systematic Genome-Wide Screens of Gene Function."
Carpenter et al., Genome Biology, 7:R 100 (2006). "CellProfiler: image analysis software for identifying and quantifying cell phenotypes."
Ding et al., The Journal of Biological Chemistry, 273(44):28897-28905 (1998). "Characterization and Quantitation of NF-kappaB Nuclear Translocation Induced by Interleukin-1 and Tumor Necrosis Factor-alpha."
Eggert et al., Current Opinion in Chemical Biology, 10:232-237 (2006). "Small molecule screening by imaging."
Ehrlich et al., Nanotechnology, 17:315-319 (1999). "Microfluidic devices for DNA analysis."
Ehrlich et al. Proc. Micro Total Analysis Systems, pp. 16-18 2001 (microTAS 2001), Monterey, CA 2001. "BioMEMS-768 DNA Sequencer."
Ehrlich et al., Proceedings of First IEEE International Conference on Sensors, Jun. 12-14, 2002, Orlando, Florida. IEEE 1:448-449 (2002). "MEMS-Based System for DNA Sequencing and Forensics."
Ehrlich et al., 9th International Conference on Miniaturized Systems for Chemistry and Life Sciences, Oct. 9-13, 2005, Boston, Massachusetts (2005). "Status of Genome-Center DNA Sequencing Technology MEMS."
El-Difrawy et al., Proceedings of the Thirty-Seventh Asilomar Conference on Signals, Systems and Computers, Nov. 9-12, 2003, Pacific Grove, California. IEEE 2:2088-2092 (2003). "A Numerical Optimization Approach for Color Correction in Forensic DNA Genotyping."
El-Difrawy et al., Proceedings of the 30th Annual Northeast Bioengineering Conference, Apr. 17-18, 2004, Springfield, Massachusetts. IEEE 112-113 (2004). "Uniform Acquisition for High-Throughput DNA Sequencing."
El-Difrawy et al., Rev. Sci. Instrum., 76:074301 (2005). "High throughput system for DNA sequencing."
El-Difrawy et al., Electrophoresis, 27:3779-3787 (2006). "Numerical model for DNA loading microdevices: Stacking and autogating effects."

Emmelkamp et al., Electrophoresis, 25:3740-3745 (2004). "The potential of autofluorescence for the detection of single living cells for label-free cell sorting in microfluidic systems."
Fatoyinbo et al., Electrophoresis, 29:3-10 (2008). "Rapid-on-chip determination of dielectric properties of biological cells using imaging techniques in a dielectrophoresis dot microsystem."
Fu et al., Nature Biotechnology, 17:1109-1111 (1999). "A microfabricated fluorescence-activated cell sorter."
George et al., Journal of Immunological Methods, 311:117-129 (2006). "Quantitative measurement of nuclear translocation events using similarity analysis of multispectral cellular images obtained in flow."
Goedecke et al., Electrophoresis, 25:1678-1686 (2004). "A high-performance multilane microdevice system designed for the DNA forensics laboratory."
Goedecke et al., 9th International Conference on Miniaturized Systems for Chemistry and Life Sciences, Oct. 9-13, 2005, Boston, Massachusetts, 1361-1363 (2005). "Quantification of Simple Tandem Repeat Profiles for DNA Forensics."
Goedecke et al., Journal of Chromatography A, 1111:206-213 (2006). "Microdevice DNA forensics by the simple tandem repeat method."
Gomez-Sjoberg et al., Anal. Chem., 79:8557-8563 (2007). "Versatile, Fully Automated, Microfluidic Cell Culture System."
Greenwald et al., Blood, 103:1475-1484 (2004). "Eµ-BRD2 transgenic mice develop B-cell lymphoma and leukemia."
Haney et al., Drug Discovery Today, 11(19/20):889-894 (2006). "High-content screening moves to the front of the line."
Huh et al., Physiol. Meas., 26:R73-R98 (2005). "Microfluidics for flow cytometric analysis of cells and particles."
Salas-Solano et al., Anal. Chem., 72:3129-3137 (2000). "Optimization of High-Performance DNA Sequencing on Short Microfabricated Electrophoretic Devices."
Koutny et al., Proceedings from the Ninth International Symposium on Human Identification, Oct. 8-10, 1998, Orlando, Florida. Promega (1998). "High Speed STR Analysis on Mlcrofabricated Electrophoretic Devices."
Koutny et al., Anal. Chem., 72:3388-3391 (2000). "Eight Hundred-Base Sequencing in a Microfabricated Electrophoretic Device."
Krishnan et al., Nature, 435:765-772 (2005). "Structural insights into a yeast prion illuminate nucleation and strain diversity."
Lang et al., Nature Reviews Drug Discovery, 5:343-356 (2006). "Cellular imaging in drug discovery."
Lee et al., Methods in Enzymology, 414:468-486 (2006). "High-Content Screening: Emerging Hardware and Software Technologies."
Li et al., Anal. Chem., 69:1564-1568 (1997). "Transport, Manipulation, and Reaction of Biological Cells On-Chip Using Electrokinetic Effects."
Pouton et al., Nature Reviews Drug Discovery, 6:605-616 (2007). "Embryonic stem cells as a source of models for drug discovery."
Lin et al., Biomicrofluidics, 3:014101 (2009). "Vertical hydrodynamic focusing in glass microchannels."
Lindblad et al., Cytometry Part A, 57A:22-33 (2004). "Image Analysis for Automatic Segmentation of Cytoplasms and Classification of Rac1 Activation."
Loo et al., Nature Methods, 4(5):445-453 (2007). "Image-based multivariate profiling of drug responses from single cells."
Liu et al., Proceedings of the Workshop on Genomic Signal Processing and SStatistics (GENSIPS), May 26-27, Baltimore, Maryland (2004). "Sizing Standard Identification in Forensic DNA Genotyping."
McKenna et al., Lab Chip, 9:305-310 (2009). "384-Channel parallel microfluidic cytometer for rare-cell screening."
McKenna et al., Nature Methods, 8(5):401-403 (2011). "A parallel microfluidic flow cytometer for high-content screening."
Mitnik et al., Electrophoresis, 23:719-726 (2002). "High-speed analysis of multiplexed short tandem repeats with an electrophoretic microdevice."
Pepperkok et al., Nature, 7:690-696 (2006). "High-throughput fluorescence microscopy for systems biology."

(56) References Cited

OTHER PUBLICATIONS

Perroud et al., Anal. Chem., 80:6365-6372 (2008). "Microfluidic-Based Cell Sorting of *Francisella tularensis* Infected Macrophages Using Optical Forces."

Schmalzing et al., Proc. Natl. Acad. Sci., 94:10273-10278 (1997). "DNA typing in thirty-seconds with a microfabricated device."
Schmalzing et al., Anal. Chem., 70:2303-2310 (1998). "DNA Sequencing on MicroFabricated Electrophoretic Devices."
Schmalzing et al., Analytical Biochemistry, 270:148-152 (1999). "Two-Color Multiplexed Analysis of Eight Short Tandem Repeat Loci with an Electrophoretic Microdevice."
Schmalzing et al., Genome Res., 9:853-858 (1999). "Toward Real-World Sequencing by Microdevice Electrophoresis."
Schmalzing et al., Electrophoresis, 20:3066-3077 (1999). "Recent developments in DNA sequencing by capillary and microdevice electrophoresis."
Schmalzing et al., Nucleic Acids Research, 28(9):e43 (2000). "Microchip electrophoresis: a method for high-speed SNP detection."
Schalmzing et al., Integrated Microfabricated Biodevices: Advanced Technologies for Genomics, Drug Discovery, Bioanalysis and Clinical Diagnostics, New York: Marcel Dekker, pp. 55-70 (2002). "Short Tandem Repeat Analysis on Microfabriated Electrophoretic Devices."
Segre et al., Fluid Mech., 14:136-157 (1962). "Behaviour of macroscopic rigid spheres in Poiseuille flow. Part 2. Experimental results and interpretation."
Selim et al., Proceedings of the 27th Annual Meeting of the American Society for Bone and Mineral Research, Sep. 23-27, 2005, Nashville, Tennessee. J Bone Miner Res 20 (suppl 1):S183 (2005). "Development of a Novel Cell Scanning System (Cell Track) for Expression Cloning of the Carboxyl-Terminal Parathyroid Hormone Receptor."
Shorter et al., Nature Reviews Genetics, 6:435-450 (2005). "Prions as Adaptive Conduits of Memory and Inheritance."
Srivastava et al., Electrophoresis, 26:1130-1143 (2005). "Numerical simulation of DNA sample preconcentration in microdevice electrophoresis."
Thorsen et al., Science, 598:580-584 (2002). "Microfluidic Large-Scale Integration."
Ueberfeld et al., Anal. Chem., 78:3632-3637 (2006). "Solid-Support Sample Loading for DNA Sequencing."
Ueberfeld et al., Anal. Chem., 80(19):7430-7436 (2008). "Reaction-Mapped Quantitative Multiplexed Polymerase Chain Reaction on a Microfluidic Device."
Ueberfeld et al., Electrophoresis, 30:2090-2099 (2009). "Scaling of nucleic acid assays on microelectrophoresis array devices: High-dynamic range multi-gene readout from less than ten transcripts."
Vazquez et al., Anal. Chem., 73:3035-3044 (2001). "Shear-Induced Degradation of Linear Polyacrylamide Solutions during Pre-Electrophoretic Loading."
Vazquez et al., Journal of Chromatorgraphy B, 779:163-171 (2002). "Electrophoresis using ultra-high voltages."
Vazquez et al., Anal. Chem., 74:1952-1961 (2002). "Electrophoretic Injection within Microdevices."
Wada et al., Journal of Lightwave Technology, 17(10):1758-1765 (1999). "A 10 Gb/s Optical Code Division Multiplexing Using 8-Chip Optical Bipolar Code and Coherent Detection."
Wheeler et al., Nature Genetics Supplement, 37:S25-S30 (2005). "Cell microarrays and RNA interference chip away at gene function."
http://www.cellomics.com/products/high-content-informatics/cellinsight-personal-image-cytometer.html, accessed Jul. 24, 2012. "Cell Insight Personal Image Cytometer."
http://www.shimadzu-biotech.jp/products/denova/index.html accessed Jul. 24, 2012. "Gas Chromatography: Shimadzu (Shimadzu Corporation)."
Gough et al., Methods of Microbiology, 356; 41-61 (2006). "Requirements, Features, and Performance of High Content Screening Platforms."
Schmalzing et al., Methods in Molecular Biology, 2001, 163: Capillary Electrophoresis of Nucleic Acids, 2: Practical Applications of Capillary Electrophoresis, ed. K. R. Mitchelson and J. Cheng, Humana Press Inc., Totowa N.J. pp. 163-173. "Genotyping by Microdevice Electrophoresis."
Yang et al., Poster Presentation at Lehigh University Center for Optical Technologies, 2005, "Optical Diagnostics for use in Microfluidic Devices," Penn State BioMemS@PSU.
Product Brochure from Amnis.com "Cytometry Without Limits—The ImageStreamX Mark II Imaging Flow Cytometer" (2002) (available from https://www.amnis.com/documents/brochures/ISX-MKII%20Brochure_Final_Web.pdf).

FIG. 1A
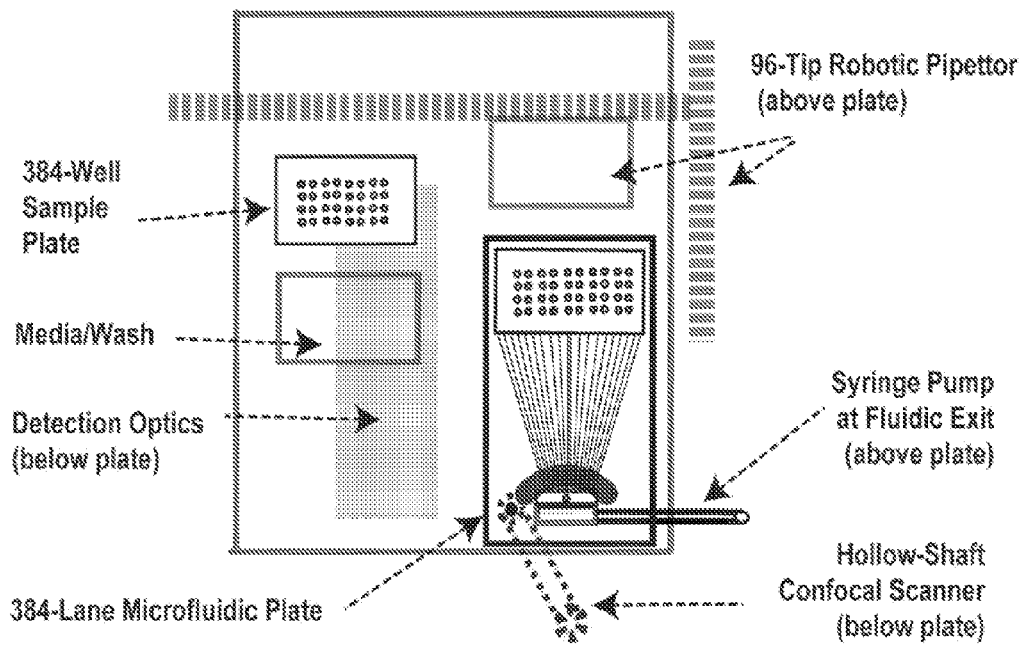
FIG. 1B
FIG. 1C
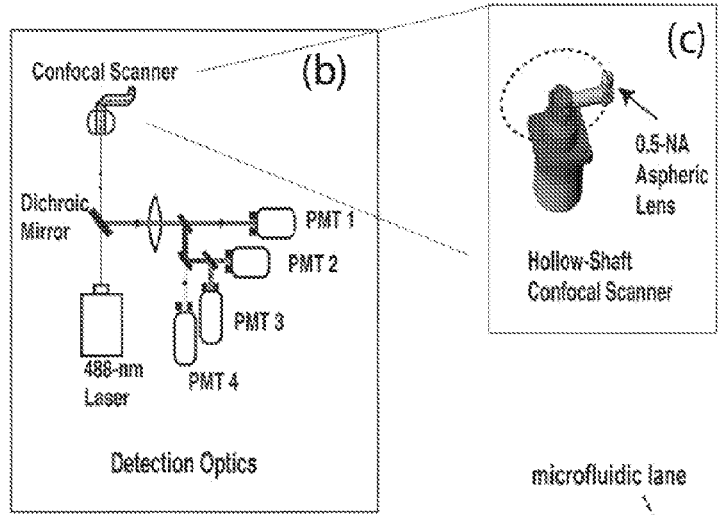
FIG. 1D FIG. 1E FIG. 1F
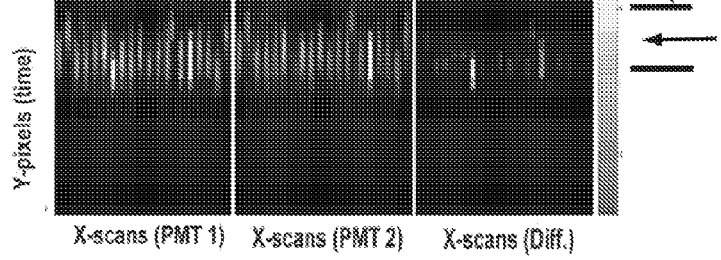

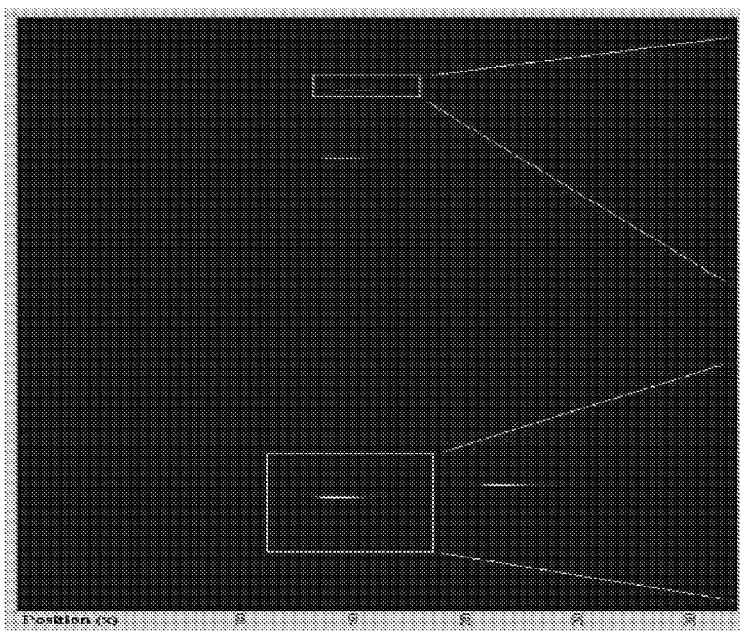
FIG. 3A
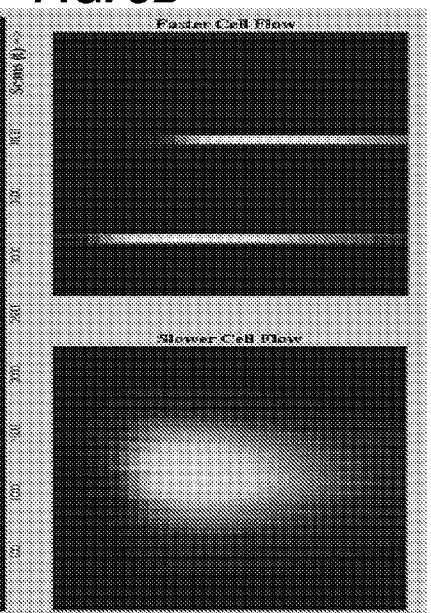
FIG. 3B
FIG. 3C

FIG. 4A
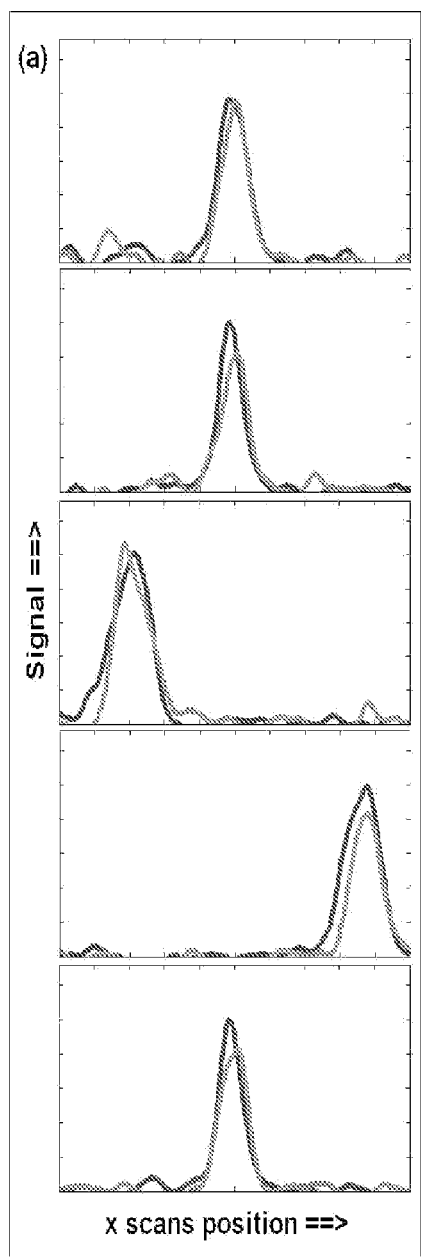
FIG. 4B
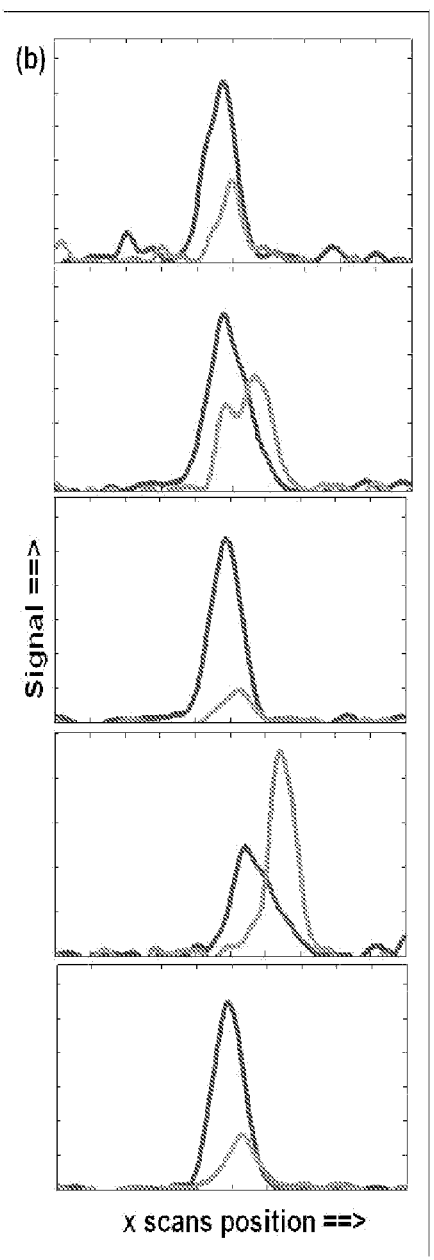
FIG. 4C    Neg Sample
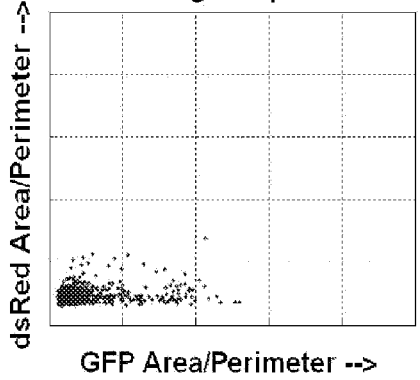
FIG. 4D    Pos Sample
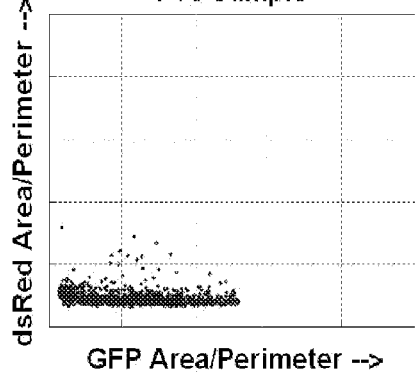

FIG. 24A
Lane 2
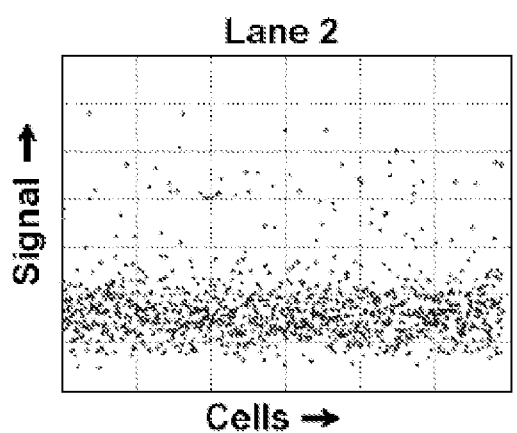
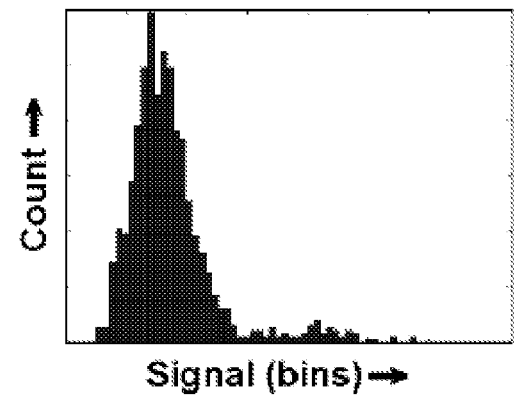
FIG. 24B
Lane 14
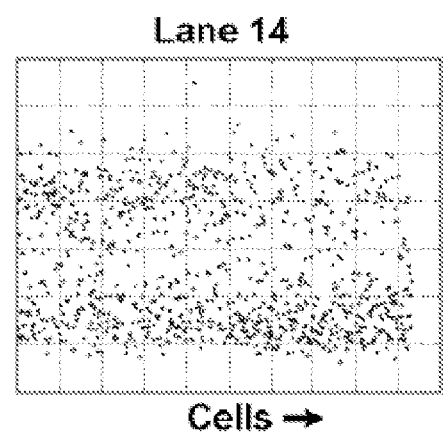
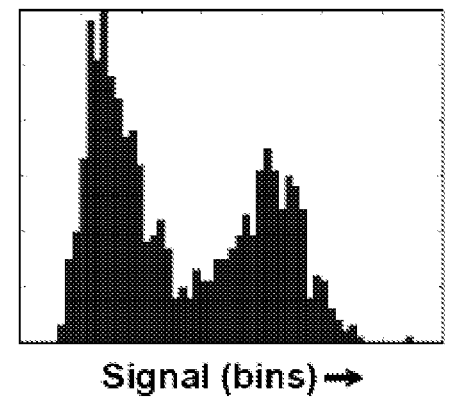

FIG. 25A
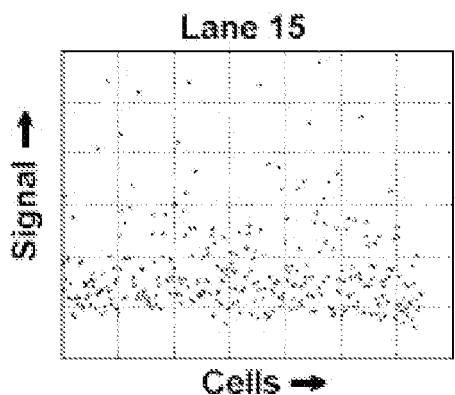
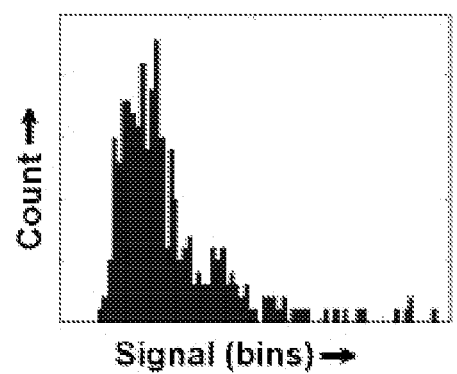
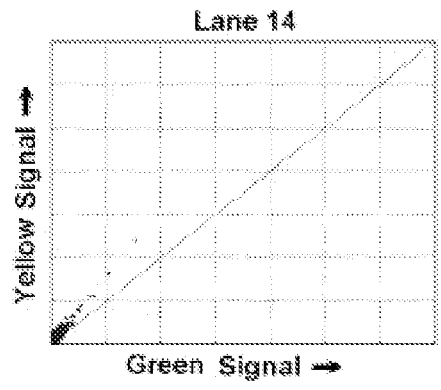
FIG. 25B
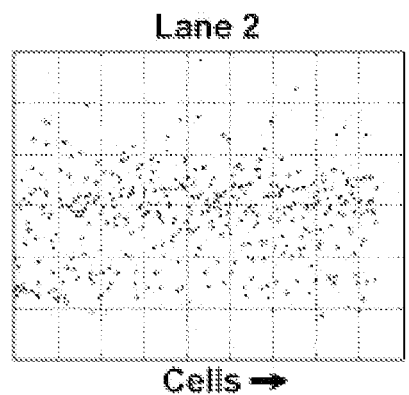
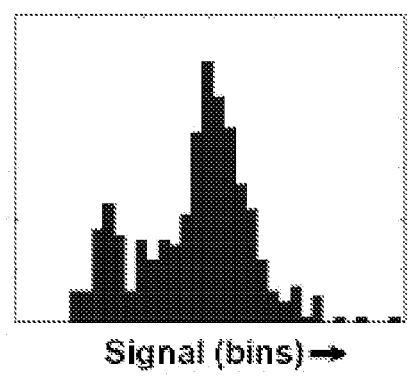
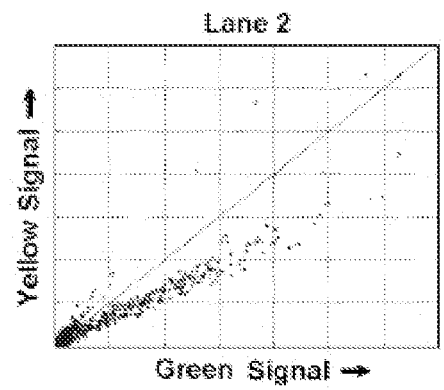

*FIG. 28A*     *FIG. 28B*
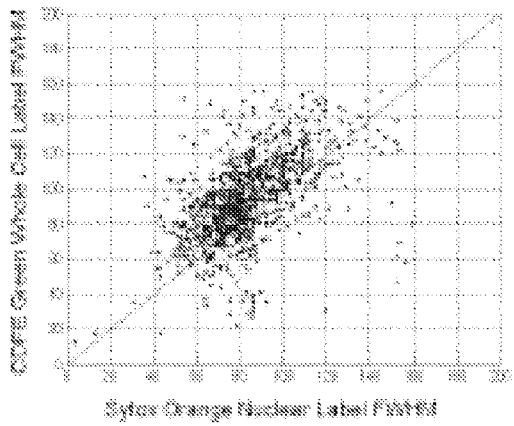 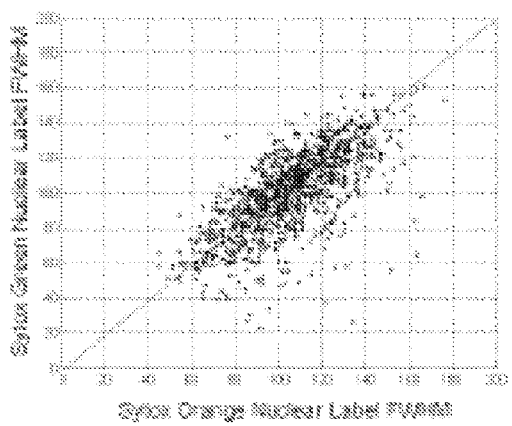
CDFE Green  
Whole Cell Label
Sytox Green  
Nuclear Label
*FIG. 29A*  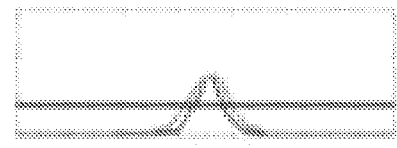  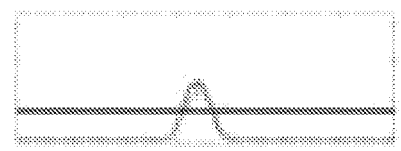
*FIG. 29B*  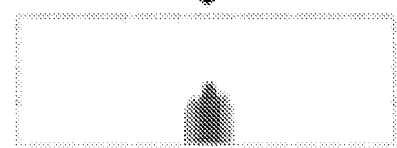  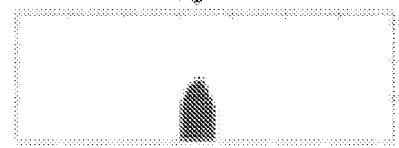

FIG. 36A
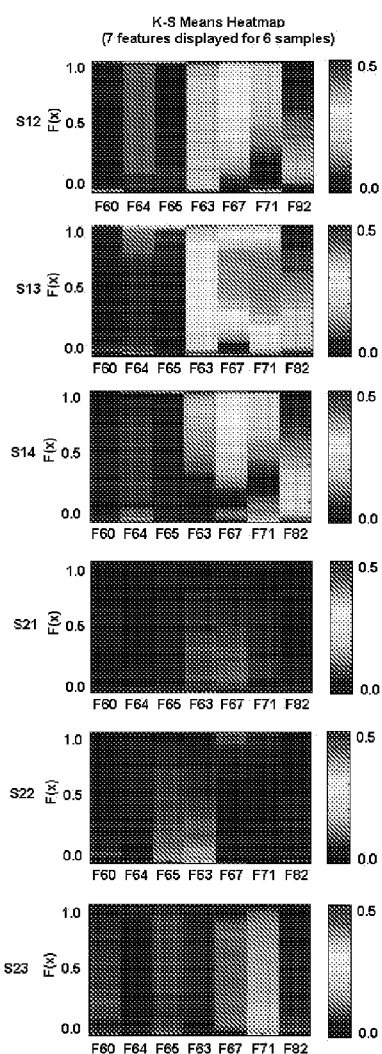
FIG. 36B
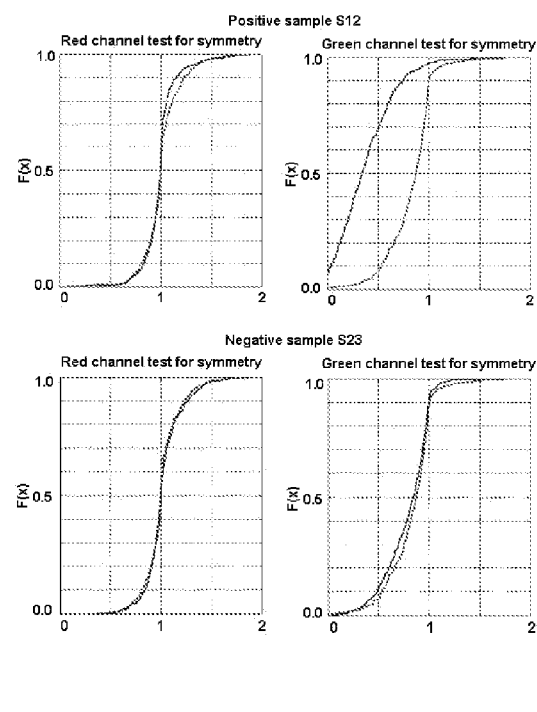
FIG. 36C

HIGH THROUGHPUT MULTICHANNEL READER AND USES THEREOF

CROSS REFERENCE TO RELATED APPLICATION

This application is a 35 U.S.C. §371 National Phase Entry Application of International Application No. PCT/US2010/047552 filed Sep. 1, 2010, which designates the U.S., and which claims benefit under 35 U.S.C. §119(e) of the U.S. provisional application No. 61/238,894 filed Sep. 1, 2009, the contents of which is incorporated herein in its entirety by reference.

GOVERNMENT SUPPORT

This invention was made with Government support under Grant No: HG001389 awarded by the National Institutes of Health. The Government has certain rights in the invention.

FIELD OF THE INVENTION

Embodiments of the invention are generally related to high content screening (HCS) in the field of flow cytometry. More particularly, embodiments of the invention are directed to coupling high content screening by flow cytometry with in line scan imaging in a parallel flow instrument for protein localization, and applications thereof, for a more efficient, less costly improved high content screening methodology over traditional high content screening systems, such as bio-molecular assays and cell-based imaging assays.

BACKGROUND OF THE INVENTION

Relatively narrow sets of methods define eras like genomics and proteomics. The instruments used to practice these methods are often badly mismatched to the biological agenda. A bottleneck now exists as biology moves to the biological cell, and genomic and proteomic approaches have increased the encyclopedia of molecules and interactions to the point where one can practice broad combinatorial experiments in cells. The primary tools for read-out of these experiments include microscopy, cytometry, arrays, fluorimeters and a handful of biochemical assays.

Because it can quickly produce a statistically significant reading, one of the most important of these tools is the fluorescence-activated flow cytometer (FACS). However in several dimensions FACS is inadequate to the agenda. It is only practical to make measurements on a few variables (typically 2 or 3 variables) at a time and thus compromises sample throughput. In addition FACS does not provide valuable intracellular information. In contrast, high-content screening (HCS, i.e., Imaging cytometry or high-throughput automated microscopy) (Taylor, D. L., et al. Humana Press, Totowa N. J. 2007; Bullen A., *Nature Reviews* 7, 54-93, 2008; Haney, S. A., et al., *Drug Discovery Today,* 11, 889-894, 2008; Gough, A. H. and Johnston, P. A., *Methods Mol. Biol.* 356, 41-51, 2007; Lee, S., and Howel, B. J., *Methods Enzymol.* 414, 468-483, 2006; Pepperkok, R. and Ellenberg, *J. Nat. Rev. Cell Biol.* 7, 690-696, 2006; Eggert, U. S. and Mitchinson, T. J., *Curr. Opin. Chem. Biol.* 10, 232-237, 2006; Loo, L. H., et al., *Nature Methods* 4, 445-453, 2007; Proceedings of the Symposium on High-Content Analysis, San Fransisco, Calif., Jan. 5-9, 2009; Bleicher, K. H., et al., *Nature Rev.* 2, 369, 2003; Lang, P. et al., *Nature Rev.* 5, 343-356, 2006; Ding, G. J. F., et al. *J. Bio. Chem.* 273., 28897, 1998; George, T. C., et al., *J Immuno. Methods* 311, 117-129, 2006; Lindblad, J., et al., *Cytometry* A, 57, 22-23, 2004; Nuclear texture: Abramoff, M. D., Magalhaes, P. J., and Dam, S. J. Biophotonics Intern. 11, 36-42 2004; Carpenter A. E., et al. *Genome Biology,* 7:R100, 2006; Carpenter, A. E., et al., *Nat. Rev. Genet.* 5, 11-22, 2004; Wheeler, D. B., et al., *Nature Genetics,* 37, s25-s30, 2005) is an attempt to add more information to the content of FACS, but high content screening (HCS) methods struggle to achieve a useful assay speed (Eggert, U. S. and Mitchinson, T. J., *Curr. Opin. Chem. Biol.* 10, 232-237, 2006; Loo, L. H., et al., *Nature Methods* 4, 445-453, 2007; Proceedings of the Symposium on High-Content Analysis, San Fransisco, Calif., Jan. 5-9, 2009; Bleicher, K. H., et al., *Nature Rev.* 2, 369, 2003; Lang, P. et al., *Nature Rev.* 5, 343-356, 2006). Throughput of both FACS and HCS is an issue for readout of combinatorial biology in general, but particularly with live cells. For example, nuclear translocation kinetics, the basis of the most successful high content screening (HCS) assay, often have a half-time response of 5-10 minutes (Ding, G. J. F., et al. *J. Bio. Chem.* 273., 28897, 1998). In a live-cell kinetic study it is usually not possible to read a single 96-well HCS plate in this time. Furthermore, for either flow cytometry or HCS, fixing cells causes protein reorganization, and many cytokine modifiers can show alternatively agonism or antagonism in a dose-dependant fashion. Therefore, the biology of nuclear translocation calls out for dose-response curves taken over many dose levels, on live cells, and with time response on the order of several minutes. Except when a very limited number of compounds are to be tested, the first HCS methods remain orders of magnitude mismatched in speed for real needs of combinatorial drug discovery.

Furthermore the first HCS methods still do not monitor cells at a sufficient level of multi-parameter complexity. Even in the most controlled conditions biological samples are highly heterogeneous at the cellular level. There is a need for a whole new class of tools that are capable of gathering many more simultaneous parameters (specifically multiplex expression analysis) from well-defined subpopulations of cells. The multi-parameter complexity of early HCS is inadequate, particularly for studies with primary cells (e.g., cancer). Unfortunately HCS readout tools do not permit sorting by phenotype.

FACS has speed but is information poor and it does not multiplex well. HCS increases information content to a degree, but does not increase content sufficiently, is too slow, and does not separate (sort) cells, so it does not permit deeper post-cytometry analysis.

High-Content Screening in General: Several of the most common high-content assays implemented on microscopes (2-D) are (Taylor, D. L., et al. Humana Press, Totowa N. J. 2007; Bullen A., *Nature Reviews* 7, 54-93, 2008; Haney, S. A., et al., *Drug Discovery Today,* 11, 889-894, 2008; Gough, A. H. and Johnston, P. A., *Methods Mol. Biol.* 356, 41-51, 2007; Lee, S., and Howel, B. J., *Methods Enzymol.* 414, 468-483, 2006; Pepperkok, R. and Ellenberg, *J. Nat. Rev. Cell Biol.* 7, 690-696, 2006; Eggert, U. S. and Mitchinson, T. J., *Curr. Opin. Chem. Biol.* 10, 232-237, 2006; Loo, L. H., et al., *Nature Methods* 4, 445-453, 2007; Proceedings of the Symposium on High-Content Analysis, San Fransisco, Calif., Jan. 5-9, 2009; Bleicher, K. H., et al., *Nature Rev.* 2, 369, 2003; Lang, P. et al., *Nature Rev.* 5, 343-356, 2006; Ding, G. J. F., et al. *J. Bio. Chem.* 273., 28897, 1998; George, T. C., et al., *J Immuno. Methods* 311, 117-129, 2006; Lindblad, J., et al., *Cytometry* A, 57, 22-23, 2004; Nuclear texture: Abramoff, M. D., Magalhaes, P. J., and Dam, S. J. Biophotonics Intern. 11, 36-42 2004; Carpenter A. E., et al. *Genome Biology,* 7:R100, 2006; Carpenter, A. E., et al., *Nat. Rev. Genet.* 5, 11-22, 2004; Wheeler, D. B., et al., *Nature Genetics,* 37, s25-s30, 2005) (a)

nuclear translocation (NT). The most common NT assay is NF-kB translocation. NF-kB is a transcription factor that is critical to cellular stress response. The p65 subunit is a sensitive to several known stimulants, for example, by altered interleukin ILa1 or tumor necrosis factor. The translocation to the nucleus is required to induce gene expression. (b) apoptosis. Image-based assays for apoptosis can provide more information than FACS. For example, by determining nucleus size, it is possible to ascertain necrotic or late apoptotic cells. The nucleus is stained and the image algorithm determines shape and size relative to the cell dimensions. (c) target activation. A very wide class of assays measure localization and total intensity from GFP fusions or other fluorescent markers. Cell cycle, receptor internalization, or drug resistance are commonly measured. (d) co-localization of markers. Co-localization is highly informative about biological mechanism. This is an enormous area of active research particularly in the field of biological development and imaging information is highly useful. (e) intracellular trafficking. Several microscope-based assays track the intracellular migration of molecules by programmed endocytosis. For example, Amnis Inc. has introduced an assay where the antibody CD20 is monitored and correlated with markers for endosomes and lysosomes. (f) morphology. The most obvious markers for phenotype are cell shape and area, however more subtle rearrangements of the cytoskeleton and location of organelles are also often used in microscope assays. (g) cell cycle. The progression of cell cycle is widely used in screening cancer therapies. The phase of individual cells is correlated with markers for specific proteins. Measurements are often also made on the dimensions or total DNA of the nucleus.

High-Content Screening Instruments: Several commercial 2-D HCS instruments are: (i)—CCD/automated microscopes (e.g., Thermo Scientific—Cellomics ArrayScan™, GE Healthcare—in Cell™ PerkinElmer—EvoTech Opera™, Molecular Devices IsoCyte™); (ii)—TDI CCD/flow cytometer (Amnis ImageStream™; (iii)—low-res laser scanners (CompuCyte iColor™, Acumen-Explorer™. These systems generally achieve assay rates of about 2-6 wells/min for real HCS assays. The Amnis ImageStream is unique as a CCD-based flow imaging system. However, it is generally slower than the microscope systems for most users, is a single-channel instrument, and has no sorting ability (nor could it sort efficiently without a faster sensor). The laser scanning instruments are not flow-based and generally do not resolve high-content information.

The normal workflow of biological assessment or screening a large number of biological cell samples is both time consuming, expensive on both reagents and biological cell samples and requires a series of separate analysis on different instruments. For example a common work flow in analysis of a large number of biological samples might contain in some or any order: (1) FACS (or CHip) to isolate cells of interest, (2) microscopy to identify localization changes using a marker, (3) hybridization array to qualitatively identify up-, down-regulation in response to a modifier and, (4) QPCR to get a quantitative measurement of expression changes (ideally at the level of about 100 genes, money and time allowing). One limiting issue is that a researcher needs to proceed serially through these methods on separate instruments with a great penalty in time and while trying to maintain a consistent sample for comparison purposes.

Several limitations exist for use of cell cytometry in a high through-put capacity. For instance, there is not an adequate cost-effective solution for (i) scale-up of HCS for drug discovery, (ii) for handling of small samples of highly heterogeneous primary cell types (e.g., flow biopsy or stem-cell biology); (iii) for finding rare cells (e.g. finding pluripotent cells for cancer diagnostics), (iv) image-based sorting/enrichment.

There also exists limitations for the uses of FACs, Automated Microscopy, and CCD Cytometers for high-throughput sorting based on phenotypic characteristics. For example, HCS with CCDs is frequently done in open wells (see e.g., Taylor, D. L., et al. Humana Press, Totowa N. J. 2007; Bullen A., Nature Reviews 7, 54-93, 2008; Haney, S. A., et al., Drug Discovery Today, 11, 889-894, 2008; Gough, A. H. and Johnston, P. A., Methods Mol. Biol. 356, 41-51, 2007; Lee, S., and Howel, B. J., Methods Enzymol. 414, 468-483, 2006; Pepperkok, R. and Ellenberg, J. Nat. Rev. Cell Biol. 7, 690-696, 2006; Eggert, U. S. and Mitchinson, T. J., Curr. Opin. Chem. Biol. 10, 232-237, 2006; Loo, L. H., et al., Nature Methods 4, 445-453, 2007; Proceedings of the Symposium on High-Content Analysis, San Fransisco, Calif., Jan. 5-9, 2009; Bleicher, K. H., et al., Nature Rev. 2, 369, 2003; Lang, P. et al., Nature Rev. 5, 343-356, 2006; Ding, G. J. F., et al. J. Bio. Chem. 273, 28897, 1998, Amnis website on the world wide web at amnis.com), on spotted slides (Carpenter A. E., et al. Genome Biology, 7:R100, 2006; Carpenter, A. E., et al., Nat. Rev. Genet. 5, 11-22, 2004; Wheeler, D. B., et al., Nature Genetics, 37, s25-s30, 2005), or in flow (George, T. C., et al J Immuno. Methods 311, 117-129, 2006). Even on high-density slides, the state of the art is largely determined by the performance of low-signal scientific CCD cameras. At 1024×1024-pixel image size, the frame rate due to buffering restrictions is either 15 or (conditionally) 30 frames a second (e.g., the latest Princeton Instruments/Roper or Hamamatsu). However even much slower rates are often mandated by low signal. Analysis of a single high-density spotted slide can take many hours. Autofocusing and mechanical motions, further limit throughput (accounting for the majority of the time budget on widefield imaging systems. CCD-based Amnis imaging flow cytometers are more limited in throughput and users typically report raw data acquisition (unclassified cells) from such a machine at 100 objects/min (see e.g., information on the world wide web at amnis.com/applications.asp). Thus, high content microscope-based systems are too slow and do not have a sorting capacity. Additionally, data storage rapidly requires gigabytes of storage capacity.

Accordingly, there is a need for a single, automated instrument for high throughput cell sorting based on phenotypic distinction from only one or a few cells per reading (to reduce noise from cell heterogeneity) which is inexpensive to run and operate, and with sufficient throughput to generate statistically significant answers.

SUMMARY OF THE INVENTION

The present invention generally relates to a high-throughput, high content screening (HCS) cytometry device based on image-analysis and sorting of particles (i.e. cells) based on particle (i.e. cell) phenotype. Thus, the present invention relates to a high-throughput, high content cytometry screening for phenotypic sorting of particles (i.e. cells) in a sample. The methods and compositions described herein combine desirable features of flow cytometry (FACS) and microscope-based high-content screening (HCS) to permit sorting of particles based on phenotypic characteristics such as asymmetry, shape, fluorescence or dye uptake/exclusion, and intracellular information (e.g., organelle shape and area). The present invention further permits intracellular localization assays to be performed, is highly sensitive to detection of rare cells, and can be used for time-synchronized sampling, which is not possible using FACS or HCS alone. The present invention is advantageous in that it allows identification and distinguishing of particles, e.g., cells based on gross morphological characteristics using line scan image analysis with a resolution which is high enough for distinguishing characteristics, but is of a resolution which does not significantly slow down the analysis, allowing for high throughput, high-content screening. One of the problems with 96- and 384-well plate-reader and plate-based image analysis systems is that they are static systems, requiring time for the focusing of beam for accurate and clear image capturing. In contrast, the present system, methods and apparatus performs image analysis on particles, e.g., cells, as they move or flow through a microchannel, therefore all particles, e.g., cells, are in focus allowing for rapid image capturing and accurate reading. Additionally, the present system, method and apparatus allows the particle, e.g., cell to be in the correct morphology, and reduces issues with cell aggregation which can be an issue with static 96- and 384-well plate-reader and plate-based image analysis systems.

The present invention generally relates to systems, instruments and methods which couple high-content screening (HCS) systems with line-scan imaging in a parallel flow instrument. In particular, the present invention relates to a high-capacity line-scan imaging module for fast imaging of multiple samples simultaneously. In some embodiments, the line-scan imaging module can identify and sort cells based on phenotype and/or morphological characteristics. In some embodiments, the line-scan imaging module performs 1-D and/or 2-D imaging of the cells. In some embodiments, the line-scan imaging can perform 3-D imaging of cells. In some embodiments the line-scan imager uses a detection volume which is larger than a cell being imaged and can be used to determine a cell phenotype based on the magnitude of light scattering and/or the ratio of two or more fluorescent markers, and/or cell morphology.

In some embodiments, the line-imaging module can be configured to receive samples from a high content screen module, such as a flow cytometer module, e.g. a parallel microfluidic cytometer (PMC module) such as a 384-well flow cytometer as disclosed herein. Accordingly, the present invention relates to methods for analyzing cell (or other components in a sample), by first sorting the cells using a high-throughput flow cytometer and then further sorting the cells based on phenotype using the line-imaging module. Such a system is referred to herein as a "parallel flow FACS-line scan imaging system".

In some embodiments, the line-imaging module can sort cells based on phenotype and/or morphological characteristics. In some embodiments, the phenotype includes protein localization or other such distinguishing or characteristic phenotypes.

In some embodiments, the line imaging module can be further configured to be connected to a second high content screening module, such as a high throughput analysis module which performs PCR analysis, such as, for example a module which can perform multiplex quantitative PCR (multiplex QPCR), referred to herein as a "multiplex QPCR module".

Accordingly, in one embodiment, the present invention relates to high-throughput FACs sorting cells then subsequently line-scan imaging for further sorting by cell phenotype and morphology in a high throughput system. In some embodiments, the line-scan imaging module passes a resolving detector just one-time through each cell, which adds the "high-content" of protein localization to unresolved fluorescence measurements (FACS), and will extend a class of well-developed HCS assays to the throughput of flow cytometry, in particular for cell phenotype.

Such a parallel flow FACS-line scan imaging system overcomes the throughput and cost issues that are limiting factors in the use of existing high-content screening (HCS) systems. The present invention relates to a multichannel microfluidic system equipped with algorithms, which is referred to herein as an imaging parallel microfluidic cytometer (PMC). Embodiments of the present invention advance the high-content assays by providing the throughput and content advantages of line-scan 1-D and 2-D imaging in parallel flow.

In particular, the current solution for imaging in HCS is automated wide-field microscopy, which has limited use for least three reasons; (i) it has no separation (sorting) ability, (ii) throughput speed is severely limited by hardware and, (iii) microscopy can actually gather too much image information. Microscope-based systems are generally hardware-limited by autofocus; but when they are not, and when full 2-D images are gathered, intermediate buffering and long-term storage quickly clog the data stream, and 2-D high-depth imaging requires significant storage requirements and clumsy data extraction. Furthermore, large 2-D images are not suitable for cell selection cytometry, because the images are too complex as raw data for use with cell-type algorithms for the basis of selection of cells. The inventors overcome this issue by providing raw data in line-scan images, such as 1-D line images or low complex 2-D line images.

Embodiments of the present invention of the use of the line-scan imaging device as disclosed herein is particularly useful for flow cytometry using phenotype as the basis for cell sorting on samples comprising very limited cell numbers, e.g., as little as ~100 cells per sample, (i.e. 100 cells per input sample well of the microfluidic device). Such a sample with a low number of cells is not enough cells for analysis by conventional flow cytometry (FACS). In some embodiments, the line-scan imaging device as disclosed herein can be used to sort particles (i.e. cells) in samples of about 1 μL volumes and cell counts <100 cells. Additionally, the line-scan imaging device as disclosed herein is also useful to detect multiple fluorescent markers in imaging mode, which is particularly useful for characterizing cell phenotype or in some instances the status of cell cycle, or cell differentiation, such as but not limited to stem cell differentiation and/or proliferation, as disclosed herein in the Examples.

In some embodiments of the present invention, the line-scan imaging device can be used in parallel with a 384-channel parallel microfluidic cytometer (PMC) (see FIGS. 1 and 2). In such an embodiment, the multichannel architecture of the microfluidic device of the line-scan device as disclosed herein allows for different samples, such as 384 unique samples for a cell-phenotype based screen to be read out in approximately 6-10 minutes (e.g., 6, 7, 8, 9, or 10 minutes), which is about 30-times the speed of a conventional fluorescence-activated cytometer (FACS) system. In some embodiments, the cell-phenotype based screen can be read out in less than 5 minutes (e.g., less than 4, less than 3, less than 2 or even less than 1 minute). Alternatively, the cell-phenotype based screen can be read in greater than 10 minutes (e.g., at least 11, at least 12, at least 13, at least 14, at least 15, at least 16, at least 17, at least 18, at least 19, at least 20 or more minutes).

Unlike FACS sorting, which can only sort cells from a single sample at one time and which requires cells from different samples to be sorted in sequential or subsequent FACS processing step, the present methods, apparatus, devices and composition allows for sorting of multiple different samples simultaneously, in real-time. As shown in FIG. 1, FIG. 2, and FIG. 18, in some embodiments, the present methods, apparatus, devices and composition allows for image analysis and subsequent sorting of 384 different samples simultaneously. In some embodiments, the multi-channel architecture of the microfluidic device of the line-scan device as disclosed herein can be configured for line-image scanning of any number of different or unique samples. In some embodiments, the number of samples which can be line-scan imaged simultaneously can be about at least 16, or at least about at least 32, or at least about 96, or at least about 384, or at least about 500, or between about 500-1000, or multiples of 384, e.g., 768, or about 1152, or about 1536, or about 1536, or about 1920, or about 2304 etc. In some embodiments, the number of samples which are processed simultaneously is determined by one of ordinary skill in the art and can be determine in part, by the sample capacity of commercially available and conventional microwell plates (e.g., 16-well, 32-well, 96-well, 384-well plates etc). In another embodiment, one can scan a "sheet" of samples, and automate the process to prepare a new sheet of samples which can be simultaneously scanned or processed.

In some embodiments, the line-scan imaging device can be used for high through-put screening to process samples on a series of microwell plates sequentially, for example but by no means a limited to, a line-scan imaging device can process 384 samples simultaneously from a first 384-well plate, and then process a next set of 384 samples simultaneously from a second 384-well plate and so on. In some embodiments, samples on a series of microwell plates (e.g., 16-well, 32-well, 96-well, 384-well plates etc) to be scanned sequentially through the microchannels of the line-scan imaging device is automated, e.g., using a robot, e.g., where the robot is programmed so that a series of microwell plates (e.g., a series of between 2-4, or 2-10, or 10-30, or 10-50, or 50-100, or about 100-200, or about 200-500, or about 1000, or more than 1000 microwell plates) is automatically processed through the line-scan imaging device as disclosed herein. In some embodiments, the series of microwell plates can comprise microwell plates in duplicate, or triplicate. In some embodiments, a sample microplate can also comprise samples in duplicate or triplicate. In some embodiments, the samples to be analyzed are added into the input of the microchannels using an automated pipettor, for example, using a robot controlled automated pipettor. In some embodiments, the microchannels of the line-scan imaging device are present in a microchip which is disposable, so microchannels are discarded after each microwell plate and before starting a new set of samples on a new microwell plate. In some embodiments, where the microchip is not disposable, a microwell plate comprising a wash fluid, e.g., water or phosphate buffered saline (PBS), is used to input into the microchannels to clean and flush the microchannels. In some embodiments, a microwell plate is interdispersed between sample microwell plates to clean the microchannels. In some embodiments, a microwell plate comprising "bar-code bead" e.g., luminex bead can be used between the sample microwell plates to identify the samples being processed. In some embodiments, each sample microwell plate comprises at least one well comprising bar-code beads e.g., luminex bead to identify the sample microwell plate. In some embodiments, a well comprising bar-code beads e.g., luminex bead, can also comprise sample cells, such as test sample cells or a reference sample cells.

The plurality of microchannels in the microfluidic device of the line-scan imaging device also allows the signal integration time to be varied over a larger range than is practical in single-channel FACS and is suitable for detection of rare cells in a high background of negatives cells. Such detection is useful for rare-cell assays and use of the compositions described herein in a clinical setting. As discussed previously, the line-scan imaging device can also be used to identify and select for cells based on cell phenotype from a sample comprising a few number of cells, such as about 100 cells/1 μl where about 1-2 μl per sample is required.

One aspect of the present invention relates to a line-scan imaging device for rapid image analysis of particles in multiple samples of interest, comprising: (a) a microfluidic device comprising a plurality of microchannels, wherein each microchannel has an inlet and at least one outlet; (b) a scanning detector configured to record emitted fluorescence in a portion of each of the plurality of microfluidic channels of the microfluidic device; and (c) an output device configured to receive data input from the scanning detector.

In some embodiments, the output device comprises a data storage device. In an alternate embodiment, the output device comprises a data analysis system that determines cell phenotypes from fluorescence signatures.

In some embodiments, the scanning detector comprises at least one laser, for example emitting different wavelengths, and as such the line-scan image device as used herein comprises a multisource scanning detector.

In some embodiments, the scanning detector is a modified version of a single channel cytometer, which is modified for example by increasing the spatial resolution of the fixed detector, adding a scanner and a linear array and strobe illuminator. In alternative embodiments, the scanning detector is a parallel microfluidic cytometer (PMC).

In some embodiments, the scanning detector is a 1-D line image detector, or a sparse 2-D line image detector, such as a low complexity 2-D line image detector. In some embodiments, the scanning detector is a laser-induced florescence (LIF) detector. In some embodiments, the scanning detector comprises a plurality of photomultipliers (PMTs), for example at least 4 or at least 5 or at least 6, or at least 7 or at least 8 or more PMTs. In some embodiments, the wavelength is detected by a single-cathode PMT or a multi-cathode PMT or an avalanche photodiode array (APD). In some embodiments, the scanning detector comprises a cascade of PMTs.

In some embodiments, the dimension of the detection volume (as detected by the detector) can be parallel to the scan direction, and can be between 1 and 5 μm (e.g., at least 1, at least 2, at least 3, at least 4, at least 5 μm). In one embodiment, the laser spot geometry is elliptical (e.g., 3 μm by 50 μm), although it is contemplated that any laser spot geometry can be used in the devices, methods and systems as disclosed herein.

In some embodiments, the scanning detector has a spot size of between 3-4 μm, for example a spatial resolution spot size of 3.5 μm. In some embodiments, the spot size is about the same size, or less, than the diameter of the width of microchannel, for example if the micochannel has a diameter of 100 μm, the spot size can be less than about 100 μm in its diameter.

In some embodiments of the line-scan imager device, a large laser spot size is used (e.g., 30×100 microns, or 30×30 microns). Such a large laser spot size can be used for high throughput sorting of larger cells, for example, based on color ratio measurements without the need to resolve intracellular and internal cell structure, and can be used, for example, for a high sensitivity to identify rare cells. In some embodiments of line scan imaging device, a larger spot size will decrease the focus and clarity of the image, but can be useful to identify larger cells and/or rare cells, and/or to distinguish cells on the basis of light scattering, or the ratio of two or more different fluorescent markers. In some embodiments, the spatial resolution spot size can be determined by the user to identify a cell type of a specific size. For example, in some embodiments, the spatial resolution spot size can identify cells within the range of 1-50 µm, for example a spatial resolution spot size of 3.5 µm can be used to identify cells of about 10 µm, or a spatial resolution spot size of about 4-5 µm in can be used to identify a yeast cell of about 6 µm in diameter, or a spatial resolution spot size of about 1-3.5 µm can be used to identify cells about 1 µm, such as bacterial cells, or a spatial resolution spot size of about 3.5-5 µm can be used to identify cells about 50 µm such as heart cells and neurons. In some embodiments, the spatial resolution spot size can be adjusted accordingly to identify cells of about 3-15 µm in diameter, or between about 3-20 µm in diameter, or between about 1-10 µm in diameter, or cells about 20-50 µm in diameter, or cells greater than about 50 µm in diameter. In some embodiments, the spatial resolution spot size is adjusted so it allows enough resolution of the cell to see markers and/or internal structures of the cell and resolve details inside the cells yet being quick enough for quick image capture for high throughput analysis.

In some embodiments, the detector for capturing the line-scan images is configured to capture images of the particle, e.g., a cell as it flows through a microchannel. Surprisingly, as the particles are in the microchannel, each particle, e.g., cell is always in focus. Accordingly, no time is needed for focusing the image detector in the present system, which is a significant advantage over plate-reader image analysis systems, where cells in a plate microwell are not in focus and time is required for focusing the image detector for clear image capture. In some embodiments, the line-scan imaging device comprises a microfluidic device comprising a plurality of microchannels, wherein each microchannel of the plurality of microchannels is at least 50 µm wide in diameter, or at least 100 µm wide in diameter. In some embodiments, the diameter of each microchannel (e.g., depth) is between 30 and 300 µm (e.g., between 30-175, 30-150, 30-125, 30-100, 30-75, 30-50, 30-40, 50-75, 50-100, 50-125, 50-150, 50-175, 50-200, 75-200, 100-200, 125-200, 150-200 or 175-200 µm, or about 200-300 µm). In some embodiments, the diameter of the width of a microchannel is not greater than 300 µm wide in diameter. In some embodiments, the microchannel diameter is configured so that the detector does not need to focus to accurately and clearly capture the particles, e.g., cells as they flow the microchannel, or so that the detector need only a narrowly-adjusted focus for focusing on particles as they flow through the microchannel.

In some embodiments, the scanning detector records emitted fluorescence at least every 1 µm across the diameter of each microchannel of the plurality of microchannels. In some embodiments, the scanning detector records emitted fluorescence at least every 1 µm along the longitudinal length of a scanning window of each microchannel of the plurality of microchannels. In some embodiments, the scanning detector records emitted fluorescence at an interval of 3 µm or less across the diameter of each microchannel of the plurality of microchannels (e.g., less than 2.8, less than 2.6, less than 2.4, less than 2.2, less than 2.0, less than 1.8, less than 1.6, less than 1.4, less than 1.2, less than 1.0, less than 0.8, less than 0.6, less than 0.4 or less than 0.2 µm intervals). In some embodiments, the scanning detector records emitted fluorescence at an interval of between 5-10 µm, such as at 6 µm or less across the diameter of each microchannel of the plurality of microchannel, (e.g., in some embodiments, less than about 10 µm, or less than about 9 µm, or less than about 8 µm, or less than about 7 µm, or less than about 6 µm, or less than about 5 µm, or less than about 4 µm, or less than about 3 µm intervals).

In some embodiments, the scanning window is between 50 µm-200 µm in length, and in some embodiments, the scanning window is 320 µm in length, and in some embodiments, the scanning window is 100 µm in length.

In some embodiments, the scanning detector collects at least 320 points at 1 µm spacing along the linear length of a portion of each of the plurality of microchannels. In some embodiments, the scanning detector collects at least 100 points at 1 µm spacing along the linear length of each of the plurality of microchannels.

In some embodiments, each microchannel of the plurality of microchannels on the microfluidic device is configured for focusing, such as vertical hydrodynamic focusing. In some embodiments, vertical hydrodynamic focusing is achieved by using multiple crossing junctions of each microchannel to flow into a single analytical microchannel, where a single analytical microchannel is a scanning window or analytical portion of the microchannel. In some embodiments, the vertical hydrodynamic focusing locates cells to a zone of 20 µm or smaller (e.g., less than 18, less than 16, less than 14, less than 12, less than 10, less than 8, less than 6, less than 4, or less than 2 µm) in the direction of the optical focus. In some embodiments, vertical hydrodynamic focusing allows 4 µm to be detected with a 40× microscope objective.

In some embodiments, the microfluidic device of the line-scan imaging device comprises a plurality of microchannels, where inlet of each of the plurality of microchannels has a sample well for input sample injection. In some embodiments, the each microchannel is also configured to have at least one positive outlet and at least one negative outlet, e.g., the microchannel has a junction such as a Y- or T-junction, where one arm is a positive outlet and one arm of the junction is a negative outlet. Such positive and negative outlets are useful for collecting positively sorted cells (i.e. in at the positive outlet) or negative (i.e. non-selected) cells (at the negative outlet). Typically, the junction point is downstream of fluid flow from the scanning window. Fluid flow and cells sorting is directed by a switch, such as a microswitch or MEM switch, which can direct a scanned cell to the positive arm and positive outlet or to the negative arm of the microchannel and negative output. In some embodiments, the each positive outlet and each negative outlet has a positive sample well for positive output sample collection or a negative sample well for negative sample collection. In some embodiments, sample wells at the inlet and outlets of the microchannels are configured for pipette sample addition or suction pipetting, and configured in such a way that sample addition or extraction can be performed using an automated pipettor, for example, a multiplex pipettor which can be operated by hand, or a multiplex pipettor which can be operated automatically, for example, using a robot.

In some embodiments, particle (i.e. cell) sorting of particle/cells in each microchannel of the plurality of microchannels comprises a piezoelectric microswitch, which is configured to be operated by the output of the storage device and/or comparison module. In some embodiments, cells are sorted based on specific cell phenotype and cell features, as disclosed in Table 1.

In some embodiments, the data which is received by the storage device (i.e. the storage device input data) is the output data of fluorescence values recorded from the plurality of PMTs of the scanning detector. In some embodiments, the detector constructs a line-scan image of a cell as it travels through a microchannel. In some embodiments, a digital line-scan image is at least about 10-bit, or at least about 14 bit, or at least about 16-bit digital line-scan image of at least one cell from a plurality of cells that are flown through at least one microfluidic channel. In some embodiments, the digital line-scan image is greater than 16-bit, for example 2 4-bit or greater than 24-bit images. In some embodiments, the storage device is configured to convert the output data of florescence values recorded from the plurality of PMTs to 14-bit or greater digital value, e.g., for example a 16-bit digital value or 24-bit digital value, for example using an analogue to digital converter (ADC). In some embodiments, the storage device then converts the digital line-scan image, e.g., a 16-bit digital value to line-scan images. In some embodiments, the line-scan images are 5×5 2-D images or 1×5 1D images. In some embodiments, the storage device stores at least 1, or at least 2, or at least 3, or at least 4, or at least 5, or at least 6, or at least 7, or at least 8, or at least 9, or at least 10, or at least 11, or at least 12, or at least 13, or at least 14, or at least 15 images per cell. In some embodiments, the storage device stores at least 10 images per cell (i.e. herein referred to as a "10 line-scan image").

In some embodiments, the storage device is connected to a comparison module, such as a non-human computer. In some embodiments, the comparison module compares at least one line scan image, or a least 5, or a least 10 line image scans of the cell with a reference point indicating a cell phenotype. In some embodiments, the reference point indicating a cell phenotype is a reference line scan image of cell phenotype. In alternative embodiments, the reference point indicating a cell phenotype is a value from an algorithm indicating a cell phenotype.

In some embodiments, the comparison module is configured to analyze at least one line-scan image or a plurality of line scan images from each cell by comparison with a reference line scan image, and wherein if the line-scan image of the cell has substantially similar cell features, such as those in Table 1, as a reference line scan, the comparison module sends instructions to the microfluidic device to trigger or de-select switching of the piezoelectric microswitch in the microchannel in which the cell was scanned, enabling selection of the cell.

In some embodiments, the comparison module is configured to analyze a line-scan image, or a plurality of line-scan images of a cell via a cell-typing algorithm, and wherein the identity of cell type via the cell type algorithm triggers or de-selects switching of the piezoelectric microswitch in the microchannel in which the cell was scanned, enabling selection of the cell. In some embodiments, if a line image of a cell has substantially similar cell features as the line image of a reference line scan image, it identifies a cell with a "positive" cell type and triggers fluid flow along the microchannel to a positive sample collection well. In some embodiments, if a line image of a cell is significantly different to a reference cell type, the cell is identified as a "negative" cell and triggers fluid flow along the microchannel to a negative sample collection well.

In some embodiments, a line image of a cell identifies the cell as a positive cell or a negative cell by comparison of the line image of the cell with at least one reference point. In some embodiments, a line image of a cell is identified as a positive cell or a negative cell using a cell-type algorithm.

In some embodiments, the storage device also stores line images of reference cells, which can be used in a comparison with the 10 line scan image of the cell that has been scanned. In some embodiments, the storage device comprises a comparison module, where the output of the storage device is used as the input for the comparison module. In some embodiments, the comparison module is a computer. In some embodiments, the comparison module comprises computer readable media. In some embodiments, the comparison module can perform analysis of the 10 line image data, for example, using a cell type algorithm to characterize the phenotype of the scanned cell from which the 10 line image data was generated.

In some embodiments, the analysis by the comparison module in the storage device identifies the cell as having a particular pre-defined phenotype and/or one or more desired cell feature(s), and thus the cell is identified as a "positive" cell based on cell phenotype. Depending on if the cell is identified as a "positive" or "negative" cell (i.e. a positive cell is a cell with desired phenotype to be selected and a negative cell is a cell lacking the desired phenotype and not-selected), the comparison module sends output instructions to operate a microswitch on the microchannel to select or deselect the cell. For example, where a "positive" cell is identified by the comparison module, the output is a "positive" or "select" signal, which triggers the microswitch to be in orientation such that the sample fluid flow (or cell) flows down the microchannel junction arm towards the positive arm and positive microchannel outlet, where the cell can be collected in the positive sample well. Alternatively, where a "negative" cell is identified by the comparison module, the output is a "negative" or "not-select" signal, which triggers the microswitch to be in orientation such that the sample fluid flow (or cell) flows down the microchannel junction arm towards the negative arm and negative microchannel outlet, which is collected in the negative sample well.

Thus, in some embodiments, the storage device comprises a comparison module which is configured to analyze the 10 line-scan image of each cell via cell-typing algorithm, and wherein the identity of cell type via the cell type algorithm triggers or de-selects switching of the piezoelectric microswitch in the microchannel in which the cell was monitored for cell sorting. Thus, in some embodiments, the storage device comprises a comparison module to positively identify a cell of desired phenotype, and where the cell matches a positive cell type, for example, using a cell type algorithm, the comparison module sends instructions to the microswitch present on the microchannel to trigger fluid flow along the microchannel to a positive sample collection well. Similarly, in some embodiments, the storage device comprises a comparison module to identify a cell, which does not match a desired phenotype (i.e. a negative cell), and where the cell does not matches a positive cell type (i.e. a negative cell) using a cell type algorithm, the comparison module sends instructions to the microswitch present on the microchannel to trigger fluid flow along the microchannel to a negative sample collection well.

In some embodiments, the line-scan imaging device is configured such that the microchannels to receive samples from a FACs machine. In one embodiment, the input sample wells receive samples from the output of a plurality of microfluidic channels from a parallel microfluidic cytometer (PMC), as disclosed herein. In some embodiments, the inlet of the plurality of microchannels are in liquid or fluid communication through a capillary passageway to the output of a plurality of microfluidic channel of a parallel microfluidic cytometer (PMC).

In some embodiments, the line-scan imaging device as disclosed herein is configured so the output of the microchannels can be processed directly by a High Content Screening (HCS) assay or device for expression analysis, such as sequencing or PCR HCS assay, such as a quantitative PCR device. In some embodiments, the output of each microfluidic channel of a plurality of microfluidic channels is in liquid or fluid communication through a capillary passageway to the output of a high content analysis screening assay, such as a multiplex quantitative PCR module, as disclosed herein. In some embodiments, any HCS assay or module known by a person of ordinary skill in the art for downstream expression analysis can be used, for example, HCS immunodetection modules, such as ELISA and the like.

BRIEF DESCRIPTION OF THE DRAWINGS

FIGS. 1A-H show exemplary results from the parallel microfluidic cytometer (PMC) and line image. FIG. 1A is a schematic drawing showing a parallel microfluidic cytometer (PMC) for cell-based assays. The system is designed for automated fluorescence measurements on 384-channel microfluidic plates and includes a temperature-controlled microfluidic "chip" (384 channels), a scanning detector, and automated pippetor/sample elevator for automated maintenance of cell suspensions/cultures; The microdevice has channels with a hemispherical cross-section of 60-µm radius; Cell suspensions are pulled by vacuum suction from injection wells using a positive-displacement syringe pump. FIGS. 1B and 1C show an optical diagram of the laser-induced fluorescence (LIF) detector including detail of rotary scanner that introduces the 488-nm laser beam and returns fluorescence to four photomultipliers (PMTs). The scanner uses a 3-inch radius of rotation, a DC rotary motor, and optical encoder; FIGS. 1D and 1E show an image of a typical condensed-time data scans and FIG. 1F shows reduced-difference scan to identify positives.

FIG. 1G shows a 384-channel microfluidic plate and FIG. 1H shows a segment of data collected from several channels. A short time sequence from one of four photomultipliers is shown with each pixel representing 35 µm in the horizontal scan direction. Data is collected at a rate of 3 scans/s (0.33 vertical displacement of each row of pixels in the data image); 240 s of data are shown. Signal amplitude is shown in RGB color scale with blue representing low signal and red high signal.

FIG. 2A is a histogram of dsRed-cell counts for a cell dilution curve (dsRed-tagged cells diluted serially with GFP cells). The histogram is organized according to the input (sample) well placement on the microfluidic plate, i.e. organized into 8 rows and 48 columns to match a multiple of the 96-tip array pipettor. Counts for all 384 microfluidic channels are shown. Sample dilutions are run redundantly in 2-ea. columns of 8-well rows (layout on the microfluidic device), i.e., 24 channels for each dilution. FIG. 2B shows a graph of the total counts summed for each sample and used to generate the serial dilution curve (log vertical scale) which shows slight saturation at the lowest dilution (100% positives, right side of the figure). This is probably due to double-cell counts at high dsRed-cell density.

FIGS. 3A-3C show an example of line-scan images of 6-µm beads (one of four PMTs). FIG. 3A shows 350 pixels in line scan (X) vs. scan number (Y) with fluorescence intensity values shown as growing from blue to green to red. FIGS. 3B and 3C are magnified areas of FIG. 3A, with FIG. 3B showing image of 6-µm bead moving at a higher speed through the detector, and FIG. 3C showing an image of 6-µm bead moving at a slower speed through the detector. The slower speed yields a more 2-D "picture-like" image.

FIGS. 4A-4D show preliminary results showing line-scan HCS data using a 3.5-µm laser spot to scan αSyn-GFP expression patterns in S. cerevisiae. The modified DNA sequencing detector can distinguish the localization patterns. FIG. 4A shows raw scans for negative cells, and FIG. 4B shows raw scans for positive cells showing αSyn aggregates. In FIGS. 4A and 4B, whole cells are red and αSyn-GFP is green.

FIGS. 4C and 4D shows filtered data using a modified "roundness" parameter, which distinguishes positive (in-duced) sample shown in FIG. 4C from a negative cells with baseline αSyn expression shown in FIG. 4D.

FIG. 5A shows eight variations of the 4-sheath configuration labeled "A"-"H"(right side of die), are included on the single test die. The two layers of etched channels are indicated as red (top plate, shown in FIG. 5A) and black (shown in FIG. 5B) respectively. A single laser-drilled hole is provided for each input or output (S1-S4) and for a common suction port (common to configurations A-H, right side of die). The full die size is 3×7 cm (Lin A, et al. *Biomicrofluidics* 3, 014101-014112, 2009).

FIG. 6A shows three positives, and FIGS. 6B and 6B show three negatives. The confocal slit in the detector discriminates strongly against out-of-focus images. The right column shows the several principal line-scan image types that are generated depending on how the laser scanner traverses the cell. The dashed arrow shows the location of the single line scan that is taken per cell. Some of the diagnostic signatures are surprising.

FIG. 7A shows typical cytosolic localization of the NFkB-GFP reporter and mitochondrial IMS-RP in healthy cells, FIG. 7B shows an intermediate distribution of NFkB-GFP to the nucleus and potentially some leakage of IMS-RP from mitochondria, FIG. 7C shows a strong localization NFkB-GFP in the nucleus and diffuse localization of RFP signal indicating an apoptotic fate, and FIG. 7D shows necrotic cells displaying autofluorescence in both channels.

FIG. 10A shows an embodiment using a scanner permitting one to use multiplex excitation lasers using a time delay. This avoids duplicating the entire detection system as is often done, adding to the cost, for FACS. Similarly, embodiments using strobe illumination, by injecting a single laser as a fast series of scans, can have noise-rejection advantages. Typical parameters include: flow velocity/2 mm/s, scan velocity/100 mm/s, Laser spot/1 µm×30 µm, time delay between laser spots/5-10 µs. FIG. 10B shows an embodiments of how traces for the dual detection (or strobe sequence detection) can be obtained.

FIG. 12 shows *S. cerevisiae* induced to three progressive, highly distinct, stages of Sup35 amyloid organization. Cells at left express ubiquitous Sup35-GFP in a non-prion state. These can be induced into the middle state in which the same protein is organized in striking ring structures (amyloid which does not induce [PSI+]), then by further induction into condensed prions that induce [PSI+] (Krishnan, R., and S. L. Lindquist. *Nature*. 435:765-72, 2005; Shorter, J. and Lindquist, S. L., *Nature Rev. Genet.,* 2005). Cell diameter is 3-6 µm.

FIG. 13A shows a scan-view cytoplasmic projection which is much larger on an adherent cell than a cell in FIG. 13B for a cell in solution. However many cells most important to immune response are natively non-adherent and would be optimally studied in flow, rather than as adherent cells in a microscope.

FIG. 22B shows the raw data which is collected at 300 pixels per 16-channel (or 384 channel) scan and 12 scans per second.

FIGS. 24A-24B show exemplary calibrations for a dilution study using primary splenocytes. Ratio of GFP/yellow channels as a plot of objects and as histogram for a positive sample (FIG. 24B) and a negative sample (FIG. 24A). From the histogram it is determined that cells with a PMT ratio greater than 0.8 are (i) GFP cells, and (ii) represent about half of the cell number that was contained in the GFP source sample.

FIGS. 25A-25B show examples of calibration for a dilution study on primary leukocytes. For all the objects identified by the scatter detector we plot the maximum GFP channel value vs. the yellow channel value. Note that most objects in the negative sample have lower fluorescence than the positive sample, a more sensitive measure is made by comparing the ratio of the two PMTs.

FIGS. 28A-28B show data for a proof of principle nuclear translation (NT) assay. The FWHM for the green and orange channels are compared in a scatter plot. For the "unstimulated" CDFE sample cells (FIG. 28A), the wider green line scan skews the sample above the center diagonal line (proving marker in the cytoplasm). FIG. 28B shows "stimulated Sytox Green" sample cells, with the distribution centers along the diagonal (marker confined to the nucleus).

FIGS. 29A-29B show proof of principle of a nuclear translation (NT) assay. FIG. 29A shows representative line scans from each sample showing green fluorescent signal differences between whole cell marker and nuclear stain when compared to orange nuclear stain (FWHM point for normalized scans marked by blue line). FIG. 29B shows an algorithm classified objects by first eliminating all green signal outside of green FWHM and inside of orange FWHM, then measuring the remaining green signal. This value is significantly larger for "positives" (stimulated cells) in the NT assay.

FIGS. 36A-36C show, on the left are six K-S means heat maps showing the variance between the sample and a reference sample for seven features: the three on left should correlate for all samples and four on right should correlate for negative samples only. The p-values for each sample and feature in (FIG. 36A) are shown in the table in FIG. 36C. In FIG. 36B, the inventors show K-S means ladder charts for four of the 42 k-S means tests depicted in the heat maps. In Sample S12, a positive sample the inventors observed a feature comparing red channel symmetry and showing high correlation (p-value=0.30) and green channel symmetry showing low correlation (p-value<0.001). In Sample 23, high correlation in red (p-value=0.70) and also in green (p-value = 0.26) is observed. From this one can conclude (to 95% certainty) that the first sample is not negative (e.g., positive) and the second one is.

DETAILED DESCRIPTION OF THE INVENTION

Figures 1G, 1H:
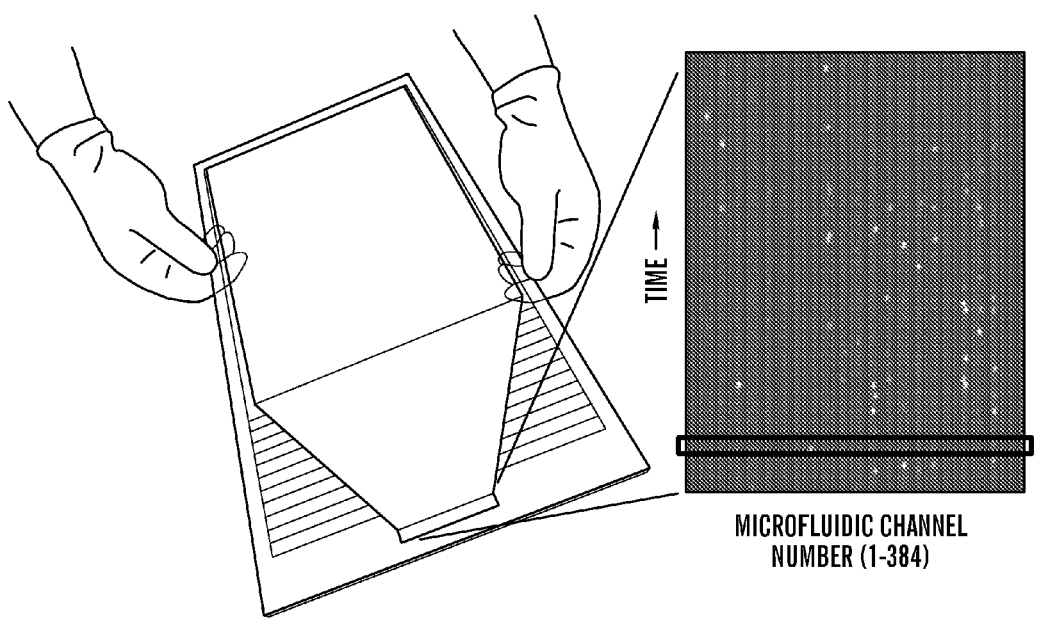

The present invention generally relates to systems, instruments and methods which couple high-content screening (HCS) systems with line-scan imaging module in a parallel flow instrument. The present invention permits (i) fast processing of high sample numbers, (ii) 1-D imaging capability for intracellular localization assays, (iii) identification and sorting of rare cells with high sensitivity, and (iv) time-synchronized sampling (e.g., real time cell assays).

In particular, the present invention relates to a high-capacity line-scan imaging module for fast imaging of multiple samples simultaneously. In some embodiments, the line-scan imaging module can identify and sort cells based on phenotype and/or morphological characteristics. In some embodiments, the line-scan imaging module performs 1-D and/or 2-D imaging of the cells. In some embodiments, the line—scan imaging can perform 3-D imaging of cells.

In some embodiments, the line-imaging module can be configured to receive samples from a high content screen module, such as a flow cytometer module, e.g. a parallel microfluidic cytometer (PMC module) such as a 384-well flow cytometer as disclosed herein. Accordingly, the present invention relates to methods for analyzing cell (or other components in a sample), by first sorting the cells using a high-throughput flow cytometer and then further sorting the cells based on phenotype using the line-imaging module. Such a system is referred to herein as a "parallel flow FACS-line scan imaging system".

In some embodiments, the line-imaging module can sort cells based on phenotype and/or morphological characteristics. In some embodiments, the phenotype includes protein localization or other such distinguishing or characteristic phenotypes.

In some embodiments, the line imaging module can be further configured to be connected to a second high content screening (HCS) module, such as a high throughput analysis module which performs PCR analysis, such as, for example a module which can perform multiplex quantitative PCR (multiplex QPCR), referred to herein as a "multiplex QPCR module".

This invention is not limited in its applications to the details of construction and the arrangement of components set forth in the following description or illustrated in the drawings. Aspects of the invention are capable of other embodiments and of being practiced or of being carried out in various ways. For example, illustrative embodiments of the invention are described below with reference to use in a line scan module. However, it should be understood that aspects of the invention may be used in other suitable systems for any suitable application. For example, aspects of the invention relate to a method and apparatus for high throughput or high content imaging of cells for analysis. While this aspect of the invention is described in conjunction other HCS modules, such as FACs module or PMC module, and multiplex QPCR module, the line-scan module as disclosed herein may be used in other applications. Similarly, aspects of the invention are described in conjunction with imaging a live cell or dead cells without causing necrosis. However, aspects of the invention are not limited in this regard, and may in some cases cause necrosis of a living cell and/or may be used with dead cells or compounds that were never previously living. For example, aspects of the invention may be used with any biological material, including tissue samples, organs or organ samples, spores, viruses, biopsy samples, tumor samples, fixed cells, etc.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The term "high-content screening" or "HCS" as used herein refers to assays of a sample where the output result of the assay or analysis is significant information about the sample. Typically, HCS refers to microscope based imaging whereby the output result of the analysis is significant information of the morphology or phenotype and structural components of a cell or sample being analyzed. In some embodiments, HCS screening also refers to other assays where the output result of the assay or analysis is significant information about the sample or cell, such as but not limited to, gene expression analysis, e.g., quantitative RT-PCR and microarrays, post-translational analysis, such as epigenetic assays, and protein expression analysis, e.g., proteins arrays.

The term "imaging" as used herein, for example in the context of the term "line-scan imaging" refers to the representation or reproduction of a particle form, e.g., a cell, by way of a visual representation (i.e., the formation of an image). In some embodiments, the term imaging as used herein refers to a basic visual representation of part of intracellular form of a cell, for example, in some embodiments, imaging refers molecular imaging of the cell, where fundamental molecular pathways inside the particle or cell are imaged a noninvasive manner. Alternatively, in some embodiments, for example where a larger scan spot size is used, imaging refers to the visual representation of the outside of the particle or cell.

The term "low flow" refers to any element, component or capillary channel on a microfluidic device which has a preferred flow rate of less than 200 µl/min flow rate or any rate below, for example, in the range of 0-199.9 µl/min, or for example within the range of 0.1 µl/min to 10 µl/min or 1.0 µl/min to 50 µl/min, or in the range of 50 µl-100 µl/min or in the range of 100-199.9 µl/min or any range therebetween. In some embodiments, a flow volume per minute of 2 or 3 or 4 or 5 to 10 times slower that the flow rate of a high flow chamber to which is fluidly connected to via an intermediately reservoir chamber.

The term "inlet" is the passageway of fluid into a chamber or channel.

The term "outlet" is the passageway of fluid out of a chamber or channel.

The term "elutant" or "eluted sample" as used herein refers to a sample that is collected after processing with at least one module of the microfluidic device.

The term "microchannel" as used herein, refers to a channel that is sized for passing through microvolumes of liquid.

The term "channel" as used herein means any capillary, channel, tube or grove that is deposed within or upon a substrate.

The term "enriching" is used synonymously with "isolating" cells such as, but not limited to, bacterial cells, and means that the yield (fraction) of cells of one type is increased over the fraction of cells of that type in the starting culture or preparation.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a preparation of one or more partially and/or terminally differentiated cell types, refer to a population of cells that contain fewer than about 20%, more preferably fewer than about 15%, 10%, 8%, 7%, most preferably fewer than about 5%, 4%, 3%, 2%, 1%, or less than 1%, of cells that are not selected or desired.

The term "biological sample" as used herein refers to a cell or population of cells or a quantity of tissue or fluid from a subject. Most often, the sample has been removed from a subject, but the term "biological sample" can also refer to cells or tissue analyzed in vivo, i.e. without removal from the subject. Often, a "biological sample" will contain cells from the animal, but the term can also refer to non-cellular biological material, such as non-cellular fractions of blood, saliva, or urine, that can be used to measure gene expression levels. Biological samples include, but are not limited to, tissue biopsies, scrapes (e.g. buccal scrapes), whole blood, plasma, serum, urine, saliva, cell culture, or cerebrospinal fluid. Biological samples also include tissue biopsies, cell culture. A biological sample or tissue sample can refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the sample is from a resection, bronchoscopic biopsy, or core needle biopsy of a primary or metastatic tumor, or a cellblock from pleural fluid. In addition, fine needle aspirate samples are used. Samples may be either paraffin-embedded or frozen tissue. The sample can be obtained by removing a sample of cells from a subject, but can also be accomplished by using previously isolated cells (e.g. isolated by another person), or by performing the methods of the invention in vivo. Biological sample also refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, the biological samples can be prepared, for example biological samples may be fresh, fixed, frozen, or embedded in paraffin.

The terms "patient", "subject" and "individual" are used interchangeably herein, and refer to an animal, particularly a human, to whom it is desirable to analyze a cell or particle population in a biological sample obtained from the subject. In some embodiments, a subject is need of diagnosis of a disease or disorder, for example, diagnosis of a rare cell condition or disease in a subject, whereby a biological sample is analyzed using the devices, systems and methods as disclosed herein. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and any domestic animal or pet, as well as non-mammals such as chickens, amphibians, reptiles etc. In one embodiment, the subject is human. In another embodiment, the subject is an experimental animal or animal substitute as a disease model. Suitable mammals also include members of the orders Primates, Rodenta, Lagomorpha, Cetacea, Homo sapiens, Carnivora, Perissodactyla and Artiodactyla. Members of the orders Perissodactyla and Artiodactyla are included in the invention because of their similar biology and economic importance, for example but not limited to many of the economically important and commercially important animals such as goats, sheep, cattle and pigs have very similar biology and share high degrees of genomic homology among themselves and to humans.

The term "computer" can refer to any apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip.

The term "software" can refer to prescribed rules to operate a computer. Examples of software include: software; code segments; instructions; computer programs; and programmed logic.

The term a "computer system" may refer to a system having a computer, where the computer comprises a computer-readable medium embodying software to operate the computer.

The term "proteomics" may refer to the study of the expression, structure, and function of proteins within cells, including the way they work and interact with each other, providing different information than genomic analysis of gene expression.

Compositions or methods "comprising" one or more recited elements may include other elements not specifically recited. For example, a composition that comprises a fibril component peptide encompasses both the isolated peptide and the peptide as a component of a larger polypeptide sequence. By way of further example, a composition that comprises elements A and B also encompasses a composition consisting of A, B and C. The terms "comprising" means "including principally, but not necessary solely". Furthermore, variation of the word "comprising", such as "comprise" and "comprises", have correspondingly varied meanings. The term "consisting essentially" means "including principally, but not necessary solely at least one", and as such, is intended to mean a "selection of one or more, and in any combination." In the context of the specification, the term "comprising" means "including principally, but not necessary solely". Furthermore, variation of the word "comprising", such as "comprise" and "comprises", have correspondingly varied meanings.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The term "statistically significant" or "significantly" refers to statistical significance and generally means a two standard deviation (2 SD) below normal, or lower, amount of the amyloid aggregates or incidence of biofilm formation caused by bacteria infection. The term refers to statistical evidence that there is a difference. It is defined as the probability of making a decision to reject the null hypothesis when the null hypothesis is actually true. The decision is often made using the p-value.

The use of the word "a" or "an" when used in conjunction with the term "comprising" in the claims and/or the specification may mean "one" but is also consistent with the meaning of "one or more", "at least one" and "one or more than one."

Other than in the operating examples, or where otherwise indicated, all numbers expressing quantities of ingredients or reaction conditions used herein should be understood as modified in all instances by the term "about." The term "about" when used in connection with percentages can mean±1%.

This invention is further illustrated by the following examples which should not be construed as limiting. The contents of all references cited throughout this application, as well as the figures and tables are incorporated herein by reference.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Line-scan Image Module

Embodiments of this invention relate to a line-scan image module. In some embodiments, the line-scan image module is a parallel channel optical scanning system for rapid image analysis of particles (e.g. cells) in a plurality of samples of interest (e.g. biological samples) comprising: a microfluidic device comprising a plurality of microchannels, wherein each microchannel has an inlet and at least one outlet; (2) a scanning detector configured to record emitted fluorescence in a portion of each of the plurality of microfluidic channels of the microfluidic device; and (3) an analysis system configured to receive data input from the scanning detector. In some embodiments, the analysis system comprises a storage device.

In one embodiment, an exemplary line-scan imaging module comprises, a microfluidic device comprising at least 32 microchannels, each microchannel about 100 μm-200-μm in diameter, where each sample to be scanned flows at about 1.2 μl-per-minute (@200 Hz) per channel, and where approximately 0.1 mL of sample is scanned at any one time. Each sample to be scanned requires about 2 μL @ about 500-2000 cells/μL, or at least 1000 cells/μL. In one embodiment, an exemplary line-scan imaging module comprises a scanning detector which comprises a 10 Mhz Texas Instruments 1610 ADC (80 pixels/microfludic-channel) on each color channel, with 80 pixels dedicated to each 100-μm-wide microfluidic channel. The laser spot is 1 μm×30 μm, with a 1-D-Resolution/1 μm(X), Scan-rate/10-200 Hz. In some embodiments, raw throughput is calculated to be 22ea. 384 lane plates per hour for a binary assay, including the time required for the pipettor refresh cycle (30 s) and scanner turn-around time (20%). A calculation of the throughput limit determined by the 1610 ADC board is provided in Table 2.

Microfluidic Device.

The microfluidic device to be used in the line-scan imaging device as disclosed herein can comprise a plurality of microchannels. In some embodiments, the more channels increases the throughput of samples which can be processed in parallel (i.e. simultaneously) at the same time.

In some embodiments, the microfluidic device comprise a plurality of microchannels, wherein each microchannel has an inlet and at least one outlet. In some embodiments, the microfluidic device comprises at least about 10, or at about least 20, or at about least 30, or at about least 40, or at about least 50, or at about least 60, or at about least 70, or at about least 80, or at about least 90, or at about least 100, or at about least 120, or at about least 140, or at about least 150, or at about least 160, or at about least 180, or at about least 200, or at about least 220, or at about least 240, or at about least 260, or at about least 280, or at about least 300, or at about least 320, or at about least 340, or at about least 360, or at about least 380, or at about least 400 microchannels, or more than 400 microchannels or any integer between 10 and 400 microchannels. In some embodiments, the microfluidic device comprises at least about 32, or at least 48 or at least about 96, at least about 384 microchannels, or at least about 768 microchannels, or at least about 1536 microchannels or greater than 1536 micorchannels.

In general, the microchannel depth should be about 10-500 μm, preferably any range between about 10-250 μm including about 50-250 μm, most preferably about 10-20 μm in diameter. The thickness or width of the channel can be varied depending on the cell one is looking at. For example, from about 35 μm to about 300 μm, and all ranges in between. In some embodiments, the channel ranges from about 50 μm to about 250 μm. In some embodiments, a channel can be about 100 μm depth and between about 100 μm and about 200 μm in width or about 300 μm in width. In some embodiments, the depth of each microchannel is between 30 and 200 μm (e.g., between 30-175, 30-150, 30-125, 30-100, 30-75, 30-50, 30-40, 50-75, 50-100, 50-125, 50-150, 50-175, 50-200, 75-200, 100-200, 125-200, 150-200 or 175-200w, or between 200-300 μm). The microchannel should not be too large to prevent the need for high flow volumes, nor should the microchannel be too small to prevent clogging of the microchannel or inadequate focus. One of skill in the art can easily modify the microchannel diameter to suit their particular needs given the guidelines described herein.

In some embodiments, wells, herein referred to as sample wells can be prepared to introduce and collect samples at the ends of the channels. These can range from about 0.5 mm to about 2.0 mm, and all ranges in between, such as about 1.5 mm.

As shown in Example 3, in one embodiment the microchannels of the microfluidic device have flow focusing elements, such as vertical hydrodynamic focusing configuration to focus the flow, as disclosed in Cartas et al, 2009 (Lin A, et al., *Biomicrofluidics* 3, 014101-014112, 2009), which is incorporated herein in its entirety by reference. In some embodiments, flow focusing element is multiple crossing junctions, as disclosed in the Examples and shown in FIG. 5. In some embodiments, the flow focusing element is any configuration of the microfluidic channel which results in confining the particles (i.e. cells) in the sample into a single analytic layer of interest.

In some embodiments, the microchannels are compatible with automated pipettors for sample transfer (i.e. sample transfer to inlet sample wells or sample transfer from outlet sample wells (i.e. negative and positive sample wells)) of the microfluidic device. In some embodiments, the microchannels are configured using a three-dimensional micromachining method, such as a mechanically machined base/laminated cyclic polyolefin window, as disclosed in M. Cartas, PhD thesis, (which is incorporated herein by reference) that can be used for sample transfer in a second-generation microfluidic chip for use in the methods and line-imaging device as disclose herein with a different and/or strong flow focusing.

In some embodiments, the orientation and configuration of the plurality of microfluidic channels in the microfluidic device can be in any configuration, so long as each channel has a window or "analytical portion of" the microfluidic channel which can be scanned by the scanning detector. In some embodiments, the plurality of microfluidic channels are in parallel with respect to each other, but perpendicular with respect to the direction of scanning of the scanning detector.

Figure 8:
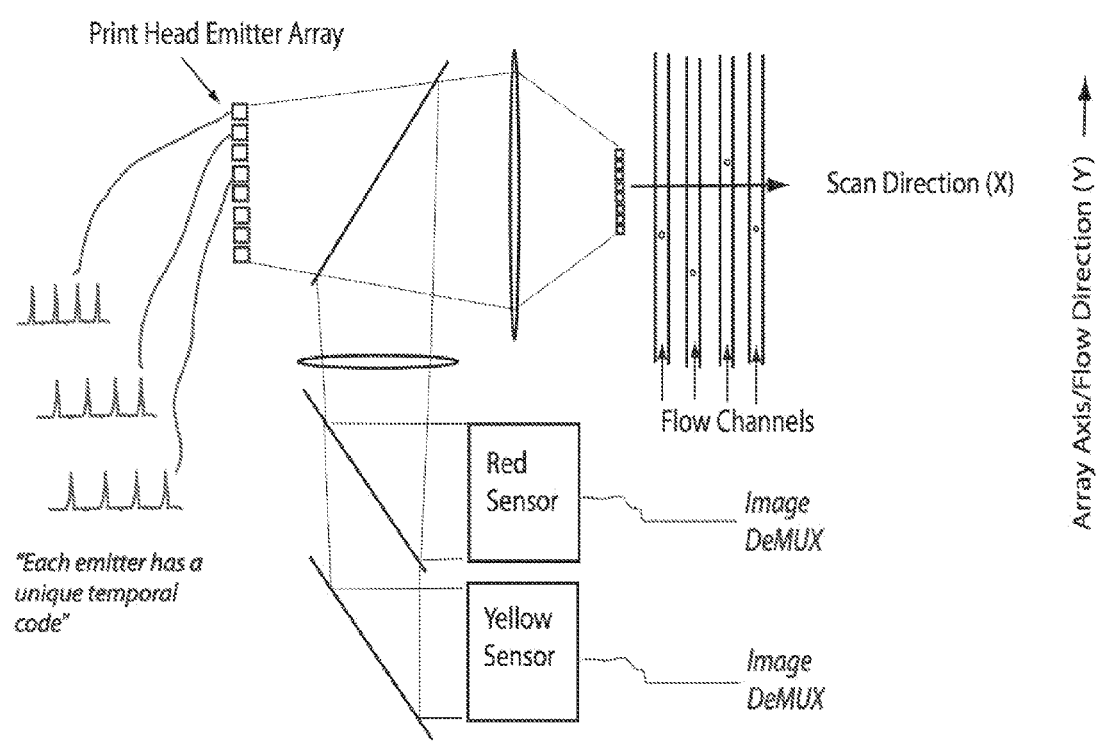
FIG. 8 is a schematic image of one embodiment showing a time-encoded multiplex point-source imaging. In such an embodiment, a linear-laser array, normally sold for printing applications is scanned transversely across the flow direction of the PMC microchannels. Each of the emitters is given a unique time-modulation code (idea borrowed from multiplexed optical communications). All of the induced fluorescence is gathered on a single detector (PMT) per color channel. A small (easily manipulated and stored) 2-D image can then be reconstructed by using the unique modulation codes of each source spot. This embodiment is compatible with the slit confocal detection and cascade detector (see FIG. 9, below).
Figure 10A:
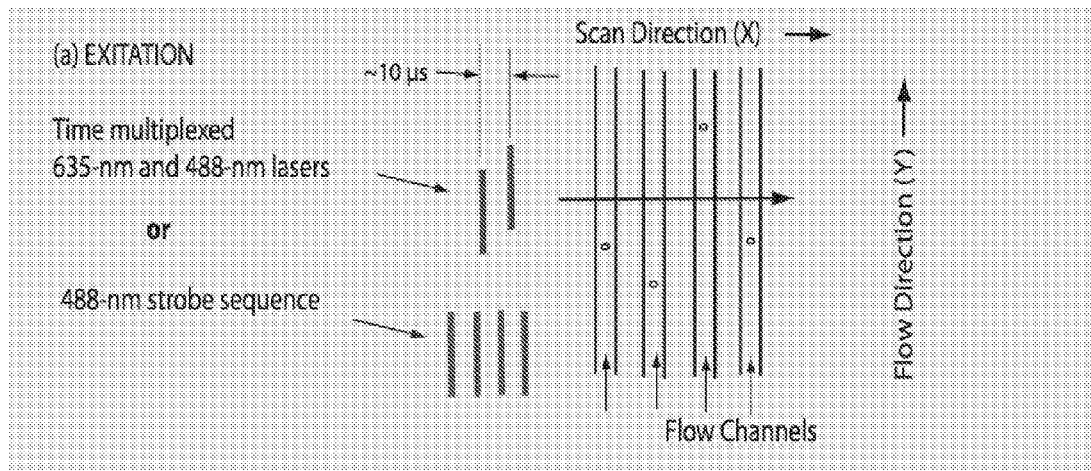
FIG. 10A-10B shows a schematic drawing of the introduction of multiple lasers by time-delay multiplexing (or strobe illumination).
Figure 10B:
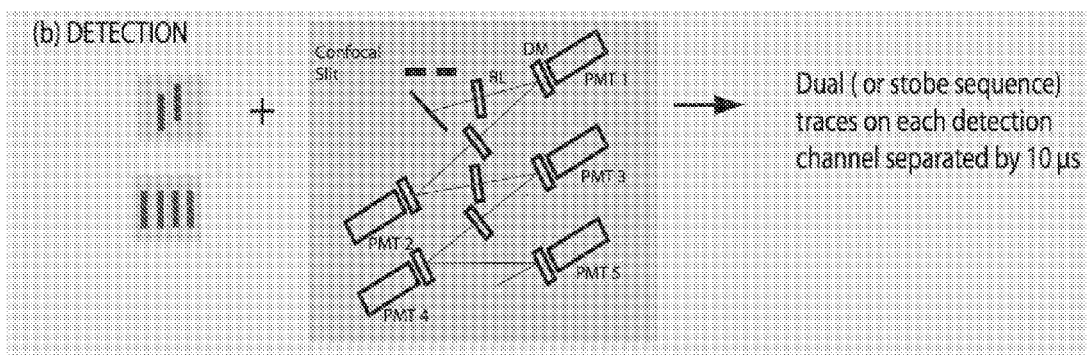

In some embodiments, each microchannel of the microfluidic device has "scanning window" or an "analytical portion of the microfluidic channel" through which the scanning detector can measure and record the emitted fluorescence from particles (e.g. cells) in the sample flowing through the microchannel. In some embodiments, the window is a portion of the surface of the microfluidic channel which is void of material which interferes with imaging by the scanning detector. Stated another way, each microchannel of the plurality of microchannels has a portion of the microchannel which allows the scanning detector to measure fluorescence of cells as they flow through the microchannel. Such "analytical portion of the microfluidic channel is also referred to as the "flow channel". In some embodiments, the flow channels of a plurality of microchannels are located in parallel of a plurality of microchannels also located in parallel, so the scanning device can measure multiple windows at the same time. In some embodiments, the orientation of the microchannels and flow channels are perpendicular to the direction of the scanning detector. In some embodiments, the microchannels, flow channels and flow duration is in on the Y-axis, and the scanning direction is in the X-axis, as shown in FIGS. 8 and 10.

In some embodiments, the scanning window is of sufficient length and diameter for a volume of sample of about at least 0.0001 µl to be scanned. In some embodiments, the scanning window is at least 50 µm, or at least 100 µm or at least 150 µm in length. In some embodiments, a scanning window of 100 µm in length allows for about 100 scans at 1 µm spacing along the linear length of the scanning window. In some embodiments, the scanning detector performs about 320 scans at 1 µm along the linear length of the scanning window.

In some embodiments, fluid flow rate of the sample through the microchannel, of through the scanning window is at least 10-20 µl/hour per channel.

In some embodiments, each microfluidic channel is configured with a microchannel junction, such as a Y-junction or a T-junction downstream of the scanning window. Sample fluid can flow into each arm of the Y or T junction based on positive and negative cell selection as disclosed herein. In some embodiments, the microfluidic channel can comprise a cell sorter component or switching component. This allows for cell sorting of the cells which were scanned in the scanning window. Any microswitch or valve which is commonly known in the art can be used to direct fluid flow at a microchannel junction. In some embodiments, the cell sorter is a piezoelectric microswitch, as disclosed in U.S. Pat. No. 6,262,519, which is incorporated herein in its entirety by reference. In some embodiments, the cell sorter component or switching is located on the microchannel downstream of the scanning window but before the Y-junction or T-junction. In some embodiments, the cell sorter component or switching is a valve, which is located on either or both arms of the Y-junction or T-junction. In some embodiments, the microswitch is controlled by the output of the storage device, such as a positive or negative cell selection output from the storage device, which directs fluid flow along the positive or negative arm of the Y- or T-junction respectively. In one embodiment, the detector determines the location of a fluorescent marker, for example, if the florescent marker is either in the cell cytoplasm or in the cell nucleus by comparing two or more different color channels. Based on that determination, the detector a signal to a piezo-electric element that activates if the cell is determined to be a rare "positive" (e.g., in some embodiments, a marker is detected in the nucleus). By way of example only, in some embodiments the activation causes the piezo-electric element to extend and, thereby, displacing the fluid volume in the microchannel that contains the "positive" cell into a side channel, where the side channel is fluidly connected to a collection chamber to collect the positively identified cells. In some embodiments, the cell sorter component can be used to positively select and isolate rare cells identified by image capture analysis after the cell has passed the scanning window of the microfluidic channel. In some embodiments, the system can be used to positively select rare cells in the sample, or alternatively, negatively select rare, or harmful cells in a sample (e.g., where the majority of the sample comprises healthy cells and a small percentage, e.g., >5%, or about 5%, or about 2%, or about 1%, or about 0.1% etc. are harmful cells, e.g., bacterial cells or, in some embodiments, unhealthy or cancerous or malignant cells). In some embodiments, the selected cells can be processed for further analysis or discarded where appropriate (e.g., in the case of unhealthy or harmful cells). In some embodiments, rare cells comprise about 0.1% cells or less than 0.1% of a total cell population.

The microfluidic device as disclosed herein can also be referred to as "chips". Microfludic chips can be configured by one of ordinary skill in the art to be any geometric shape and size, and are generally small and flat, typically about 1 to 10 inches square (25 to 250 mm square) or rectangles with dimensions of about 25 to 200 mm. The volume of sample flowing through the microfluidic chip will be small. For example, they will contain only about 0.1 to 10 µl for each assay, although the total volume of a specimen may range from 10 to 200 µl. The chambers holding the sample fluids and reagents typically will be relatively wide and shallow in order that the samples can be easily seen and changes resulting from reaction of the samples can be measured by suitable equipment. The interconnecting capillary passageways typically will have a cross-sectional dimension in the range of 1 to 2000 µm, preferably 200 to 500 µm. The shape will be determined by the method used to form the passageways but passageways having rectangular cross-sections are preferred. The depth of the passageways will be at least 5 µm in many practical applications where samples contain particles, but may be smaller where the nature of the sample permits.

While there are several ways in which the capillaries and chambers can be formed, such as injection molding, laser ablation, diamond milling or embossing, it is preferred to use injection molding in order to reduce the cost of the chips. Generally, a base portion of the chip will contain the desired network of chambers and capillaries. After reagent compounds have been placed in the chambers as desired, a top portion will be attached over the base to complete the chip.

In some embodiments, the chips can be disposable, and are intended to be disposable after a single use. Consequently, they will be made of inexpensive materials to the extent possible, while being compatible with the reagents and the samples which are to be analyzed. In many instances, the chips will be made of plastics such as polycarbonate, polystyrene, polyacrylates, or polyurethene, alternatively, they can be made from silicates, glass, wax or metal. In other instances the chips will be low-fluorescence glass, such as alumina-silicate glass, for example, Corning Corportion Eagle™ glass.

Types of Thermoplastic Materials for Substrates of the Microfluidic Devices and Remote-Valve Microfluidic Devices In some embodiments, the microfluidic chips as disclosed herein are made of plastic, and as such will be much cheaper than other microfluidic chips available in market which are made of glass or quartz.

Most currently available microfluidic devices are made of silicon and/or glass. Use of silicon and glass is relatively expensive because of high material and manufacturing costs. Polymeric materials would be less expensive. Therefore, microfluidic devices made from polymeric materials are more suitable for mass-production of disposable devices. In one embodiment, the microfluidic devices disclosed herein are made using cyclic polyolefin, such as ZEONEX® (ZEONEX 690R, Zeon Chemicals Inc. Louisville, Ky., USA). For example, the inventors demonstrated herein that the mechanical and optical properties of cyclic polyolefins, such as ZEONEX are suitable for on-chip cell lysis.

In some embodiments, the microfluidic device disclosed herein is made of thermoplastic polymer that includes a channel or a multiplicity of channels whose surfaces can be modified by photografting. In some embodiments, the device further includes a porous polymer monolith (PPM) impregnated with silica particles or carbon particles for cell lysis of a biological sample, as disclosed in International Patent Application WO2009/002580 (herein incorporated in its entirety by reference), where the PPM impregnated with silica or carbon particles can be prepared via UV initiated polymerization of a porous polymer solution embedded with the silica or carbon nanoparticles, within the channel.

In some embodiments, the monolith is formed by in-situ UV polymerization of a monomer mixture impregnated with for example, carbon particles. For example, one can use cyclic polyolefins. In one embodiment, the inventors demonstrated use of ZEONOR® or ZEONEX® (Zeon Chemicals, Louisville, Ky., USA), medical grade cyclic polyolefins, to manufacture a plastic microfluidic device. The inventors used ZEONEX® the primary chip material, because of its excellent mechanical properties, low auto-fluorescence and high UV transmission. However, one can use any other material with suitable optical properties can be used. The optical properties necessary for both photoinitiated polymerization during manufacturing and the integration of on-chip detection in the future include good mechanical properties, low auto-fluorescence and high UV transmission.

In one embodiment, one forms the microchannels by hot embossing with a master at about 100° C. (about 30° C. above the Tg of ZEONEX or ZEONOR) and about 250 psi for about minutes using, for example, a hot press, such as Heated Press 4386, Carver, Wabash, Ind. The master and the substrate can be manually separated at the de-embossing temperature, 60° C. Aluminum (Al) coating on the master facilitates easier removal of the master from the substrate after the embossing is completed. To seal the channels, another piece of ZEONEX or ZEONOR of the same dimensions can be thermally bonded on top, for example using 68° C., 250 psi, for 2 minutes.

In an alternative embodiment, one can prepare the microfluidic device as disclosed herein by hot embossing using wire embedded in the base plate of ZEONEX or ZEONOR substrate or by using a SU-8 master. Channels of about 100 µm and about 165 µm depths can be fabricated by this method. The width of the channels can vary from about 2 µm to at least about 500 µm. The width of the channels preferably vary from about 50 µm to about 250 µm or any width between, such as about 51 µm, or about 52 µm, or about 53 µm, about 54 µm, or about 55 µm, or about 60 µm, or about 65 µm, or about 70 µm, or about 75 µm, or about 80 µm, or about 85 µm, or about 90 µm, or about 100 µm, or about 115 µm, or about 125 µm, or about 150 µm, or about 200 µm, or about 249 µm. One can drill wells of any depth. In one preferred embodiment, one drills wells of about 1.5 mm diameter at the end of the channels for sample introduction and collection.

In some embodiments, where SU-8 master is used in fabrication of the device, the SU-8 masters can be fabricated, for example, on piranha-cleaned silicon wafers by spinning SU-850 photoepoxy (Microchem, Newton, Mass.) or any other comparable method. In one preferred embodiment, one uses thickness of about 100 µm and about 165 µm onto the wafers. One then pre-bakes the wafers as is known to one skilled in the art. For example, in one preferred embodiment, one pre-baked the wafers for 30 min at 95° C. After baking, the pattern is transferred through a mask preferably, by using contact lithography. Other applicable methods may be used as is known to one skilled in the art. One follows the transfer of the pattern by development, for example with SU-8 developer (Microchem) and post-baking the wafers for, for example, 1.5 h at 175° C. In one embodiment, after the fabrication process, the SU-8 molds exhibit glass-like mechanical properties and have the negative pattern of the microfluidic channels.

In some embodiments, the wafers are sputter coated with about 500 Angstroms (Å) of titanium (Ti) for adhesion, followed by about 1000 Å of Al. In another embodiment, one forms the microchannels by hot embossing with a master at about 100° C. (about 30° C. above the Tg of ZEONEX or ZEONOR) and about 250 psi for about minutes using, for example, a hot press, such as Heated Press 4386, Carver, Wabash, Ind. The master with and the substrate can be manually separated at the de-embossing temperature, 60° C. Aluminum (Al) coating on the master facilitates easier removal of the master from the substrate after the embossing is completed. To seal the channels, another piece of ZEONEX or ZEONOR of the same dimensions can be thermally bonded on top, for example using 68° C., 250 psi, for 2 minutes.

The capillary passageways will be adjusted to be either hydrophobic or hydrophilic, properties which are defined with respect to the contact angle formed at a solid surface by a liquid sample or reagent. Typically, a surface is considered hydrophilic if the contact angle of water on the surface is less than 90° and hydrophobic if the contact angle is greater than 90°. Preferably, the surface energy is adjusted by plasma induced polymerization at the surface of the passageways. The analytical devices of the invention may also be made with other methods used to control the surface energy of the capillary walls, such as coating with hydrophilic or hydrophobic materials, grafting, or corona treatments. The surface energy of the capillary walls may be adjusted for use with the intended sample fluid. For example, to prevent deposits on the walls of a hydrophobic passageway or to assure that none of the liquid is left in a passageway. For most passageways in the microfluidic devices of the invention, the surface is generally hydrophilic since the liquid tends to wet the surface and the surface tension forces causes the liquid to flow in the passageway. For example, the surface energy of capillary passageways is adjusted so that the contact angle of water on the surface is between 10° to 60° when the passageway is to contact whole blood or a contact angle of water on the surface of 25° to 80° when the passageway is to contact urine.

In order to design chips in which centrifugal force is applied to overcome hydrophilic or hydrophobic stops empirical tests or computational flow simulation can be used to provide useful information enabling one to arrange the position of liquid-containing chambers on chips and size the interconnecting capillary channels so that liquid sample can be moved as required by providing the needed force by adjusting the rotational speed.

Microfluidic devices can take many forms as needed for the analytical procedures which measure the analyte of interest. The microfluidic devices typically employ a system of capillary passageways connecting chambers containing dry or liquid reagents or conditioning materials. Analytical procedures may include preparation of a metered sample by diluting the sample, pre-reacting the analyte to ready it for subsequent reactions, removing interfering components, mixing reagents, lysing cells, capturing bio molecules, carrying out enzymatic reactions or incubating for binding events, staining, or deposition. Such preparatory steps may be carried out before or during metering of the sample, or after metering but before carrying out reactions which provide a measure of the analyte.

In such analytical procedures a sample will be combined with a conditioning liquid or with a reagent liquid and then transferred to a mixing chamber before being sent to subsequent processing. It will be evident that intimate mixing of the sample with the reagent or conditioning liquid is important to accurate and reproducible results. As is well known, the flow in microfluidic devices is typically laminar, that is, the viscosity of the liquid has a greater effect than the inertia of the flowing liquid so that the liquid flows linearly without being turbulent. One consequence of laminar flow conditions is that mixing of two or more liquids is slow since it principally results from molecular diffusion. As discussed above, some microfluidic devices have been designed to improve diffusion between layers of liquids in laminar flow. Many of these devices do not intend that complete mixing occurs, but in others provision for close contacting of liquid streams is provided.

The photografting method used in preparing the microfluidic chips of the present invention can be used for the surface modification of a wide range of thermoplastic polymers. The preferred substrates, i.e. for forming channel or tube surfaces, are selected from the group consisting of poly(methyl methacrylate), poly(butyl methacrylate), poly(dimethylsiloxane), poly(ethylene terephthalate), poly(butylene terephthalate), hydrogenated polystyrene, polyolefins such as, cyclic olefin copolymer, polyethylene, polypropylene, and polyimide. Polycarbonates and polystyrenes may not be transparent enough for efficient UV transmission and therefore may not be suitable for use as substrates.

Optical properties such as light transparency at the desired wavelength range and low background fluorescence are important characteristics of substrate materials that show potential for use in the microfluidic devices as disclosed herein. Since the photografting reactions must occur within the channels on all sides, the light must first pass through a layer of this polymer. Therefore, the substrate materials should be transparent in a wavelength range of about 200 to about 650 nm, preferably at any point in the range between about 230-330 nm such as about 250 to about 300 nm, or about 260 to about 295, or about 300 nm-400 nm or about 400-500 nm or about 500-600 nm or about 600-650 nm etc.

In addition, the chemical properties and solubility of substrates can be taken into consideration. For instance, substrates that dissolve only in solvents, such as toluene and hexane, that are less likely to be used in standard microfluidic applications, make more desirable candidate substrate materials for photografting.

One important consideration in choosing substrate material for grafting is the grafting efficiency, expressed as Neff, of the monomer to the substrate, which depends on properties such as the chemistry and transparency for light at the desired wavelength range. Grafting efficiency values of substrates correlate well with the irradiation power, the measured values of contact angles and the transparency of the substrate. An opaque substrate with a grafting efficiency value of 0 would reflect a sample, wherein no transmitted light can be detected using the material as a filter and no grafting is achieved even after 30 minutes of irradiation.

Thickness of only a few micrometers of a UV absorbing material or solution could decrease the intensity of the UV light and, consequently, the grafting efficiency. The depth of features in typical microfluidic devices may reach several tens of micrometers. Therefore, it is important to assess the effect of UV transparency of the grafting monomer mixtures during the grafting more exactly in order to determine the depth of the channel through which sufficient grafting can be safely achieved with the chosen monomer mixture.

In general, the channel depth should be about 10-500 μm, preferably any range between about 10-250 μm including about 50-250 μm, most preferably about 10-50 μm. The thickness or width of the channel can be varied depending on the biomolecule one is looking at. For example, from about 35 μm to about 300 μm, and all ranges in between. In some embodiments, the channel ranges from about 50 μm to about 250 μm. In some embodiments, a channel can be about 100 μm depth and between about 100 μm and about 150 μm in width.

In some embodiments, wells can be prepared to introduce and collect samples at the ends of the channels. These can range from about 0.5 mm to about 2.0 mm, and all ranges in between, such as about 1.5 mm.

Other plastics can be used for the microfluidic devices, in particular the substrate for he remove-valve microfluidic device using for example, a variety of commercially available materials known by a skilled artisan such as, for example, polymethyl-methacrylate (PMMA), polystyrene (PS), polycarbonate (PC), polypropylene (PP), or polyvinylchloride (PVC). Other representative materials that can be used to fabricate upper and lower substrates 21, 22 include, but are not limited to polychlorotrifluoroethylene (PCTFE), polyetheretherketone (PEEK), polyetherimide (PEI), polyethersulfone (PES), polyethylene—carbon filled (PE), polyethylene—high density (HDPE), polyethylene—low Density (LDPE), polyethylene—U.H.M.W. (UHMW PE), polyethylene naphthalate (PEN), polyethylene terephthalate (polyester, PET, PETP), polyethylene/polyethylene composite (PE fibre—PE matrix), polyhydroxybutyrate—biopolymer (PHB), polyhydroxybutyrate/polyhydroxyvalerate 8%—biopolymer (PHB92/PHV 8), polyhydroxybutyrate/polyhydroxyvalerate 12%—biopolymer (PHB88/PHV12), polyimide (PI), polymethylpentene (TPX®), polyoxymethylene—copolymer (acetal—copolymer POMC), polyoxymethylene—homopolymer (acetal—homopolymer POMH), polyoxymethylene/acetal copolymer—10% carbon fiber reinforced (POMC-10% CFR), polyphenyleneoxide (PPO modified, PPE modified), polyphenyleneoxide (modified), polyphenylenesulfide (PPS), polyphenylenesulfide—40% glass fiber reinforced (PPS-40% GFR), polyphenylene-sulphide—20% carbon fiber reinforced (PPS-20% CFR), polyphenylsulfone (PPSu), polypropylene (PP), polypropylene—polypropylene composite (PP fibre—PP matrix), polystyrene (PS), polystyrene—conductive (High Impact Conductive Polystyrene), polystyrene—cross-linked (PS—X-Linked), polystyrol, polysulphone (PSu), polytetrafluoroethylene (PTFE), polytetrafluoroethylene coated Glass Fabric (PTFE 75/Glass 25), polytetrafluoroethylene filled with glass (PTFE 25% GF), polyvinylchloride—unplasticized (UPVC), polyvinylfluoride (PVF), polyvinylidenechloride (PVDC), and polyvinylidenefluoride (PVDF). See, for example, product catalogs offered by Goodfellow Cambridge Limited, Huntingdon, Cambridgeshire, England. In the case of optical characterization, the substrate is preferably constructed out of a transparent plastic material.

Capillaries, reaction chambers, and pump chambers can be formed in substrates using methods such as injection molding, compression molding, hot embossing, machining, micro-compression molding, electrodischarge machining, injection compression molding, hot stamping, and micro injection molding. Methods for forming the features in the microfluidic devices include die cutting, die forging, blow molding, rotary die cutting, laser etching, injection molding, and reaction injection molding.

Scanning Detector

The scanning detector for use in the line-scan device as disclosed herein can comprise a 1-D or a 2-D line imaging scanning. In some embodiments, the scanning device is a 1-D line imaging system to produce at least one 5×1 1-D image of each particle (e.g. cell) as it flows through the scanning window of the microchannel. In some embodiments, the scanning device is a low-complexity 2-D line imaging system, which produces a 5×5 2-D image of each particle (e.g. cell) as it flows through the scanning window of the microchannel. The scanning detector is capable of generating at least one 1-D or 2-D line image for each particle (i.e. cell) in a series of particles (i.e. cells) as they flow through the microchannel. As there are a plurality of microchannels in the microfluidic device, the scanning detector is configured to produce a 1-D or low complexity 2-D line image of each particle (i.e. cell) as in a series of particles in each microchannel of the plurality of microchannels of the microfluidic device.

In some embodiments, a scanning detector is a single channel cytometer. In some embodiments, the scanning detector is parallel microfluidic cytometer (PMC) as disclosed herein, and in McKenna et al., Lab Chip, 2009; 9; 305-310, which is incorporated herein in its entirety by reference. In some embodiments, one of ordinary skill in the art can use a single channel cytometer (i.e., FACS) as a scanning detector by increasing the spatial resolution of the fixed detector, adding a scanner and adding a linear array and strobe illuminator.

In some embodiments, the scanning detector is configured to record emitted fluorescence from the plurality of microchannels in the microfludic device. In particular, the scanning detector is moving in the direction of the flow of fluid along the microchannel, and recording emitted fluorescence at every 1 μm across the scanning window. In some embodiments, where the scanning window is 100 μm in length, scanning detector measures the emitted fluorescence at every 1 μm in the 100 μm window. In some embodiments, the scanning detector moves about 1 μm every ¹⁄₁₀₀ of a second. In some embodiments, the scanning detector moves about 0.5 μm, or 1 μm, or 2 μm, or 3 μm or 5 μm or 10 μm every ¹⁄₁₀₀ of a second. In some embodiments, the scanning detector moves about 0.5 μm, or 1 μm, or 2 μm, or 3 μm or 5 μm or 10 μm every 0.1, or 0.2 or 0.5 $100^{th}$ of a second, or about every 2, 3, 4, or 5 100th of a second.

In some embodiments, the scanning detector comprises a variety of different lasers, for example, at least about 2, or 3, or 4, or 5 or 6 or 7 or more different lasers emitting different wavelengths. In some embodiments, the scanning detector can comprise 2 different lasers, such as lasers for red and green fluorescence respectively. In some embodiments, the any laser or combination of lasers for excitation at 488 nm, 405 nm, 633 nm, 543 nm and deep-UV are used in the scanning detector. In one embodiment, the scanning device comprises lasers at 488-nm and 405-nm and 633-nm in order to be optimized for GFP, the Cellomics nuclear translocation kit, and Luminex beads. Also encompassed are use of additional lasers for excitation at 543-nm, and the deep-UV.

In some embodiments, where the scanning detector comprises more than 2 different lasers, the scanning detector is referred to herein as a multisource scanning detector. In such embodiments, pulsed (e.g. femtosecond) sources can be used. In some embodiments, stimulated emission imaging and multiphoton imaging can be performed. In some embodiments, the scanning detector comprises a multi-laser excitation on an photomultiplier cascade.

In some embodiments, the scanning detector can measure a variety of different wavelength, for example, at least about 2, or 3, or 4, or 5 or 6 or 7 or more different wavelengths. In some embodiments, the scanning detector can detect 2 different wavelengths, such as wavelengths for red and green color fluorescence respectively.

Those skilled in the art will recognize a wide variety of ways to measure fluorescence. For example some fluorescence reporter molecules exhibit a charge in excitation or emission spectra, some exhibit resonance energy transfer where one fluorescent reporter decreases in fluorescence, and another marker increases in fluorescence, some exhibit loss (quenching) or appearance of fluorescence. All means to measure fluorescence is encompassed in the scanning detector, including FACS, as well as fluorescence correlation spectrometry (FCS).

In some embodiments, each wavelength is detected by a single-cathode photomultiplier tube (PMT). In alternative embodiments, multi-cathode PMTs can be used, or avalanche photodiode arrays (APDs) can be used for detecting different wavelengths. In some embodiments, the scanning detector comprises a multi-laser excitation with an expandable PMT cascade. In some embodiments, a modified galvanometer-based scanner (i.e. from General Scanning, CRS and M-series) is used as a scanning detector as disclosed herein in the Examples. In some embodiments, a one-dimensional galvanometer-based scanner comprises a multi-laser excitation, an expandable PMT cascade and a slit-confocal stray light rejection device. In some embodiments, a scanning detector can comprises 5 PMTs for two lasers (red and green) which can scan at least 32 scanning windows of the microchannels. In some embodiments, a scanning detector can detect 8 colors and comprises at least 8 PMTs for four lasers which can scan at least 32 scanning windows of the microchannels. Scanning of 32 windows takes for example, only about 10 ms or shorter time. In some embodiments, a cascade detector channels are easily customized by changing out the dichroic beam splitters and band-pass filters. Two channels will be optimized as "backscatter" (whole-cell) signals at the two laser wavelengths; two additional channels will be initially optimized at the GFP and nuclear-stain channels. A transmitted-light (forward scatter) channel can be added by one of ordinary skill in the art.

In some embodiments, the PMTs has a spot resolution of about 0.5-5 μm for a cell about 10 μm in diameter. In some embodiments, the PMT has a spatial resolution of about 0.5-1 μm. In some embodiments, the PMT has a spatial resolution of about 1 μm. In some embodiments, the PMT has a spatial-resolution spot size of about 2-4 μm. In some embodiments, the PMT has a resolution of about 3.5 μm.

In some embodiments, the dimension of the detection volume (as detected by the detector) parallel to the scan direction is between 1 and 5 μm (e.g., at least 1, at least 2, at least 3, at least 4, at least 5 μm). In one embodiment, the laser spot geometry is elliptical (e.g., 3 μm by 50 μm).

In some embodiments, the scanning detector has a spot size of between 3-4 μm, for example a spatial resolution spot size of 3.5 μm. In some embodiments, a large laser spot size is used (e.g., 30×100 microns, or 30×30 microns). Such a large laser spot size can be used for high throughput sorting of larger cells, or for a high sensitivity to rare cells. In some embodiments, a larger spot size will decrease the focus and clarity of the image, and can be useful to identify larger cells or rare cells. In some embodiments, the spatial resolution spot size can be determined by the user to identify a cell type of a specific size. For example, in some embodiments, the spatial resolution spot size can identify cells within the range of 1-50 µm, for example a spatial resolution spot size of 3.5 µm can be used to identify cells of about 10 µm, or a spatial resolution spot size of about 4-5 µm can be used to identify a yeast cell of about 6 µm in diameter, or a spatial resolution spot size of about 1-3.5 µm can be used to identify cells about 1 µm, such as bacterial cells, or a spatial resolution spot size of about 3.5-5 µm can be used to identify cells about 50 µm such as heart cells and neurons. In some embodiments, the spatial resolution spot size can be adjusted accordingly to identify cells of about 3-15 µm in diameter, or between about 3-20 µm in diameter, or between about 1-10 µm in diameter, or cells about 20-50 µm in diameter, or cells greater than about 50 µm in diameter. In some embodiments, the spatial resolution spot size is adjusted so it allows enough resolution of the cell to see markers and/or internal structures of the cell and resolve details inside the cells yet being quick enough for quick image capture for high throughput analysis.

In some embodiments, the PMT of a scanning detector has a detection diameter of between 1 µm-5 µm, such as, for example 3.5 µm. In some embodiments, the detection spot can be of a variety of geometric conformations as it intercepts with the surface area of the microchannel or axial to the longitudinal length of the microchannel or with the particle, and in some embodiments, the detection spot is circular, or elliptical, or oval, oblong, triangular, or an asymmetric conformation and the like. Stated another way, where the detection spot is circular, the diameter of the spot can be between 1-5 µm, e.g., in some embodiments 3.5m, e.g., in some embodiments 3.5 µm. In alternative embodiments, where the detection spot is elliptical, the longer diameter of the elliptical spot can be between 1-5 µm, and where the longer diameter is axial or parallel to the longitudinal length of the microchannel, such that the longer diameter of the eclipse is parallel to the scan direction of the PMT.

In some embodiments, a PMT of a scanning detector provides about 4-10Y pixels per scan. One of ordinary skill in the art can determine the optimal spatial resolution settings and optimal number of PMTs for particles of different sizes (i.e. cells) using synthetic fluorescent beads of different shapes and sizes as disclosed herein in the Examples (see Example 2).

In some embodiments, the scanning detector uses low-complexity 2D-line image scanning In such embodiments, there are independent wavelength sources, and each color channel for each source (i.e. red and green signals from red and green sources) are detected on a single detector and are subsequently de-multiplexed, which is a time-encoded image for subsequent cell identification. As disclosed in Example 2, one embodiment of a low-complexity 2-D line imaging scanning system uses a time-multiplexed imaging system using a 22-emitter array at 630-650 nm wavelength which was demagnified to 2 µm resolution to result in a 5×5 pixel image for a 10 µm diameter cell.

In some embodiments, the 1-D or low complexity 2-D line images are 10 line images of the particle (i.e. cell). However, other line images are encompassed, for example 1-D or low complexity 2-D line images which are 5 line, or 7 line or 8 line or 12 line, or 15 line or 20 line images, or any image between 5 and 20-line images. In some embodiments, more than 20-line images are encompassed for analysis in the line-scan image device as disclosed herein. In some embodiments, 10 different images of the particle (i.e. cell) make up the 10 line image In some embodiments, the particle (i.e. cell) imaged by the scanning detector is at least 5 µm, or at least about 10 µm. The particle (i.e. cell) can be of any shape and diameter, for example, spherical, irregular shaped, rod-shaped, oval, disc-shaped, concave, convex etc. In some embodiments, the particle can be of any diameter, for example between 1-50 µm in diameter or an size inbetween 1-200 µm, such as at least 1 µm, or at least 5 µm, or about 10 µm in diameter, or about 20 µm, or about 30 µm, or about 40 µm, or about 50 µm in diameter. In some embodiments, the particle size can be between 50-200 µm in diameter, for example about 60 µm, or about 70 µm, or about 80 µm, or about 90 µm, or about 100 µm, or about 120 µm, or about 150 µm, or about 180 µm, or about 200 µm, or greater than 200 µm in diameter. In some embodiments, the methods and devices as disclosed herein can be optimized so that the spot size is adjusted to image a rare cell, e.g., a cell of >50 µm in diameter. In some embodiments, the spot size of the detector can be 30×100 µm or 30×30 µm for high throughput and high sensitivity of rare cells. Such imaging of rare cells is useful to identify rare cells in a population of cells in a biological sample from a subject, e.g., a mammalian subject or a human subject, for example, in a clinical analysis or assay to identify a rare cell disorder or disease and the like.

The scanning detector is configured to produce 1-D or low complexity 2-D line images of sufficient resolution for running the image through a cell-type algorithm to identify cell features as disclosed in Table 1. In some embodiments, the cell feature is protein localization, and in some embodiments, the cell feature is intracellular organelle localization or morphology. In some embodiments, the scanning detector is configured to produce 1-D or low complexity 2-D line images of sufficient resolution for running the image through a cell-type algorithm to identify cell features. In some embodiments, the detector is used to determine protein localization and/or the location of one or more fluorescent markers, e.g., if a protein or fluorescent marker is located in a specific compartment of the cell. For example, in a nuclear translocation assay, which is well-known to persons of ordinary skill in the art a marker, such as a fluorescent marker moves between the cytoplasm and the cell nucleus depending on chemical stimulation. In another embodiment, the detector images the whole cell or a microscopic bead, and determines identity of the cell through color ratios without the need to discriminate the intracellular location of the fluorescence marker internal within the cell. One such example of this embodiment is use of the system and device as disclosed herein in an assay using "bar-coding", where discrete color ratio's on chemically functionalized polymer beads such as LUMINEX™ 100 beads from Invitrogen, and as disclosed in U.S. Pat. No. 7,764,361 (which is incorporated herein in its entirety by reference) are detected by the detector. In such an embodiment, one more color channels are used to encode the chemical identity of the bead, and these channels are read by the detector simultaneously with at least one other color channel, to determine the assay information of the cell and/or a cell lysate. In some embodiments, this method can be multiplexed such that each microfluidic channel carries more than one bead type. In some embodiments, the beads are internal to the cell. In other embodiments, the bead are external to the cell, and flow simultaneously along the microfluidic channels with the cells being assays as a way to identify the source and/or cell lysate of the cells.

Time Multiplexing of Laser Scan: Two (or more) laser beams are introduced as separated spots on the scanning windows of the microchannel (see FIG. 10) but sufficiently adjacent so that both spots will sequentially scan though individual cells. In some embodiments, the time delay will be on the order of 10 vs, so at a typical scan, sample flow through the microchannel results in the particle (i.e. cell) moving several microns or less between laser spots. The spots can be vertically (Y-dimension) displaced to compensate for movement, or with elongated laser spots (FIG. 10), no displacement is necessary.

In another variant of time multiplexing a temporally separated series of (ideally) identical multi-color ("strobe") images can be created by sending several reflections of a single-laser wavelength through the scanner. This is most easily done by using a parallel stack of partial reflectors. For example to get an off-set series of 4 images from a 488-nm laser, two microscope slides are used in reflection at 45 degrees in the illumination path (see FIG. 10). The four images from the four scanned beams can then be used to produce an "averaged" as opposed to "integrated" image. This is a standard way to separate background structure in noisy images.

Objective Lens: Any suitable objective lens can be used in the scanning device. In some embodiments, numerical aperture, working distance and field size is taken into account. In some embodiments, the Optem Inc. 10×, 0.5 NA long-working-distance microscope objective is used.

Image Analysis System, Processing and Analysis

In some embodiments, the data collected from the line scan imagining device, or the detector will be processed in an image analysis output device, such as for example, an analogue-to-digital convertor (ADC) to produce a 16-bit value. Typically, in some embodiments 80-pixels are produced for each microchannel.

In some embodiments, 10-line images of the particles (i.e. cells) from the scanning detector are produced from 16-bit values. These can be analyzed by a variety of different image analysis software tools, for example but not limited to MatLab, MetaMorph, ImagePro and Axiovision. Alternatively, image analysis can be performed using shareware 2-D image analysis software including ImageJ/NIH and CellProfiler. In some embodiments, the image output device is connected to a storage device.

Cell-type Algorithm and Construction of Phenotypic Signatures.

In some embodiments, the data is filtered or specific parameters of the cell-type algorithm are adjusted for specific cell types or particular experimental paradigm (i.e. such as protein subcellular localization experiments etc). Cell type is determined on a number of factors including In some embodiments, a comparison module as disclosed herein, compares at least one line scan image, or a least 2, or 3, or 4, or 5, or 6, or 7 or 8 or 9 or a least 10 line image scans of the cell with a reference point indicating a cell phenotype. In some embodiments, the reference point indicating a cell phenotype is a reference line scan image of cell phenotype. In alternative embodiments, the reference point indicating a cell phenotype is a value from an algorithm indicating a cell phenotype.

In some embodiments, the comparison module is configured to analyze at least one line-scan image or a plurality of line scan images from each cell by comparison with a reference line scan image, and wherein if the line-scan image of the cell has substantially similar cell features, such as those in listed in Table 1.

In some embodiments, the comparison module is configured to analyze a line-scan image, or a plurality of line-scan images of a cell via a cell-typing algorithm, and wherein the identity of cell type via the cell type algorithm triggers or de-selects switching of the piezoelectric microswitch in the microchannel in which the cell was scanned, enabling selection of the cell.

In some embodiments, a line image of a cell identifies the cell as a positive cell or a negative cell by comparison of the line image of the cell with at least one reference point. In some embodiments, a line image of a cell is identified as a positive cell or a negative cell using a cell-type algorithm.

Storage Device

In some embodiments, the image information determined in the scanning detector can be read by the storage device. As used herein the "storage device" is intended to include any suitable computing or processing apparatus or other device configured or adapted for storing data or information. Examples of electronic apparatus suitable for use with the present invention include stand-alone computing apparatus; communications networks, including local area networks (LAN), wide area networks (WAN), Internet, Intranet, and Extranet; and local and distributed processing systems. Storage devices also include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon sequence information or expression level information. The data are typically provided in digital form that can be transmitted and read electronically, e.g., via the Internet, on diskette, or any other mode of electronic or non-electronic communication.

Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, other types of volatile and non-volatile memory, any other medium which can be used to store the desired information and which can be accessed by a computer, and any suitable combination of the foregoing. The computer readable media does not encompass a data signal or a carrier wave, preferably the computer readable medium is of physical form.

In some embodiments of this aspect and all other aspects of the present invention, a computer readable media can be any available media that can be accessed by a computer. By way of example, and not a limitation, computer readable media may comprise computer storage media and communication media.

As used herein, "stored" refers to a process for encoding information on the storage device. Those skilled in the art can readily adopt any of the presently known methods for recording information on known media to generate manufactures comprising the sequence information or expression level information.

In some embodiments of this aspect and all other aspects of the present invention a variety of software programs and formats can be used to store the phosphorylation information or expression level information on the storage device. Any number of data processor structuring formats (e.g., text file or database) can be employed to obtain or create a medium having recorded thereon the sequence information or expression level information.

In some embodiments of this aspect and all other aspects of the present invention, the image data stored in the storage device is data obtained from the scanning detector of the biological sample passing through the microchannel of the microfluidic device. In some embodiments, the image data is reference image data, from stored line-scan images of reference cells or reference cell phenotypes. Alternatively, the image data is reference data from a database, e.g., line-scan images of CCD images from known databases, such as BU or MIT. In one embodiment the image data is reference data or models that are indicative of a specific cell, cell phenotype, cell feature such as those disclosed in Table 1 cell, protein localization etc. In one embodiment, the image data is reference data of a cell with characteristic subcellular protein localization, presence of red and/or green dye, nucleus area and/or shape, cytoplasm area and/or shape etc.

Comparison Module

The image information which was converted from a 16-bit digital value into a 10-line image in the storage device can be further analyzed. Such analysis can be performed in the storage device, or alternatively in a comparison module. In some embodiments, the comparison module runs 10 line images through a cell-typing algorithm to identify features as listed in Table 1. In some embodiments, the value obtained from processing the line image through a cell-typing algorithm is compared to a reference value indicating a cell phenotype.

Alternatively, in another embodiment, one can directly compare the line images (i.e. 10 line image) information in a comparison module to compare a specific 10-line image with a reference value indicating a cell phenotype. In some embodiments, the reference value is stored on the storage device and/or the comparison module. For example, search programs can be used to identify relevant reference data the phenotype or specific cell feature as disclosed in Table 1 that matches a particular desired cell phenotype. The comparison made in computer-readable form provides output data which can be processed by a variety of means.

In some embodiments of this aspect and all other aspects of the present invention, the "comparison module" can use a variety of available software programs and formats for the comparison operative to compare 10-line image information determined from the scanning detector to reference data or to identify features as listed in Table 1, for example by using a cell-typing algorithm. In one embodiment, the comparison module is configured to use pattern recognition techniques to compare 10-line image information from one or more entries (i.e. cells) to one or more reference image patterns, such as those listed in Table 1. The comparison module may be configured using existing commercially-available or freely-available software for comparing patterns, and may be optimized for particular data comparisons that are conducted.

In some embodiments of this aspect and all other aspects of the present invention, the comparison module, or any other module of the invention, may include an operating system (e.g., UNIX) on which runs a relational database management system, a World Wide Web application, and a World Wide Web server. World Wide Web application includes the executable code necessary for generation of database language statements [e.g., Standard Query Language (SQL) statements]. Generally, the executables will include embedded SQL statements. In addition, the World Wide Web application may include a configuration file which contains pointers and addresses to the various software entities that comprise the server as well as the various external and internal databases which must be accessed to service user requests. The configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

In some embodiments of this aspect and all other aspects of the present invention, a comparison module can define instructions, for example, as part of one or more programs, that, as a result of being executed by a computer, instruct the computer to perform one or more of the functions described herein (e.g., trigger select or deselect an element of the cell sorter), and/or various embodiments, variations and combinations thereof.

In some embodiments, such instructions may be written in any of a plurality of programming languages, for example, Java, J, Visual Basic, C, C#, or C++, Fortran, Pascal, Eiffel, Basic, COBOL, etc., or any of a variety of combinations thereof. The comparison module can comprise computer-readable media on which such instructions are embodied may reside on one or more of the components of either of either the storage device or the comparison module as described herein, may be distributed across one or more of such components, and may be in transition there between.

In some embodiments of this aspect and all other aspects of the present invention, a computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a processor to implement aspects of the present invention. The computer executable instructions may be written in a suitable computer language or combination of several languages. Basic computational biology methods are described in, e.g. Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

Instructions can be provided to the computer systems refers to a number of computer-implemented steps for either (i) processing information in the system (i.e. running the data from the scanning detector through the cell-type algorithm) or (ii) selecting or deselecting a microswitch for cell sorting. Instructions can be implemented in software, firmware or hardware and include any type of programmed step undertaken by modules of the electronic financing system. The computer system can be connected to a local network. One example of the Local Area Network may be a corporate computing network, including access to the Internet, to which computers and computing devices comprising the financing system are connected. In one embodiment, the LAN conforms to the Transmission Control Protocol/Internet Protocol (TCP/IP) industry standard. Transmission Control Protocol Transmission Control Protocol (TCP) is a transport layer protocol used to provide a reliable, connection-oriented, transport layer link among computer systems. The network layer provides services to the transport layer. Using a two-way handshaking scheme, TCP provides the mechanism for establishing, maintaining, and terminating logical connections among computer systems. TCP transport layer uses IP as its network layer protocol. Additionally, TCP provides protocol ports to distinguish multiple programs executing on a single device by including the destination and source port number with each message. TCP performs functions such as transmission of byte streams, data flow definitions, data acknowledgments, lost or corrupt data re-transmissions, and multiplexing multiple connections through a single network connection. Finally, TCP is responsible for encapsulating information into a datagram structure.

In alternative embodiments, the LAN may conform to other network standards, including, but not limited to, the International Standards Organization's Open Systems Interconnection, IBM's SNA, Novell's Netware, and Banyan VINES. The computer system may comprise a microprocessor. A microprocessor may be any conventional general purpose single-or multi-chip microprocessor such as a Pentium processor, a PentiumX Pro processor, a 8051 processor, a MISS, processor, a Power PC processor, or an ALPHAZ processor. In addition, the microprocessor may be any conventional special purpose microprocessor such as a digital signal processor or a graphics processor. The microprocessor typically has conventional address lines, conventional data lines, and one or more conventional control lines.

In some embodiments, the computer system as described herein can include any type of electronically connected group of computers including, for instance, the following networks: Internet, Intranet, Local Area Networks (LAN) or Wide Area Networks (WAN). In addition, the connectivity to the network may be, for example, remote modem, Ethernet (IEEE 802.3), Token Ring (IEEE 802.5), Fiber Distributed Datalink Interface (FDDI) or Asynchronous Transfer Mode (ATM). Note that computing devices may be desktop, server, portable, hand-held, set-top, or any other desired type of configuration. As used herein, an Internet includes network variations such as public internet, a private internet, a secure internet, a private network, a public network, a value-added network, an intranet, and the like.

The computer systems and comparison module can use a variety of operating Systems. For example the computer system can be used in connection with various operating systems such as: UNIX, Disk Operating System (DOS), OS/2, Windows 3. X, Windows 95, Windows 98, and Windows NT. The computer system 150 as described herein can be programmed in any programming language, for example the system may be written in any programming language such as C, C++, BASIC, Pascal, Java, and FORTRAN and ran under the well-known operating system. C, C++, BASIC, Pascal, Java, and FORTRAN are industry standard programming languages for which many commercial compilers can be used to create executable code.

In one embodiment of the invention, the computer system can comprise a pattern comparison software can be used to determine cell-type phenotype. In some embodiments of this aspect and all other aspects of the present invention, a comparison module provides computer readable data that can be processed in computer readable form by predefined criteria, or criteria defined by a user, to provide a retrieved content that may be stored and output as requested by a user using a display module.

In some embodiments of this aspect and all other aspects of the present invention, the retrieved content can be the number of cells or % of cells in each microchannel of the microfluidic device with a particular cell phenotype etc. as well as the efficiency of sorting the cells into pre-defined selected cell phenotypes. In one embodiment, the retrieved content is a positive or negative selection of cells in each microchannel of the microfluidic device.

Display Module

In some embodiments of this aspect and all other aspects of the present invention, the line-image scanning device is optionally connected a display module. In some embodiments, analysis of the cells by the scanning detector or results from the comparison module can be displayed on a display module such as a computer monitor. In one embodiment of the invention, the analysis of the cells by the scanning detector or results from the comparison module is displayed through printable media. The display module can be any computer adapted for display of computer readable information to a user, non limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD), or any other type of processor. Other displays modules include; speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc In some embodiments of this aspect and all other aspects of the present invention, a World Wide Web browser is used for providing a user interface for the line-scan imaging device or access to the analysis of the cells by the scanning detector or results from the comparison module. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars, etc. conventionally employed in graphical user interfaces. The requests so formulated with the user's Web browser are transmitted to a Web application which formats them to produce a query that can be employed to extract the pertinent information related to the cell sorting, (i.e. selection of cells based on a cell phenotype) etc.

High Content Screening (HCS) Modules

In some embodiments, the line-imaging module can be configured to receive samples from a high content screen module, such as a flow cytometer module, e.g. a parallel microfluidic cytometer (PMC module) such as a 384-well flow cytometer as disclosed herein. Accordingly, the present invention relates to methods for analyzing cell (or other components in a sample), by first sorting the cells using a high-throughput flow cytometer and then further sorting the cells based on phenotype using the line-imaging module. Such a system is referred to herein as a "parallel flow FACS-line scan imaging system".

In some embodiments, the line imaging module can be further configured to be connected to a second high content screening module, such as a high throughput analysis module which performs PCR analysis, such as, for example a module which can perform multiplex quantitative PCR (multiplex QPCR), referred to herein as a "multiplex QPCR module".

A. Flow Cytometer Module

As discussed herein, the present invention the line-scan imaging device can be configured to receive samples from a flow cytometer, such as a parallel microfluidic cytometer (PMC module) such as a 384-well flow cytometer as disclosed herein.

Flow cytometers which can be connected to the line-scan imaging module can be, for example, (i) a conventional single-channel cytometer or (ii) a parallel microfluidic cytometer (PMC). For a single-channel cytometer, line-scan imaging could be accomplished by simply pushing up the spatial resolution of the fixed detector (assuming very good flow velocity controls), by adding a scanner, by adding a linear array and strobe illumination, or temporal encoding. As shown in the Examples, a PMC (rather than single-channel) flow cytometer architecture is preferable a parallel imaging system. Additionally, the PMC has potential for time-synchronized cytometry and down-stream expression analysis, well beyond the capabilities of single-channel FACS.

In some embodiments, the line-scan imaging device can be configured to receive samples from a PMC flow cytometer, such as disclosed in McKenna et al., Lab Chip, 2009, 9; 305-310, which is incorporated herein by reference. In such an embodiment, the inlet of each microchannel on the microdevice is in fluid communication with the output of the 384 well from the 384-well PMC device. This, in some embodiments, the line-scan imaging device can be used to sort cells based on cell phenotype following cell separation based on FACS analysis (i.e. based on size and expression of fluorescent markers).

In some embodiments, the line-scan imaging device can be configured to receive samples from a single channel flow cytometers are well known in the art. Examples of such FACs systems include, but are not limited to FACS-Caliber™, BD Biosciences, Mountain View, Guava EasyCyte etc, or a disclosed in review article Huh et al. Microfludics for flow cytometric analysis of cells and particles, Physiol Meas. 2005; 26; R73-98, or US Patent applications US2008/0070311 or US2009/0051912, which are incorporated herein by reference in their entirety.

B. Multiplex QPCR Module

As discussed herein, the present invention the line-scan imaging device can be configured such that the output of the microfluidic channels are connected to a HCS for further analysis, for example for analysis of gene expression. In some embodiments, the output of the microfluidic channels are in fluid connection with the input of a HCS for gene expression analysis, such as a high throughput PCR analysis screen, or for example a multiplex QPCR HCS. In one embodiment, the output of the microfluidic channels are in fluid connection with the input of a multiplex qPCR module termed as "reaction mapping", as disclosed in Example 5 and references 24 (Ueberfeld et al., Scaling of Nucleic Acid Assays on Microelectrophoresis Array Devices: High-Dynamic-Range Multigene Readout from less than 10 Transcripts, Electrophoresis, 2009) and Ref 29 (Ueberfeld J, et al., Microdevice DNA Forensics, Humana Press 2009) which are incorporated herein in their entirety by reference. In an alternative embodiment, the output of the microfluidic channels are in fluid communication with the input (i.e. wells) e768-Lane BioMEMS DNA sequencer for long-read (i.e., Sanger) sequencing, as previously described in publications (Ueberfeld J, et al., Microdevice DNA Forensics (in press, Humana Press 2009; El-Difrawy S A, et al., Electrophoresis, 27(19); 3779-3787, 2006; Ueberfeld J, et al., Anal. Chem. 78, 3632-3627, 2006; Goedecke N, et al., J Chroma A, 1111, 206-213 (2006); Aborn J H, et al., Lab on a Chip 6:669-674, 2005; El-Difrawy S A, et al., Rev Sci Instrum 76(7):074301 (2005); Srivastava A, et al., Electrophoresis 26(15-16):1130-1143 (2005); Goedecke, N., et al., Proc. of 9th Intern. Conf. on Miniaturized Systems for Chemistry and Life Sciences, (microTAS) Boston 2005; D. J. Ehrlich, et al., Proc. of 9th Intern. Conf. on Miniaturized Systems for Chemistry and Life Sciences, (microTAS) Boston 2005; El-Difrawy S, et al., Proceedings of the 30th Annual Northeast Bioengineering Conference, Apr. 17-18, 2004, Springfield Mass. IEEE p. 112-113 (2004); Goedecke N, et al., Electrophoresis 25(10-11):1678-1686 (2004); Callewaert N, et al., Electrophoresis 25(18-19): 3128-3131 (2004); Manway L, et al., Proceedings of the Workshop on Genomic Signal Processing and Statistics (GENSIPS), May 26-27, 2004, Baltimore, Md. (2004); Boufounos P, et al., Journal of the Franklin Institute 341(1-2):23-36 (2004); El-Difrawy S and Ehrlich D. Proceedings of the Thirty-Seventh Asilomar Conference on Signals, Systems and Computers, Nov. 9-12, 2003, Pacific Grove, Calif. IEEE 2:2088-2092 (2003); Ehrlich D, et al., Proceedings of First IEEE International Conference on Sensors, Jun. 12-14, 2002, Orlando, Fla. IEEE 1:448-449 (2002); Vazquez M, et al., Analytical Chem 74(9):1952-1961 (2002); Vazquez M, et al., J Chromatogr B 779(2):163-171 (2002); Schmalzing D, et al., In: Heller M H and Guttman A, editors. Integrated Microfabricated Biodevices: Advanced Technologies for Genomics, Drug Discovery, Bioanalysis and Clinical Diagnostics, pp. 55-70. New York: Marcel Dekker (2002); Mitnik L, et al., Electrophoresis 23(5):719-726 (2002); D. Ehrlich, et al., Proc. Micro Total Analysis Systems 2001 (microTAS 2001), Monterey Calif. 2001; Vazquez M, et al., Anal Biochem 73(13): 3035-3044 (2001); Schmalzing D, et al., Methods in molecular biology (series): Capillary electrophoresis of nucleic acids volume II: Practical applications of capillary electrophoresis. Humana Press 163-173 (2001); Koutny L, et al., Anal Chem 72(14):3388-3391 (2000); Salas-Solano O, et al., Anal Chem 72(14):3129-3137 (2000); Schmalzing D, et al., Nucleic Acids Res 28(9):e43 (2000); Schmalzing D, et al., Anal Biochem 270(1):148-152 (1999); Ehrlich D J and Matsudaira P Trends in Biotechnology 17:315-319 (1999); Schmalzing D, et al., Genome Research 9(9):853-858 (1999); Schmalzing D, et al., Electrophoresis 20(15-16):3066-3077 (1999); Schmalzing D, et al., Analytical Chem 70(11):2303-2310 (1998); Koutny L, et al., Proceedings from the Ninth International Symposium on Human Identification, Oct. 8-10, 1998, Orlando Fla. Promega (1998), Schmalzing D, et al., Proc Natl Acad Sci USA 94:10273-10278 (1997)), which are incorporated herein in their entirety by reference and Example 6 herein.

In some embodiments, the line-scan imaging device as disclosed herein can be used to select cells for therapeutic application or disease modeling, or for use in drug screening or toxicity assays. For example, test compounds and agents can be added to samples comprising the cells, and processed and analyzed using line-scan imaging device, systems and methods as disclosed herein. Such the line-scan imaging device is useful to obtain a comprehensive view of such variation of the effect of the test agent or compound on the cell, both on a morphological level and/or on an intracellular level.

Accordingly, the line-scan imaging device, systems and methods as disclosed herein can be used for identify specific characteristics of cells to determine their suitability for downstream applications, such as, their suitability for therapeutic use, drug screening and toxicity assays, differentiation into a desired cell lineage, and the like.

The term "drug screening" as used herein refers to the use of cells and tissues in the laboratory to identify drugs with a specific function. In some embodiments, the present invention provides drug screening methods of differentiated cells to identify compounds or drugs which reprogram a differentiated cell to a reprogrammed cell (e.g. a reprogrammed cell which is in a pluripotent state or a reprogrammed cell which is a stable intermediate, partially reprogrammed cell, as disclosed herein). In some embodiments, the present invention provides drug screening methods of stable intermediate partially reprogrammed cells to identify compounds or drugs which reprogramming differentiated cells into fully reprogrammed cells (e.g. reprogrammed cells which are in a pluripotent state). In alternative embodiments, the present invention provides drug screening on reprogrammed cells (e.g. human reprogrammed cells) to identify compounds or drugs useful as therapies for diseases or illnesses (e.g. human diseases or illnesses).

Drug Screening

In some embodiments, the line-scan imaging device, systems and methods of the invention can be used in in vitro assays, e.g., drug screening and toxicity assays on well defined cells, e.g., human cells, as well as determining effect of genetic variation effect on a cell's drug response (e.g., screening drugs for personalized medicine). Existing assays for drug screening/testing and toxicology studies have several shortcomings because they may not provide sufficient real-time data of the effect of the drug on the cell, or do not provide sufficient information on intracellular changes within the cell in the presence of the test agent. Accordingly, the line-scan imaging device, systems and methods of the invention can be used in drug screening and/or toxicity assays to identify and/or validate drugs for a particular therapeutic use, and/or for personalized medicine use.

Furthermore, the flurry of new information now available on the molecular and cellular level related to human diseases (e.g., microarray data) makes it crucial to develop and test hypotheses about pathogenetic interrelations. The experimental access to specific cell types from all developmental stages and even from blastocysts deemed to harbor pathology based on pre-implantation genetic diagnosis may be useful in modeling and understanding aspects of human disease. Thus, such cell lines would also be valuable for the testing of drugs.

Accordingly, the invention provides a method for screening a test compound for biological activity, the method comprising: (a) obtaining a plurality of cell samples, (b) administering a test compound to a plurality of cell samples, and (c) analyzing the plurality of cell samples in the present and absence of the test compound using the line-scan imaging device, systems and methods as disclose herein. The effect on the cell can be one that is directly observable or indirectly by use of reporter molecules.

As used herein, the term "biological activity" or "bioactivity" refers to the ability of a test compound to affect a biological sample. Biological activity can include, without limitation, elicitation of a stimulatory, inhibitory, regulatory, toxic or lethal response in a biological assay. For example, a biological activity can refer to the ability of a compound to modulate the effect of an enzyme, block a receptor, stimulate a receptor, modulate the expression level of one or more genes, modulate cell proliferation, modulate cell division, modulate cell morphology, or a combination thereof. In some instances, a biological activity can refer to the ability of a test compound to produce a toxic effect in a biological sample.

As used herein, the term "test compound" refers to the collection of compounds that are to be screened for their ability to have an effect on the cell. Test compounds may include a wide variety of different compounds, including chemical compounds, mixtures of chemical compounds, e.g., polysaccharides, small organic or inorganic molecules (e.g. molecules having a molecular weight less than 2000 Daltons, less than 1000 Daltons, less than 1500 Dalton, less than 1000 Daltons, or less than 500 Daltons), biological macromolecules, e.g., peptides, proteins, peptide analogs, and analogs and derivatives thereof, peptidomimetics, nucleic acids, nucleic acid analogs and derivatives, an extract made from biological materials such as bacteria, plants, fungi, or animal cells or tissues, naturally occurring or synthetic compositions.

Depending upon the particular embodiment being practiced, the test compounds may be provided free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds may be screened individually, or in groups. Group screening is particularly useful where hit rates for effective test compounds are expected to be low such that one would not expect more than one positive result for a given group.

A number of small molecule libraries are known in the art and commercially available. These small molecule libraries can be screened for inflammasome inhibition using the screening methods described herein. For example, libraries from Vitas-M Lab and Biomol International, Inc. Chemical compound libraries such as those from of 10,000 compounds and 86,000 compounds from NIH Roadmap, Molecular Libraries Screening Centers Network (MLSCN) can be screened. A comprehensive list of compound libraries can be found at http://www.broad.harvard.eduichembio/platform/screening/compound_libraries/index.htm. A chemical library or compound library is a collection of stored chemicals usually used ultimately in high-throughput screening or industrial manufacture. The chemical library can consist in simple terms of a series of stored chemicals. Each chemical has associated information stored in some kind of database with information such as the chemical structure, purity, quantity, and physiochemical characteristics of the compound.

Without limitation, the compounds can be tested at any concentration that can exert an effect on the cells relative to a control over an appropriate time period. In some embodiments, compounds are testes at concentration in the range of about 0.01 nM to about 1000 mM, about 0.1 nM to about 500 $\mu$M, about 0.1 $\mu$M to about 20 $\mu$M, about 0.1 $\mu$M to about 10 $\mu$M, or about 0.1 $\mu$M to about 5 $\mu$M.

The compound screening assay may be used in a high through-put screen. High through-put screening is a process in which libraries of compounds are tested for a given activity. High through-put screening seeks to screen large numbers of compounds rapidly and in parallel. For example, using microtiterplates and automated assay equipment, a pharmaceutical company may perform as many as 100,000 assays per day in parallel.

The compound screening assays of the invention may involve more than one measurement of the observable reporter function. Multiple measurements may allow for following the biological activity over incubation time with the test compound. In one embodiment, the reporter function is measured at a plurality of times to allow monitoring of the effects of the test compound at different incubation times.

The screening assay may be followed by a subsequent assay, e.g., at a second timepoint, to further identify whether the identified test compound has properties desirable for the intended use. For example, the screening assay may be followed by a second assay selected from the group consisting of measurement of any of: bioavailability, toxicity, or pharmacokinetics, but is not limited to these methods.

In some embodiments of the present invention may be defined in any of the following numbered paragraphs:

1. A line-scan imaging device for rapid image analysis of particles in multiple samples of interest, comprising: (a) a microfluidic device comprising a plurality of microchannels, wherein each microchannel has an inlet and at least one outlet; (b) a scanning detector configured to record emitted fluorescence in a portion of each of the plurality of microfluidic channels of the microfluidic device; and (c) an output device configured to receive data input from the scanning detector.
2. The line-scan imaging device of paragraph 1, wherein the output device comprises a storage device.
3. The line-scan imaging device of paragraphs 1 or 2, wherein the out put device comprises a data analysis system that permits cell phenotype determination from the emitted fluorescence detected in step (b).
4. The line-scan imaging device of any of paragraph 1 to 3, wherein the scanning detector is a 1-D image detector.
5. The line-scan imaging device of any of paragraphs 1 to 4, wherein the scanning detector is a sparse 2-D image detector.
6. The line-scan imaging device of any of paragraphs 1 to 4, wherein the scanning detector is a laser-induced florescence (LIF) detector.
7. The line-scan imaging device of any of paragraphs 1-6, wherein the scanning detector comprises a plurality of photomultipliers (PMTs) and/or photodiode detectors.
8. The line-scan imaging device of any of paragraphs 1-7, wherein the photodiode detector is an avalanche photodiode.
9. The line-scan imaging device of any of paragraphs 1-8, wherein each microchannel of the plurality of microchannels is at least 30 µm wide in diameter.
10. The line-scan imaging device of any of paragraphs 1-8, wherein each microchannel of the plurality of microchannels is no more than 300-µm wide in diameter.
11. The line-scan imaging device of any of paragraphs 1-8, wherein each microchannel of the plurality of microchannels is 100-µm wide in diameter.
12. The line-scan imaging device of any of paragraphs 1-µl, wherein the scanning detector records emitted fluorescence at 6 µm intervals or less across the diameter of each microchannel of the plurality of microchannels.
13. The line-scan imaging device of any of paragraphs 1-12, wherein the scanning detector records emitted fluorescence at 3.5 µm intervals or less across the diameter of each microchannel of the plurality of microchannels.
14. The line-scan imaging device of any of paragraphs 1 to 13, wherein the detector has a detection diameter of between 1-5 µm parallel to the microchannel.
15. The line-scan imaging device of any of paragraphs 1 to 14, wherein the detector has a detection diameter of less than one microchannel diameter parallel to the microchannel.
16. The line-scan imaging device of any of paragraphs 1 to 15, wherein the detector has a detection diameter of 3 µm parallel to the microchannel.
17. The line-scan imaging device of any of paragraphs 1 to 16, wherein the inlet of each of the plurality of microchannels fluidly connects to plurality of sample wells for sample input into each microchannel.
18. The line-scan imaging device of any of paragraphs 1 to 17, wherein each sample well for sample input into each microchannel is a well on a microwell plate.
19. The line-scan imaging device of any of paragraphs 1 to 18, wherein the each microchannel has at least one positive outlet and at least one negative outlet to permit sorting of cells between positive and negative states.
20. The line-scan imaging device of paragraph 19, wherein the each positive outlet is fluidly connected to a positive sample well for positive output sample collection, and each negative outlet is fluidly connected to a negative sample well for negative sample collection.
21. The line-scan imaging device of paragraphs 17 to 20, wherein the sample well is configured for sample addition or suction pipetting.
22. The line-scan imaging device of any of paragraphs 17 to 21, wherein the sample well receives samples from the output of a plurality of microfluidic channels from a parallel microfluidic cytometer.
23. The line-scan imaging device of any of paragraphs 1 to 21, wherein the inlet of the plurality of microchannels are in liquid communication through a capillary passageway to the output of a plurality of microfluidic channel of a parallel microfluidic cytometer (PMC).
24. The line-scan imaging device of any of paragraphs 1-23, wherein each microchannel of the plurality of microchannels on the microfluidic device is configured for vertical hydrodynamic focusing.
25. The line-scan imaging device of any of paragraphs 1-24, wherein the vertical hydrodynamic focusing uses multiple crossing junctions of each microchannel to flow into a single analytical microchannel.
26. The line-scan imaging device of any of paragraphs 1-25, wherein the vertical hydrodynamic focusing locates at least one cell to a zone of 200 m or smaller in the direction of the optical focus.
27. The line-scan imaging device of any of paragraphs 1-26, wherein the detector collects at least 320 points at 1 µm spacing along the linear length of each of the plurality of microchannels.
28. The line-scan imaging device of any of paragraphs 1-27, wherein the detector collects 100 points at 1 µm spacing along the linear length of each of the plurality of microchannels.
29. The line-scan imaging device of any of paragraphs 1-28, wherein each microchannel of the plurality of microchannels on the microfluidic device further comprises a piezoelectric microswitch for cell sorting.
30. The line-scan imaging device of any of paragraphs 1-29, wherein the input data of the storage device is the output data of florescence values recorded from the plurality of PMTs of the scanning detector.
31. The line-scan imaging device of paragraph 30, wherein the detector constructs a digital line-scan image of at least 14-bits of at least one cell that passes through a microfluidic channel.
32. The line-scan imaging device of any of paragraphs 1-31, wherein at least 2 line-scan images are produced for each cell.
33. The line-scan imaging device of any of paragraphs 1-32, wherein at least 5 line-scan images are produced for each cell.
34. The line-scan imaging device of any of paragraphs 1-33, wherein the storage device is connected to a comparison module.
35. The line-scan imaging device of any of paragraphs 1-34, wherein the comparison module is a non-human computer.

36. The line-scan imaging device of any of paragraphs 1-35, wherein the comparison module compares at least one line scan image of the cell with a reference point indicating a cell phenotype.
37. The line-scan imaging device of any of paragraphs 1-36, wherein the comparison module compares at least 5 line scan images of the cell with a reference point indicating a cell phenotype.
38. The line-scan imaging device of any of paragraphs 1-37, wherein the comparison module compares at least 10 line scan images of the cell with a reference point indicating a cell phenotype.
39. The line-scan image device of any of paragraphs 36-38, wherein the reference point indicating a cell phenotype is a reference line scan image of cell phenotype.
40. The line-scan image device of any of paragraphs 36-39, wherein the reference point indicating a cell phenotype is a value from an algorithm indicating a cell phenotype.
41. The line-scan imaging device of any of paragraphs 1-40, wherein the comparison module is configured to analyze at least one line-scan image of each cell by comparison with a reference line scan image, and wherein if the line-scan image of the cell has substantially similar cell features as a preselected reference line scan, the comparison module sends instructions to the microfluidic device to trigger or de-select switching of the piezoelectric microswitch in the microchannel in which the cell was scanned, enabling selection of the cell.
42. The line-scan imaging device of any of paragraphs 1-41, wherein the comparison module is configured to analyze a line-scan image, or a plurality of line-scan images of a cell via a cell-typing algorithm, and wherein the identity of cell type via the cell type algorithm triggers or de-selects switching of the piezoelectric microswitch in the microchannel in which the cell was scanned, enabling selection of the cell.
43. The line-scan imaging device of any of paragraphs 1-42, wherein a line image of a cell which has substantially similar cell features as the line image of a reference line scan image identifies a cell with a positive cell type and triggers fluid flow along the microchannel to a sample collection well.
44. The line-scan imaging device of any of paragraphs 1-43, wherein a line image of a cell which has a cell type similar to a reference cell type is identified as a positive cell and triggers fluid flow along the microchannel to a positive sample collection well.
45. The line-scan imaging device of any of paragraphs 1-44, wherein a line image of a cell is significantly different to a reference cell type is identified as a negative cell and triggers fluid flow along the microchannel to a negative sample collection well.
46. The line-scan imaging device of paragraphs 44 or 45, wherein the line image of a cell identifies the cell as a positive cell or a negative cell by comparison of the line image with at least one reference point.
47. The line-scan imaging device of paragraphs 44 or 45, wherein the line image of a cell is used to identify a cell as a positive cell or a negative cell using a cell-type algorithm.
48. The line-scan imaging device of any of paragraphs 1-47, wherein the output of each microfluidic channel of a plurality of a microfluidic channels is in liquid communication through a capillary passageway to the input of a high content screening (HCS) assay.
49. The line-scan imaging device of any of paragraphs 1-48, wherein high content screening (HCS) assay is selected from the group consisting of: a quantitative gene expression assay., a multiplex quantitative PCR module, a biomolecular assay, a cell based assay, a microscope-based image assay.
50. The line-scan imaging device of any of paragraphs 1-49, wherein high content screening (HCS) assay uses a multiplex quantitative PCR module.
51. The line-scan imaging device of any of paragraphs 1-50, wherein storage device is connected to a display module.
52. The line-scan imaging device of any of paragraphs 1-51, wherein storage device is connected to a display module.
53. The line-scan imaging device of any of paragraphs 1-52, wherein device comprises at least 16 microchannels.
54. The line-scan imaging device of any of paragraphs 1-53, wherein device comprises at least 32 microchannels.
55. The line-scan imaging device of any of paragraphs 1-54, wherein device comprises at least 384 microchannels.
56. The line-scan imaging device of any of paragraphs 1-55, wherein device comprises at least 768 microchannels.
57. The line-scan imaging device of any of paragraphs 1-56, wherein device comprises at least 1536 microchannels.
58. The use of the line-imaging device of any of paragraphs 1-57 for identifying a rare cell with a population of cells in a sample.
59. The use of the line-imaging device of paragraph 58, wherein a rare cell comprises 0.1% or less of the total cell population.
60. The use of the line-imaging device of any of paragraphs 1-52 for identifying and selecting cells in a population of cells in a biological sample.
61. The use of the line-imaging device of paragraph 60, wherein the biological sample is from a subject.
62. The use of the line-imaging device of paragraph 62, wherein the subject is a human subject.
63. The use of the line-imaging device of paragraph 60, wherein the selected cells are a population of rare cells.
64. The use of the line-imaging device of paragraph 63, wherein the population of rare cells comprise at less than 10% of the total cells in the population of cells.
65. The use of the line-imaging device of paragraph 64, wherein the population of rare cells comprise at less than 5% of the total cells in the population of cells.
66. The use of the line-imaging device of paragraph 65, wherein the population of rare cells comprise at less than 1% of the total cells in the population of cells.
67. The use of the line-imaging device of paragraph 66, wherein the population of rare cells comprise at between 0.5%-0.001% of the total cells in the population of cells.
68. The use of the line-imaging device of any of paragraphs 58-67, to identify cells in at least 16 biological samples at the same time.
69. The use of the line-imaging device of paragraph 68, wherein the 384 biological samples are analyzed in less than 10 minutes.
70. The use of the line-imaging device of paragraph 68, wherein the 384 biological samples are analyzed in less than 7 minutes.
71. The use of the line-imaging device of any of paragraphs 58-70, wherein intracellular protein and/or protein localization is determined in cells in a cell population from 384 biological samples.
72. The use of the line-imaging device of any of paragraphs 58-70 for counting rare cells.

EXAMPLES

The examples presented herein relate to systems, instruments and methods which couple high-content screening (HCS) systems with line-scan imaging, e.g. 1-D and 2-D line scan imaging in a parallel flow instrument. Such a system is referred to herein as a "parallel flow FACS-line scan imaging system". Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

In summary, the inventors demonstrate, first, through modeling and simulation, data-reduction algorithms for high-content 1-D and 2-D (low-complexity) line-scan cell assays. The inventors verify these algorithms as protein-localization assays with line-scan data. Additionally, the inventors demonstrate a throughput of >10 each 384-well plates/hour, which is approximately 10-30 times faster processing (i.e. throughput) over that of existing HCS (microscope-based) systems. The inventors demonstrate this on a platform that can be adapted for sorting of cells according to image information and visual phenotype of the cells determined by line imaging.

Second, the inventors have developed a scanning confocal-slit, line-scan module (2 lasers, 5-color detection, 32 parallel fluidic channels) that can demonstrate this high throughput (approximately 10-30 times higher throughput) for use on a parallel microfluidic cytometer (PMC). Such a line-scan module can be conformed in an architecture that can be expanded to add additional lasers and detectors and be configured to be attached to a PMC module, such as a PMC of 384-lane complexity. The inventors assessed, tested and optimized the line-scan detection module (also referred to herein as the "line-scan module") using fluorescent beads as well as cells labeled with a variety of fluorescent markers, such Swiss 3T3 cells. The line-scan detection module was also verified using a nuclear translocation assay on 3T3 cells according to NIH CGC assay validation procedures.

Third, the inventors have added the line-scan imaging module as disclosed herein to existing commercial (single-channel) cytometers. Thus, the line-scan imaging module is capable of "high-content" capability. The inventors demonstrate use of the line-scan imaging module for high-content screening method for analysis of cells or other components in a sample that uses time-domain encoding to multiplex image information onto a single detector.

Fourth, the line-scan imaging module in parallel with a PMC module, e.g. a cytometer can be used to assay for small molecules for the treatment of diseases. For example, the inventors validate, through NIH CGC procedures, a yeast-based HCS assay for studies of amyloid-related neurodegenerative disease (e.g., Parkinson's). The inventors demonstrate high throughput and scalability of this assay using the line-scan imaging module in parallel with a PMC module (e.g. FACs module or other cytometers) for small-molecule studies related to neurodegenerative disease. Additionally, the inventors demonstrate the accuracy of the line-imaging module in this parallel flow FACS-line scan imaging system to verify a nuclear translocation assay on mouse hematopoietic stem cells using a sample size of between 100-1000 cells. The inventors also demonstrate validation and feasibility of this parallel flow FACS-line scan imaging system using a scaled RNAi HCS assay on primary stem cells by PMC imaging.

The present invention relates to parallel microfluidics. In a previous study the inventors combined a higher-throughput imaging flow cytometry (faster than current CCD imaging), combined with sorting and combined it with multiplexed down-stream QPCR on sorted fractions. The inventors previously demonstrated that this system, referred to as a parallel microfluidic cytometer (PMC) would allow the full workflow on a single platform (with repeated use of a single sensor, with central automation, with high throughput, and with small cell fractions, 1-10 cells). Thus, the inventors have previously demonstrated a parallel microfluidic system with flow sorting and electrophoresis readout of the multiplex quantitative PCR (QPCR). The inventors previously generated a new solution for multiplexed QPCR readout from less than 10 transcripts on our system (Ueberfeld J, et al., *Analytical Chemistry,* 80, 7430-7436 (2008); Ueberfeld, J. and Ehrlich, D. J. (in Press 2009)) and, (2) demonstrated a parallel microfluidic cytometer (384-parallel channels, 4-color readout) (Mckenna B K, et al., *Lab on a Chip* 9, 305-310, 2009; Selim A, et al., *Bone Miner Res* 20 (suppl 1):S183 (2005)).

The present invention extends these developments to provide some form of imaging (beyond unresolved FACS) in order to better phenotype fractions following flow sorting, and as an alternative to, or prior to assessment of the sorted cells by multiplex QPCR.

Thus the present invention relates to a fast imaging cytometry (1-D line-scan) imaging that allows 10-30 times increased throughput for the parallel flow cytometer over existing CCD-based instruments. The inventors demonstrate that use of a line-scan module as an intermediate step between the flow sorting (i.e. via a 384-parallel channel microfluidic cytometer) either alone, or prior to the multiplex QPCR module could add "high-content" to existing (commercial) single-channel flow cytometers. Therefore, the present invention provides a high-throughput line-scan imaging assays that can be implemented in the short term on a single channel but can be scaled on a parallel microfluidic cytometer (PMC).

Thus, the inventors have developed an line-scan image module for high throughput analysis which overcomes the limitations in of existing microscope based analysis systems and FACS sorting. In particular, the inventors have developed a line-scan image module which has an increased throughput similar to the throughput capacity of FACS. Accordingly, the inventors have added to the main strengths of FACS (i.e. high throughput cell sorting based on size and expression of fluorescence markers) by adding an imaging capability for further sorting the cells based on phenotype and morphological characteristics. The inventors have configured the line-scan image module to ne high capacity and high throughput, thus overcome the sample-change constraint (i.e. moving sorted samples from FACS to a different imaging platform) that limits the use of FACS in combinatorial applications. This the present inventors have add an imaging capability to FACS, in order to provide means for HCS assays in flow.

The PMC offers a way to increase the throughput of image-based HCS into the domain of FACS through a flow architecture rather than static imaging. The approach described herein circumvents the rate limitations of the CCD (microscopes and CCDbased flow cytometers) by using a 1-D scanner and photomultiplier detection. The principal PMC instrument adjustment relative permits the spatial resolution of the scanner in FIG. 1 to be increased, and thereby collect multiple intracellular pixels on each cell that is detected in the flow. The scanner then collects a multicolor "line-scan", from each microfluidic channel.

Yeast and Stem Cells as Models for Human Disease:

The inventors have used Yeast and stem cells to optimize the line-scan module as disclosed herein for a high capacity and high throughput analysis. Yeast are useful study organisms as they are simple systems of only 6000 genes, yet recapitulate the essential problems of protein miss-folding in a model system that is easily and consistently manipulated.

Example 1

The design of a PMC differs from a FACS in (1) its need for a wide field of view detector (rather than a focused point detector), (2) its need for automation to support parallel sample transfer, (3) its differing needs for data processing and (4) the design of the microfluidic itself. The detector of the PMC is more complex than a FACS detector since the widefield requirement mandates the use of a scanner and permits high-speed imaging.

Figure 14A:
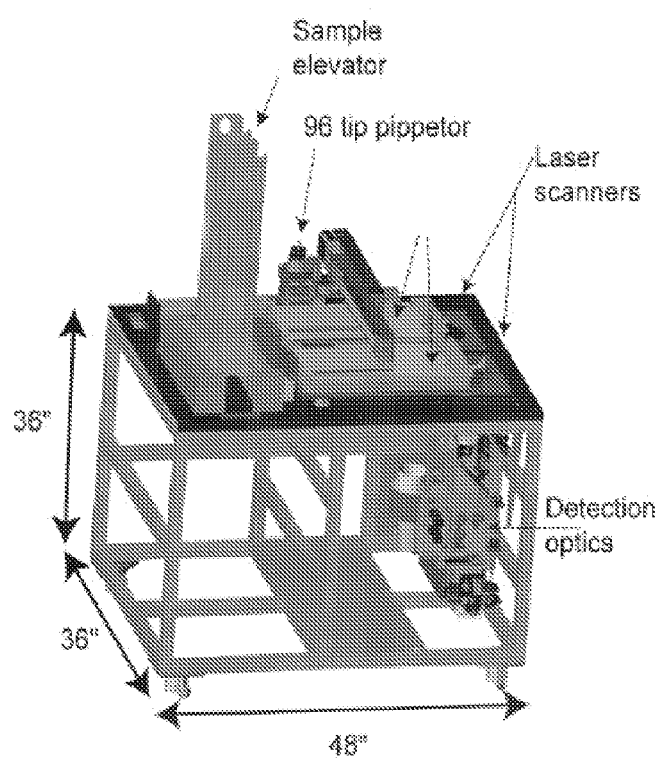
FIGS. 14A-14B are micrographs depicting an exemplary parallel microfluidic cytometer (PMC) for cell based assays. This particular system is designed for automated fluorescence measurements on 384-channel microfluidic plates and comprises up to two temperature-controlled microfluidic "chips" (16 to 384 channels each), a scanning detector and automated pipettor/sample elevator for automated maintenance of cell suspensions/cultures. Cell suspensions can be pulled by vacuum suction from injection wells using a positive-displacement syringe pump. Multicolor detection is via a scanned confocal detector that oscillates below the microfluidics.
Figure 14B:
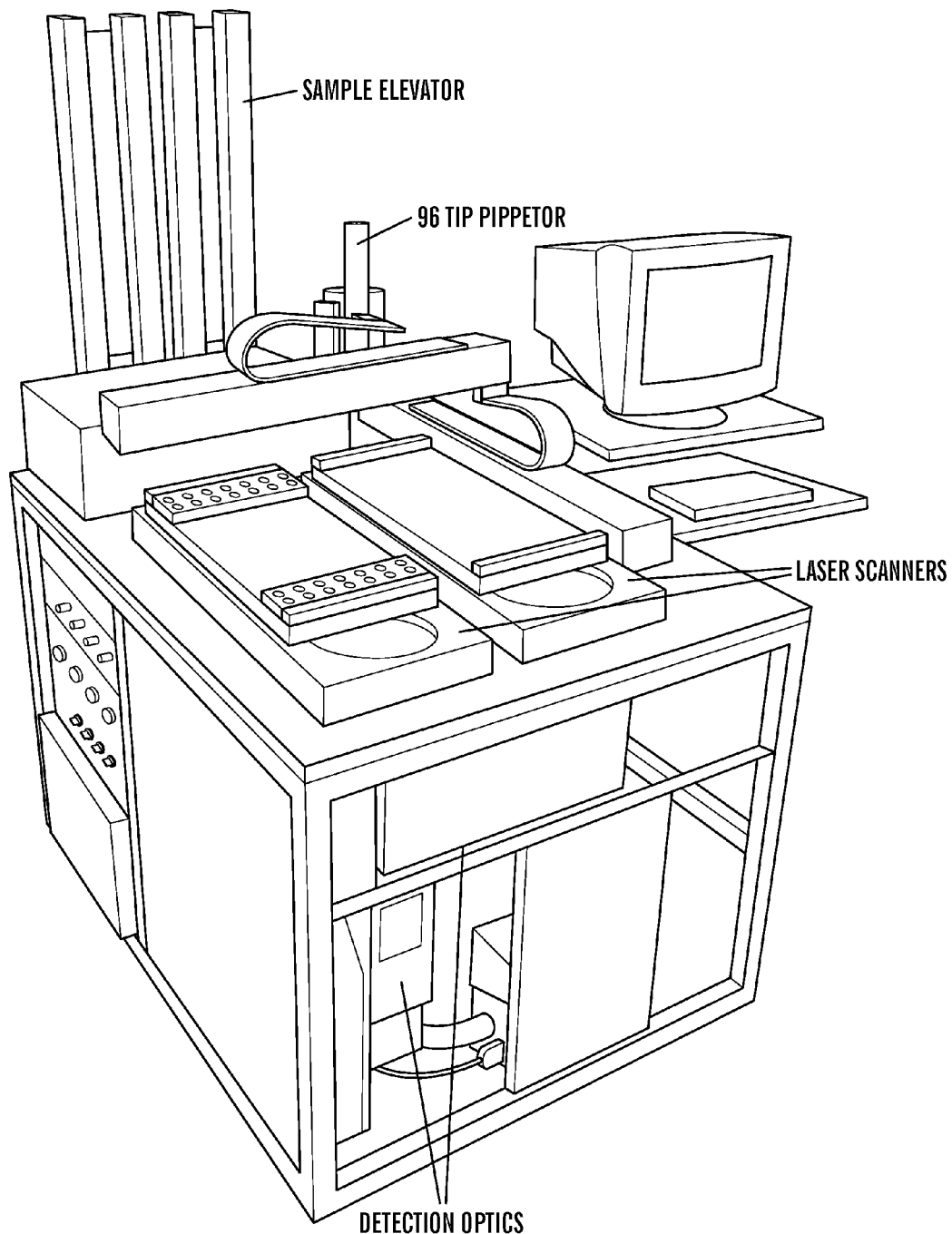
Figure 15A:
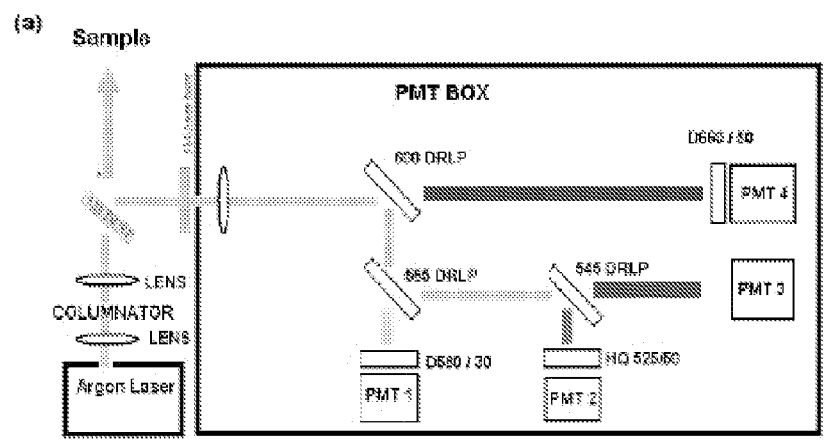
FIGS. 15A-15B are schematic drawings showing two exemplary configurations of the optical detector to match cell assays used for the PTHR screen (15A), and for a dilution study on primary leukemia cells (15B). The scattered forward light sensor in FIG. 15B is a fiber optic (910-µm diameter, 0.22 nA) on a rotatable mount that can be adjusted in the range from 20 degrees to 70 degrees off the forward direction.

An exemplary automated PMC is shown herein in FIGS. 14 and 15. The microfluidic flow devices can be mounted on a top plate and can be serviced with a gantry robot combined with a sample elevator that handles 384-well microtiter plates. In one embodiment, the fluid handling is via an integrated 96-tip pipettor that permits automated maintenance of 384-well plates on a temperature controlled base. The sample deck can include positions for nutrient/wash trays that can also be accessed by the pipettor. As a result, live cell cultures can be sustained for several days (e.g., at least 1, at least 2, at least 3, at least 4, at least 5, at least 6, at least 7, at least 10, at least 14, at least 20 days or more) on the system. Alternatively, the cells can be loaded from an off-system culture apparatus. In one embodiment, all of the channels (e.g., 384 channels) are loaded from a microtiter plate in e.g., less than 5 min, less than 4 min, less than 3 min, less than 2 min, less than 1 min, less than 45 sec, less than 30 sec, less than 20 sec, less than 10 sec or less. In one embodiment, 384 channels are loaded from a microtiter plate in less than 30 seconds.

Flow can be actuated by suction using syringe pumps. In one embodiment, the optical detector is a photomultiplier-based rotary scanner located under the microfluidics system. The system can be operated from a graphical user interface that displays data during real time. However, in some embodiments data reduction is done on exported files offline.

Robotics In one embodiment, the stages of the X-Y-Z axis (GL16S with 1250 mm of travel for the x-axis, a KR46 with 540 mm of travel for the Y-axis, and KR26 with 65 mm of travel for the Z-axis (T.H.K. Ltd, Tokyo, Japan) are driven by a set of three servo drivers (SGDH-01AE, Yaskawa Electric, Japan) and are coordinated by a six-axis motion controller (Model 6k6 Compumoter, Rohnert Park, Calif.). The pippetor head can have programmable suction and injection capability for volumes between 2 and 20 µl and can be driven by a DC brushless servo amplifier (Model 503, Copley controls Corp, Westwood, Mass.). In one embodiment, a 96-tip robot head accesses water and buffer reservoirs, an ultra sound washing station, a microtiter plate elevator with up to 32 sample plates for continuous operations (Packard Instrument Co., Meridien, Conn.).

PMC Detector In some embodiments, the PMC detector has a meso-scale sensor field, a high time response, and a variable integration time. In some embodiments, out-of-plane (e.g., confocal) background-light rejection is used. In some embodiments, a photomultiplier or avalanche photodiode detector is used instead of a CCD or CMOS imager. In one embodiment, a modified PMT fluorescent scanner used for DNA sequencing (El-Difrawy et al., *Rev Sci Instrum* 76(7): 074301, 2005) is used. For example, a 100-mW multi-line argon ion laser beam is passed through a rotating head that moves a 0.5-numerical aperture (NA) aspheric lens and can be driven by a DC brushless motor. The laser focus can be adjusted to NA ~0.01 for a laser spot size of 25- to 30-µm diameter at its best focus, to excite fluorescence as the rotating head moves beneath the detection window. The fluorescence is then collected at NA 0.5 through the rotating head and can be separated into four wavelength bands using dichroics and bandpass filters and distributed onto four PMTs (e.g., H957-8 Hamamatsu, Bridgewater, N.J.).

Non-uniform velocity and cycle-to-cycle fluctuations cause variations in the level of the collected signal and results in added noise. Therefore we have built a PID controller that maintains the speed profile of the rotating head. The parameters of the PID controller are tuned to minimize speed fluctuations during the collection arc while maximizing accelerations outside the arc. The position of the rotating head is measured using an optical encoder (HT30P156 D14 N4096, Dynamic Research Corporation, Wilmington, Mass.). A proportional-integral-derivative (PID) controller maintains the speed profile and is tuned to minimize scan-to-scan speed fluctuations while maximizing accelerations outside the collection arc.

The rotating head is programmed to a saw-tooth velocity profile at 12 or 3 Hz recording 300-2,800 data points across a window of ~3.5-80 mm, or in a modulated circular motion. For each encoder point the values of the 4 PMTs are recorded and the 16-bit digital value is saved to the PC hard drive 12(3) times a second.

The constancy and reproducibility of the speed profile have been measured and show a standard deviation of less than 1% from the target velocity (10,000 scans, all flow channels). The sensitivity of the system was evaluated with fluorescence standards and shown to a 10 µm fluorescein detection limit in the 60 µm deep channel, which is near the state of the art for on-column LIP detectors.

Data processing The data acquisition and PID control are synchronized using a digital signal processor (DSP, ADSP-2181, Analog Devices, Norwood, Mass.) running at a clock rate of 33 MHz. The PID controller runs at a servo rate of 1 kHz while the data acquisition is performed at a faster rate of 200 kHz. The collected sequencing data is uploaded from the DSP memory to the PC through the PC parallel port, which runs in the enhanced parallel port (EPP) mode. A simple control circuit is used to provide the PC with direct memory access to the program and data memory of the DSP processor.

Raw PMT data is saved in 4 files representing 16-bit data at each location separated by 10 µm in the scan window. Each file contains the data for one PMT. The data is first processed to eliminate scan areas without cells. The 2800-bit (80 mmscan) by n (scan) data is then segmented into channel-specific section of ~20 bits by n scans. This data is then reformatted into 512×512×16 bit grayscale images and saved as TIFF images for each PMT channel. A calculated image is then created by subtracting the red channel from green (negative values are set to zero). For the initial levels of the screen the TIFF images for the virtual channel are then reviewed and all bright cells (those have at least one pixel greater than 10,000RFUs) are counted.

Microfluidics Microdevices with 16, 32, and 384 channels were fabricated in aluminasilicate glass (Corning, EAGLE). Unaligned single-mask contact lithography was followed by high-temperature fusion bonding of 0.7 mm thick plates of 25×50 and 25×25 cm size. The microchannels had a hemispherical cross section with a radius of 60 µm and converged to a density of 5-channels/mm in the scan zone. In the network layouts, channels (20-40 mm length, 1-3 µl internal volume)

were matched to a few percent in flow resistance. Access for introduction of the cell suspension was through laser-drilled ports, which were conical in shape and terminated at the flow channel with an exit of ~80-100 μm diameter. Composite G-10 fiberglass boards were mechanically machined with 2-mm-diameter sample wells distributed on 4.5-mm or 9.0-mm centers, and were glued with thermally curing epoxy on top of the bonded glass devices.

Flow and Flow Focusing Microfluidic systems, created by lithographic methods, are generally constrained as two-dimensional (X,Y) flow networks. One-dimensional squeezing, in the plane of the flow network, is relatively easy to accomplish simply by using T-junctions. However "vertical" hydrodynamic focusing (in the plane perpendicular to the network) is more germane for narrow-depth-of-field optical detection of the PMC. In order to focus microfluidic flows vertically, it is necessary to utilize a torque (out of the plane of the network) or to merge flows as vertically distinct layers. From a fabrication standpoint, the geometry in which layers are introduced by intersecting two vertically displaced channels is easiest; this approach requires only a simple unaligned (or weakly aligned) two-level network structure, with no significant microfabrication changes from our normal unaligned procedure. From a modeling point of view the geometry is slightly more complicated since the normal isotropic wet etching procedure produces a nearly hemispherical channel cross-section and flow profiles are highly sensitive to relatively small changes in channel cross-section.

Figure 19:
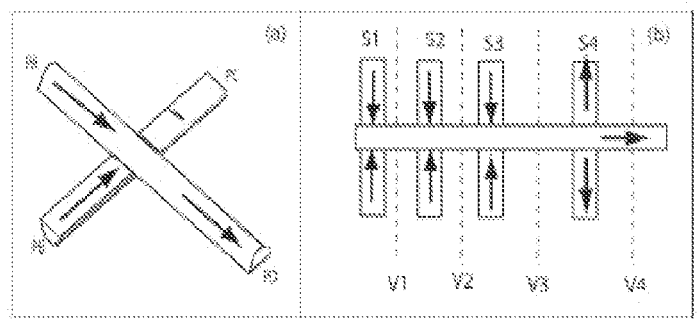
FIG. 19 shows an exemplary simple crossing junction used as a design element in software and imaging calibrations having two inlet flows from PA and PB and a single outlet flow from PD. No flow is permitted through PC (wall boundary condition). The analysis channel is on top while the sheath channel is on the bottom. Percentages of flow from PA and PB are in reference to PD, the total flow after the junction (right side) illustrates the four-level compensated vertical focusing device modeled in FIGS. 5A, 5B, 20A and 20B. Additive sheath (symmetric sheath inputs S1 and S3) and additive analysis (symmetric S2) are combined upstream of a correction flow (symmetric S4). The device is driven by suction from a port at the right end. Adjustable flow resistances on the channels S1-S4 are used to tune the device.
Figure 20A:
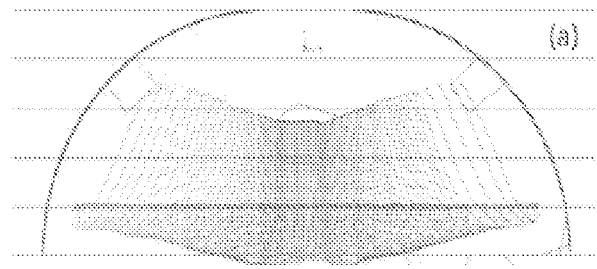
FIGS. 20A-20B show exemplary simulations of four-layer focused flow, 20A before, and 20B after the channel S4 junction and subtractive correction flow (plane V4). As the traces pass beyond the channel S4 junction they are preferentially pulled downward and outward. The flow interface indicated by the arrows is most strongly altered by the subtractive flow.
Figure 20B:
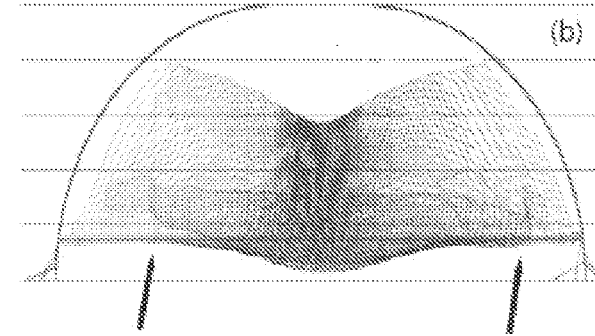
Figure 21A:
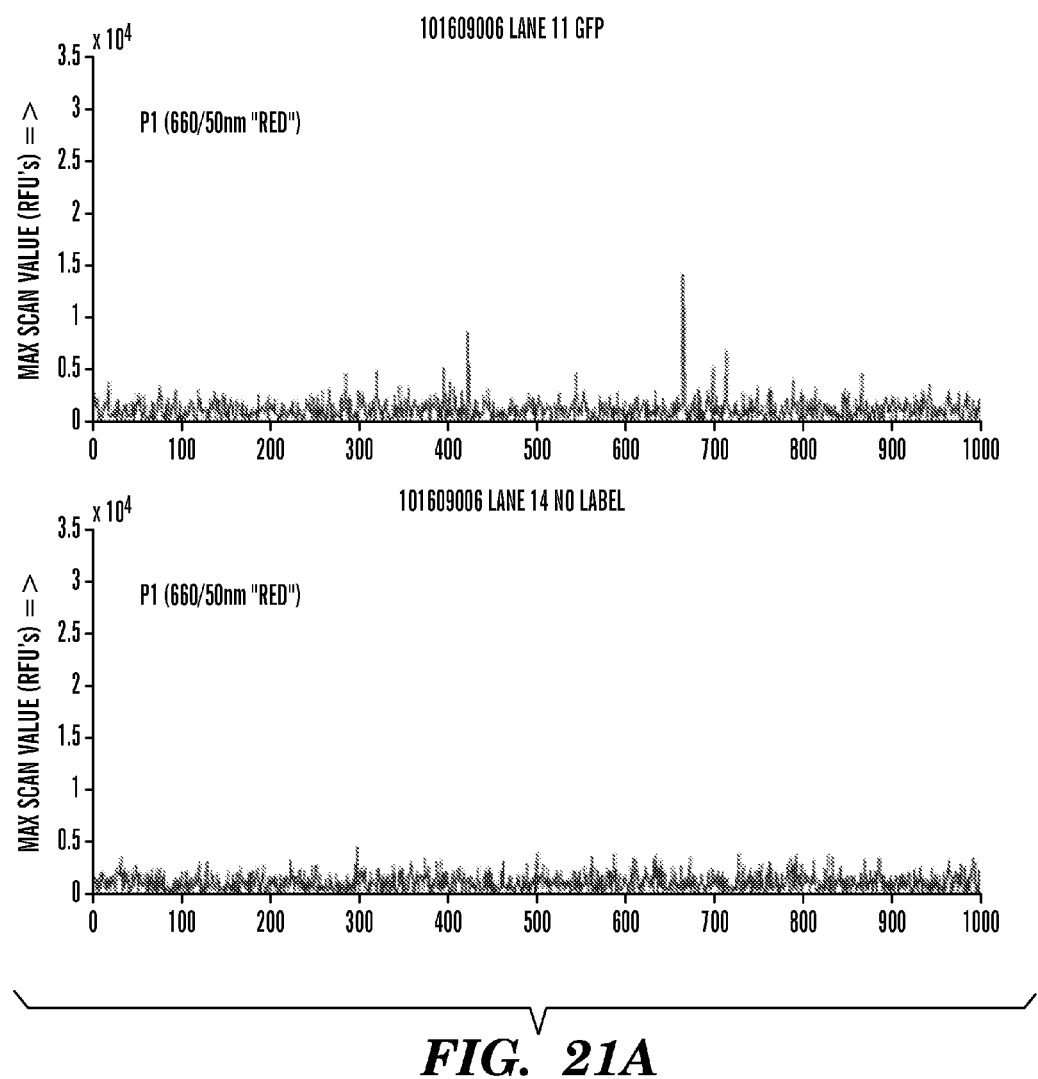
FIGS. 21A-21D show exemplary raw data. Two sample types showing raw signal on all four photomultipliers (PMT's) using the detector layout of FIG. 15B. The x-axis is time, designated as scan number, 12 scans per second. The labeled and unlabeled cells show up as events on the scatter detector, while GFP cells appear as fluorescent spikes on the P1-P3 color PMT's. Weak autofluorescence is occasionally observable on P3 (unlabeled cells). For the GFP sample, the signal ratios vary significantly, e.g., P2 (GFP channel) compared to P3 (Yellow channel).
Figure 21B:
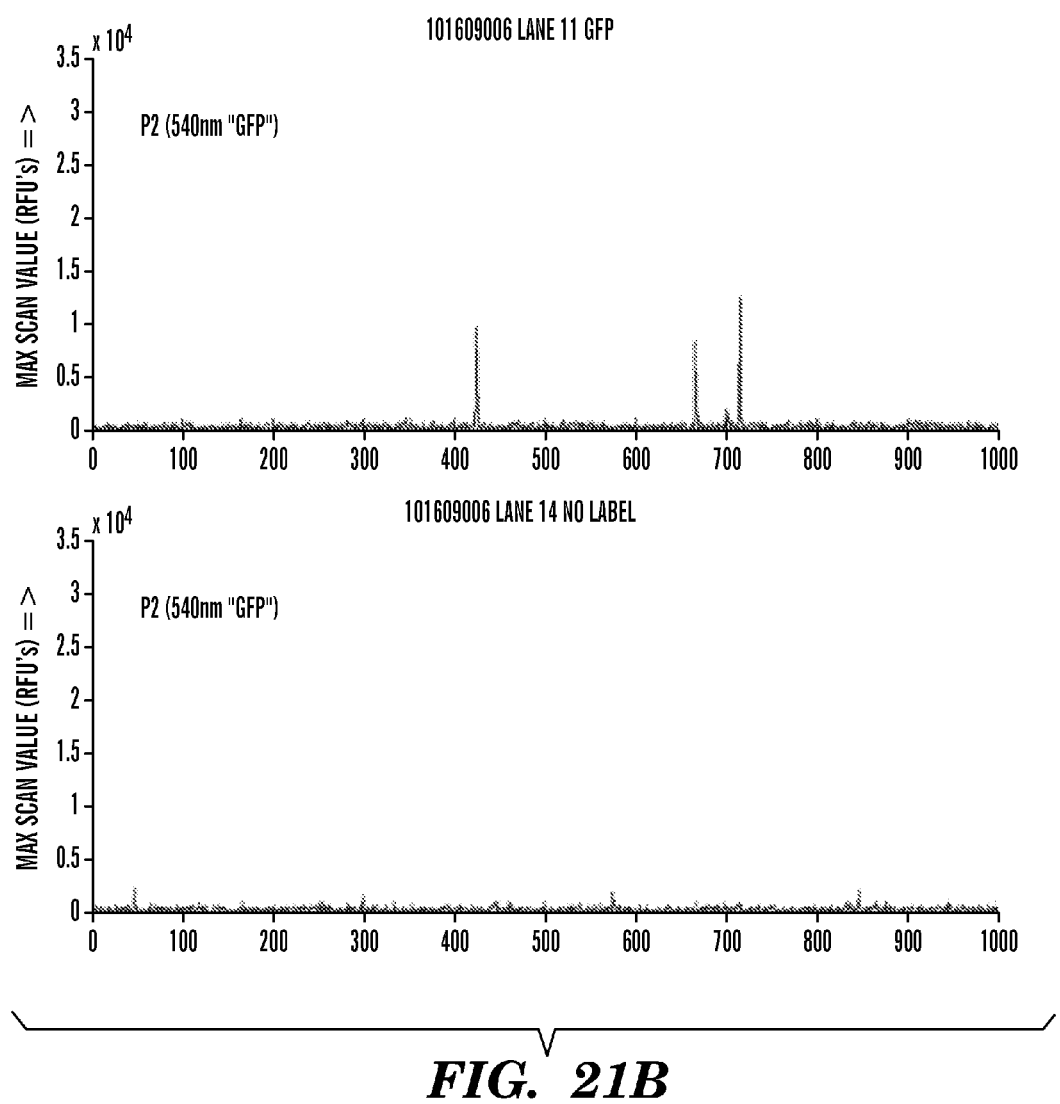
Figure 21C:
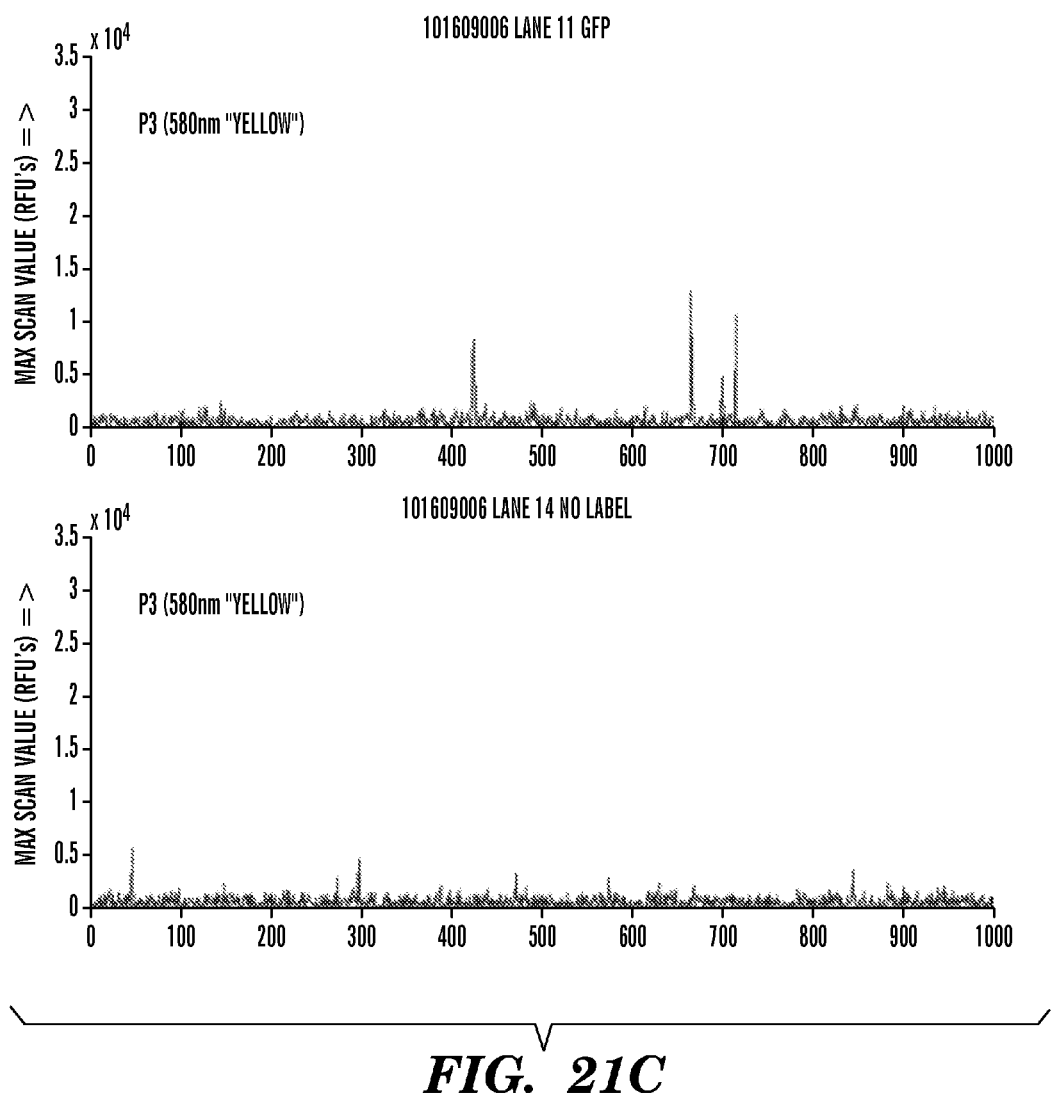
Figure 21D:
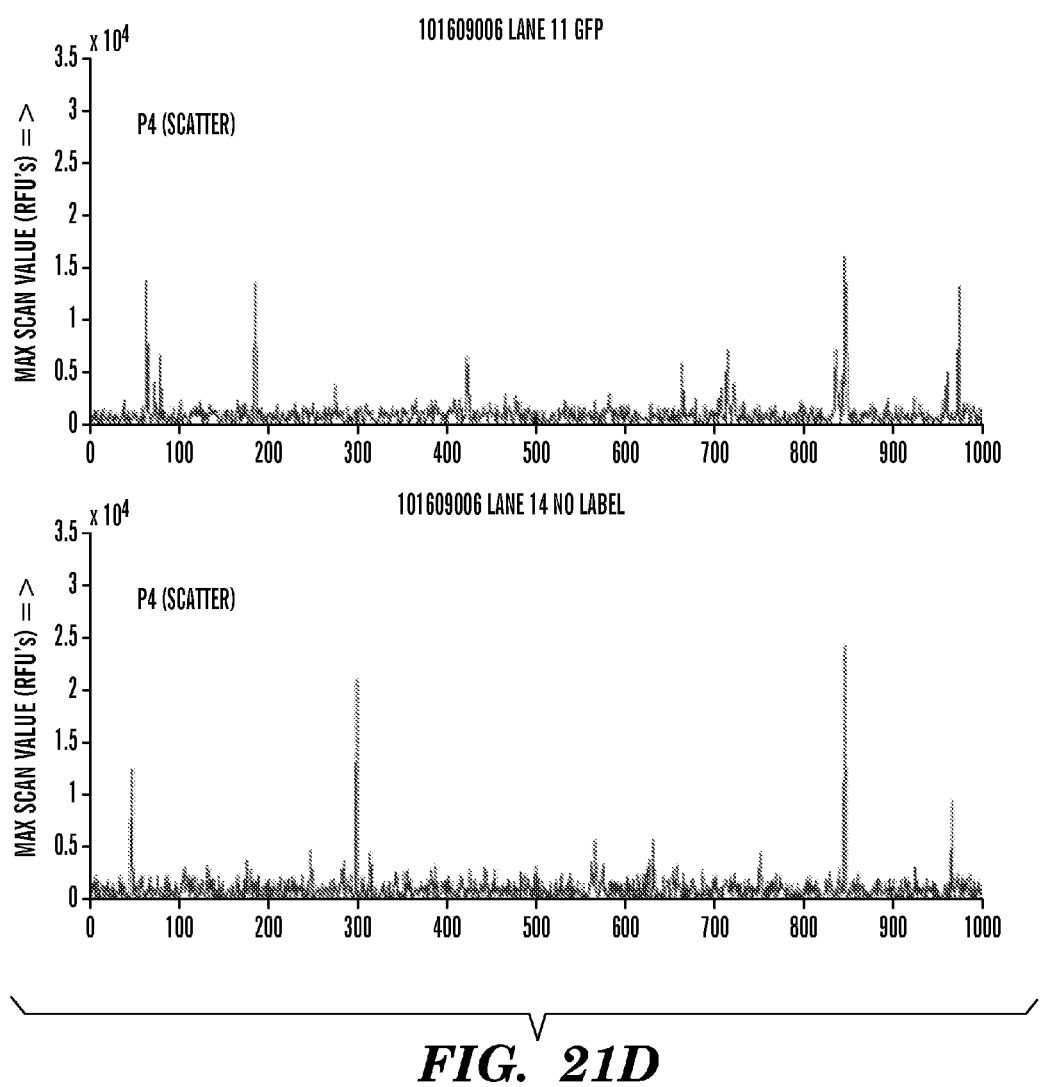
Figure 22A:
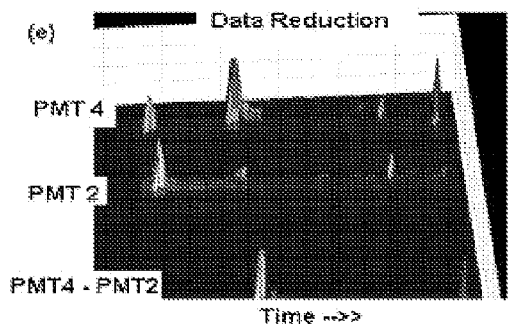
FIGS. 22A-22B show exemplary unreduced image data. Raw data (e.g., from FIG. 21) is plotted as an image of the microfluidic channel cross-section (vertical axis labeled spinner position) versus time (FIG. 22A)
Figure 22B:
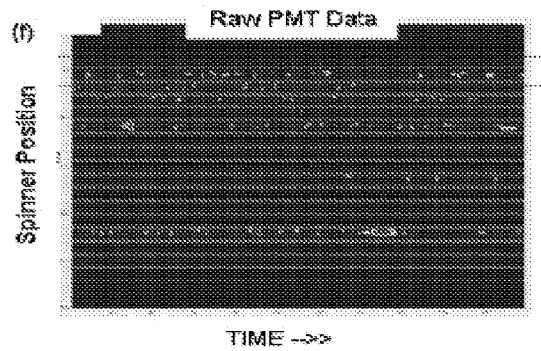
Figure 23:
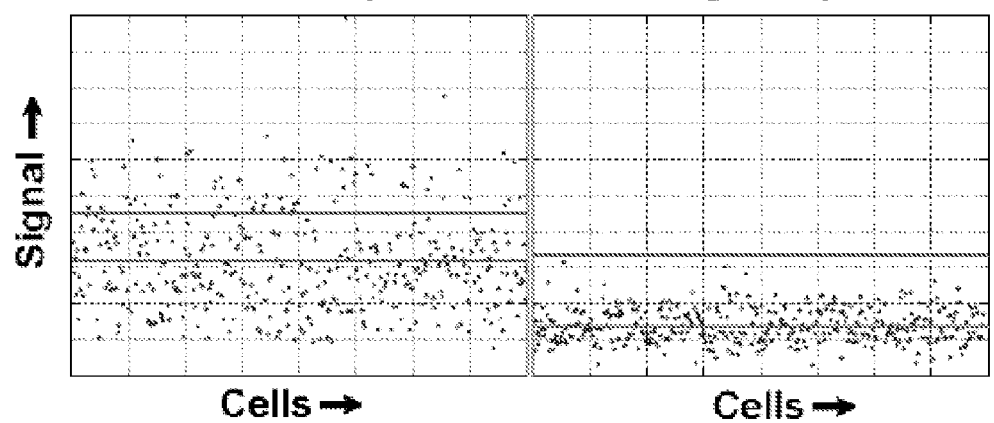
FIG. 23 shows graphs distinguishing positives from autofluorescence. A scatter-plot comparison of the ratio of the GFP channel to yellow channel for objects with a sufficient maximum GFP value (threshold) in positive and negative samples. The low ratio in the negative sample shows how autofluorescent cells can be rejected as negatives. By determining the mean and standard deviation for cells in the negative sample it is possible to calculate an outlier threshold (>mean+4 sd).
Figure 26:
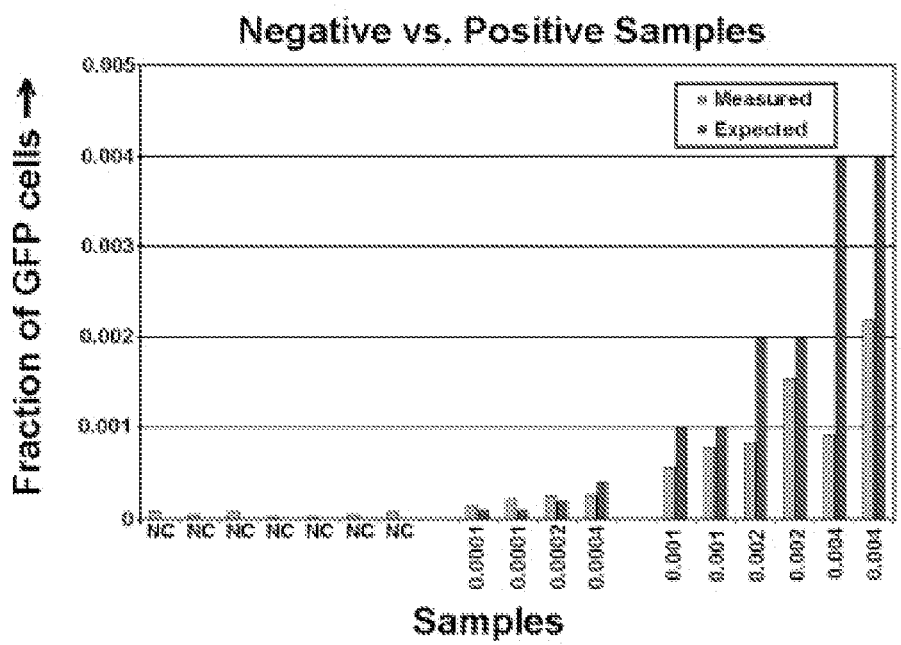
FIG. 26 shows results for a dilution study on primary splenocytes. Measured percentage and expected percentage of GFP labeled cells for all samples (ordered by expected percentage) shows a clear distinction between negative samples and positive samples down to dilutions of 0.01%. There is observable saturation of the count at high abundance (likely due to multiple-cell counts).

To understand how to design focusing devices the inventors explored low-Reynolds number, fully reversible, pressure-driven Stokes flow, in the geometry of FIG. 19 through two CFD simulation packages (Lin et al., *Biomicrofluidics* 3:014101-014112 (2009)). Based on the resulting models, simple three-level and four-level vertical focusing devices were constructed and tested for their performance via 3-D optical imaging in a confocal microscope (Lin et al., Biomicrofluidics 3:014101-014112 (2009)). The models show that the profile created by combining two flows in isotropically etched channels progresses nonlinearly as a function of the flow-rate ratio of the several fluid streams. That is, an addition of 50% fluid B to A does not give the same result as two sequential 25% additions of fluid B to A. Through comparison with experimental data, the inventors found that the models are highly accurate in predicting flow profiles.

Sorting A number of innovative microfluidic cell sorting devices have been designed and implemented on single-channel microfluidic cytometers. However, many of these single channel switches are difficult to multiplex, or lack the switching speed needed for a PMC. A parallel switch has been designed and implemented on a PMC by Bohm, Gilbert, and Deshpande (Bohm et al. U.S. Pat. No. 7,157,274). This system uses 144 parallel channels and a flow switch capable of a 0.5-ms activation cycle.

Line-Scan module: The present invention relates to a high throughput line scan module. Such a high content line scan imaging module can be configured to be used with a high flow cytometer (i.e. FACs module) for a high-content parallel flow cytometry. In some embodiments, the line scan module can also be configured to be used with HCS assays, for a single detection platform for high-throughput, high content (50-100 genes) screening based on line-scan imaging. For example, the high throughput line scan imaging module can be configured with a high capacity flow cytometer (i.e. a FACs module) and a HSC analysis module for a single detection platform, where the cells are (i) sorted (using the FACs module), then (ii) sorted based on image analysis (using the line scan image module) and (iii) analyzed using a HSC assay (i.e. multiplex QPCR module) for a high-throughput, high content (50-100 genes) screening based on line-scan imaging.

Although cell manipulations on microelectromechanical systems (MEMS) have been reported, there are no reports of parallel MEMS flow cytometry, except Quake et. al (Thorsen T, et al., *Science* 298: 580-584 (2002); Gomez-Sjoberg R, et al., *Anal. Chem.* 10.1021, 2005) and similar work in microchambers which report microfluidic Large Scale Integration. However, there are no reports that teach or mention how to perform large scale, high-throughput in-line scan imaging.

PMC Line-Scan Imaging on a DNA Sequencing System:

Herein the inventors have expanded the capability high content FACs, (i.e. a PMC (parallel microfluidic cytometer) by adding a line scan module which can perform 1-D and sparse 2-D imaging. For a feasibility, the inventors modified their previously developed BioMEMS-768 systems to reduce the spot size of the scanner to the extent possible (from 30-μm to 3.5-μm), (FIG. 3). Next, the inventors programmed the signal processing hardware to collect 100 points at 1-μm spacing across the channel. However, as the existing hardware had the limitation of processing pixels at a maximum 8,000 per second, the inventors overcame this restraint by limiting the range of the scanner to 320 data points at 1 μm resolution and 20 Hz. Flow was controlled by a Harvard Syringe pump with an 8 ml syringe.

The inventors utilized *S. cerevisiae* mutants engineered by the Lindquist Lab (Whitehead Institute) to overexpress the amyloid protein α-Synuclein (αSyn-GFP). In the native state, cells show a uniform distribution of the fusion protein along the membrane and in the cytoplasm. Under induction, the protein condenses to one or several focal conjugates per cell of 1-2 μm diameter. Cells were fixed and fluorescently labeled with a red whole cell dye. The samples contained a negative control with normally expressed α-Syn and positive sample with ~50% of cells were over expressing. Cells are fixed and suspended in PBS at a density of 1000 cells/μl.

A post-scan algorithm identified cells, created a Gaussian-smoothed image for each color channel then used various comparative color-channel algorithms to categorize images and identify cell metadata. FIG. 4 shows the raw traces for the red (580 nm) and the green (540 nm) color channels. These data were filtered to select a target diameter (red FWHM) of 4-6 μm, then an algorithm modelled after (two-dimensional) "roundness" was applied to the red and green channels. As shown in FIG. 4, the two populations are clearly distinguished. This was repeated for filters set to various signal X-widths. When we analysed some subgroups we were surprised to find that we could separate the positive and negative samples using some less obvious signatures. For example, for small-width thresholding (red FWHM) ~2 or 3 microns (after deconvolution of the laser spot), with strong red signal we found that green signal would occur over threshold in 5-20% of negative samples, but less then 1% of positive samples. The inventors indicate that this group represents scans that skirt the centre of the cell and that such scans often entirely miss the α-Syn-GFP focal conjugates. This is a novel indirect way to infer the condensed-state positive.

The inventors determined that while the modified DNA detector was able to prove HCS, this detector was partially unsuitable due to there being not a have sufficient data throughput or spatial resolution for the accuracy of the high content analysis for line-imaging. Thus, the inventors used a scanner with 1-μm spatial resolution, which is 20 times increased throughput which can be used in conjunction with high content flow cytometry applications (i.e. with the PMC module as disclosed herein).

4. Vertical Hydrodynamic Focusing for Increased-Sensitivity PMC Flow Imaging: One-dimensional squeezing, in the plane of the flow network, is relatively easy to accomplish in MEMS by using T-junctions (Li, P. and Harrison, *J. Anal. Chem.* 69, 1564-1568, 1997; Fu. A., et al., *Nat. Biotechnol.,* 17, 1109-1111, 1999; Perroud, T. D., et al., *Anal. Chem.* 80, 6365-6372 2008; Emmelkamp, J., et al., *Electrophoresis* 25, 3740-3745, 2004). However "vertical" hydrodynamic focusing is needed for our application. For example, at the 0.5-NA characteristic of a 40× microscope objective the total depth of focus (visible light) is on the order of 5 μm.

The inventors previously demonstrated microdevices for vertical hydrodynamic focusing through simulation and through direct experimental verification using a confocal microscope and a novel form of stroboscopic imaging (see e.g., Lin A, et al., *Biomicrofluidics* 3, 014101-014112, 2009, which is incorporated herein in its entirety by reference). By combining multiple crossing junctions (FIG. 5), the inventors demonstrated it was possible to confine cells to a single analytic layer of interest. In Cartas 2009 (Cartas, M-A. Masters Thesis in mechanical engineering, MIT 2008), the inventors previously demonstrated further design improvements, including a first integration of a fast piezoelectric microswitch (Lee Co.) into the device for cell sorting.

Development of the line-scan imaging module is divided into Example 2: algorithm-building, Example 3: sensor-design and, Example 4: testing/assay-building. The inventors demonstrate a line-scan imaging module which can be used for high throughput analysis of cells as a HCS (high content screening) method. The line scan imaging module can be used in a variety of methods, exemplary methods include 1) a protein localization assay for combinatorial studies related to diseases such as e.g. Parkinson's disease (e.g. a yeast model is used herein as an exemplary model), and 2) NF-kB nuclear translocation in hematopoietic stem cells (mouse).

The current solution for imaging in HCS is automated wide-field microscopy, which has limited use for least three reasons; (i) it has no separation (sorting) ability, (ii) throughput speed is severely limited by hardware and, (iii) microscopy can actually gather too much image information. Microscope-based systems are generally hardware-limited by autofocus; but when they are not, and when full 2-D images are gathered, intermediate buffering and long-term storage quickly clog the data stream. Technical imaging can throw more money than consumer cameras at buffering and storage, but still 2-D high-depth imaging rapidly requires cumbersome storage requirements and then cascades into clumsy data extraction. Furthermore, excessively rich 2-D image complicates the next stage of cytometry, i.e. the algorithm needed to provide assays out of raw data.

The line-scan imaging module developed by the inventors herein address these issues by taking approximately 1/1000 the amount of data per image. This drastically reduces the data-buffering and storage requirements and can simplify the classification algorithm. Most importantly, data acquisition and processing can become quick enough to become a trigger for a sorting device with significant throughput. While one potential disadvantage of 1-D imaging would logically be that with the sparser 1-D image, one might have to discard more "ambiguous" images. However, 2-D imaging also has its problems with ambiguous images, principally "out-of-focus" images (which the inventors avoid through confocal optics (discussed in more detail below). Thus, the inventors developed and optimized the line-scan imaging module to address the following research questions: "how well can we do in classify cell phenotype with line-scan images?" or "How well can we do in generating full cell assays with this reduced information content?" The inventors systematically provide the data that answers these questions. The inventors optimized the line-scan image module to distinguish features obtainable in several variants of line-scan imaging on typical live and fixed cell types. Embodiments of the line-scan imaging module can be combined with other high-throughput microfluidic modules (such as the high content screening modules as disclosed herein) to develop new high-throughput assays. The inventors also developed an expandable detector module with the required color separation and spatial resolution effective image distinction of the cells.

Line-scan imaging can be implemented in one form or another on (i) a conventional single-channel cytometer or (ii) a parallel microfluidic cytometer (PMC). For a single-channel cytometer, line-scan imaging could be accomplished by simply pushing up the spatial resolution of the fixed detector (assuming very good flow velocity controls), by adding a scanner, by adding a linear array and strobe illumination, or (our new idea) temporal encoding. The inventors demonstrate the line-scan image module configured to be used with a PMC (rather than single-channel) because this choice forces the issue of a parallel imaging system. Additionally, the PMC has potential for time-synchronized cytometry and down-stream expression analysis, well beyond the capabilities of single-channel FACS.

Example 2

Algorithms that distinguish common protein location patterns in live and fixed cells using line-scan imaging. As the cells flow through the microdevice they cross over the detection window where a scanner is moving (e.g., every 1/100 of a second) and recording emitted fluorescence values every 1 μm across the 100-μm-wide channels. The fluorescence values recorded by the separate PMT's are then converted to 16-bit digital values and sent to the computer where they are assembled in computer memory as 10 line-scan images per cell (hardware below, Sect. Example 3).

Once the system has determined that a cell has just passed over the line-scanner, the pixel matrix that represents that cell is sent to a cell-typing algorithm. This assay-specific algorithm measures features about the cell using the florescence levels from PMT's individually and in comparison to each other (Table 1). Feature values from the algorithm will be calculated in microseconds, allowing the cell to be identified while located within the flow. One outcome would be to trigger select/de-select element of a cell sorter (Li, P. and Harrison, *J. Anal. Chem.* 69, 1564-1568, 1997; Fu. A., et al., *Nat. Biotechnol.,* 17, 1109-1111, 1999; Perroud, T. D., et al., *Anal. Chem.* 80, 6365-6372 2008; Emmelkamp, J., et al., *Electrophoresis* 25, 3740-3745, 2004). The cell values are also saved to the computer where they can be used for statistical evaluation of all the cells in the sample.

Example 2.1

Classification by 1-D images: The inventors developed line-scan imaging algorithms for high-throughput, high-content image-based screening. Microscope-based (imaging) assays provide higher content than can be obtained by un-resolved total fluorescence, i.e., FACS. A key aspect for fluorescence localization assays will be fast image-analysis algorithms for binning of events. The economy of "line-scan" images (when compared to CCD images) is a computational advantage (Gonzales, R. C and Woods, R. E., Digital Image Processing, Prentice Hall, Upper Saddle N.J., 2002). The inventors prove the robustness of these "more economical" scans.

Figures 5A, 5B:
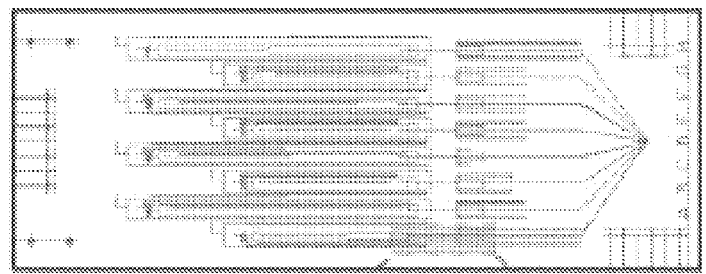
FIGS. 5A-5B show a schematic drawing of one embodiment of a plan view layout of a device designed for vertical hydrodynamic focusing, including subtractive compensation.
Figure 6A:
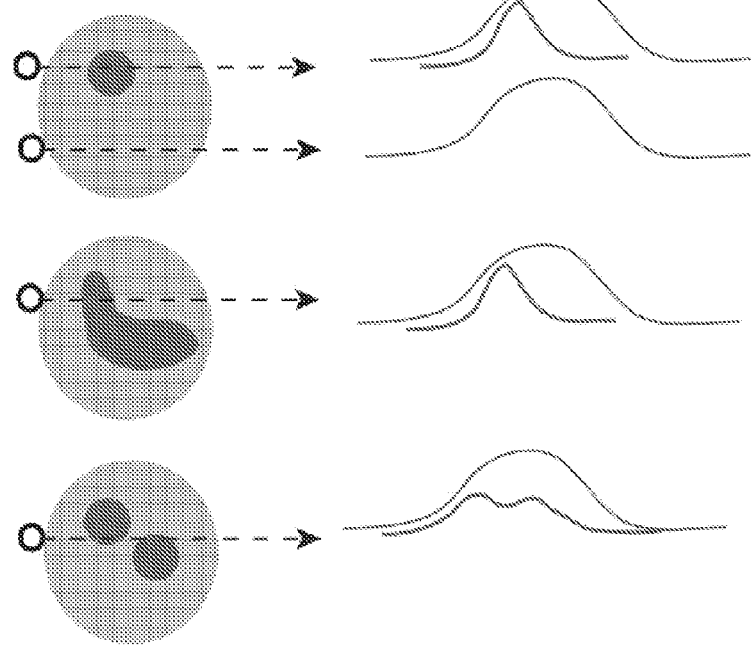
FIGS. 6A-6C are schematic cartoons showing typical line-scan images that are encountered in a protein localization assay. The left column shows 2-D (microscope) images with the marker (green) and cytoplasm (pink).
Figure 6B:
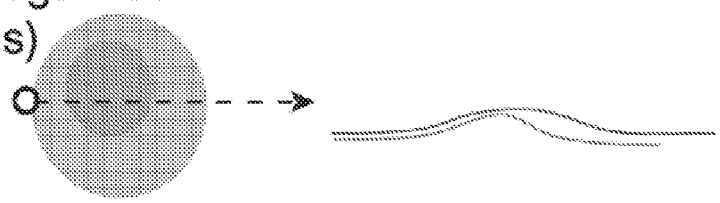
Figure 6C:
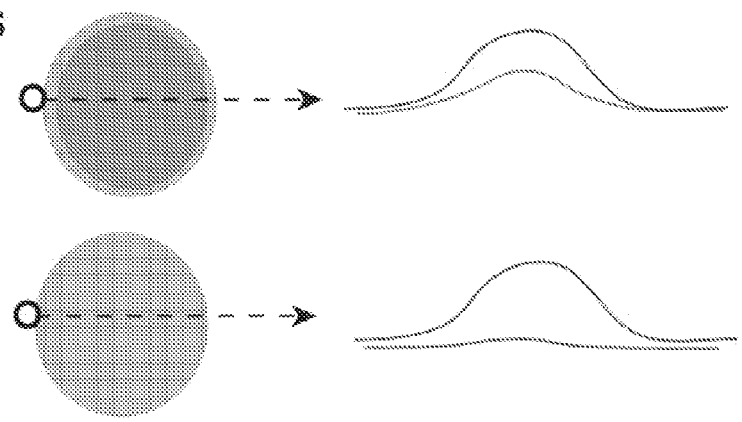

The classification ambiguity typical from 1-D imaging and as it relates to a protein-localization assay is illustrated for 2-colors in FIG. 6. By extracting only 1-D images, the feature set is greatly reduced with new classes of ambiguity relative to a conventional 2-D image; distinguishing features become asymmetries, profile shape factors, and relative curve heights. However, there is a great deal of information available even in 1-D; furthermore in the system developed by the inventors, there is up to 10 different line-images for each cell (5 colors reported separately for each of two lasers). FIG. 5 also illustrates phenotype classification in 1-D imaging system, and depends on if it is easier or harder with higher resolution (smaller laser spot) in the scan. More detail is not necessarily better for quick phenotype classification.

TABLE 1

Some image features available for measure by various assay methods.
Table 1 states the first step as a "'segmentation" problem.

| Cell Feature | Flow Cytometer | 1D line-scan | 2D line-scan | Microscopy |
|---|---|---|---|---|
| Red Dye Present | ✓ | ✓ | ✓ | ✓ |
| Blue Dye Present | ✓ | ✓ | ✓ | ✓ |
| Green Dye Present | ✓ | ✓ | ✓ | ✓ |
| Yellow Dye Present | ✓ | ✓ | ✓ | ✓ |
| Nucleus Area | | ✓ | ✓ | ✓ |
| Nucleus Eccentricity | | | ✓ | ✓ |
| Nucleus Perimeter | | | ✓ | ✓ |
| Nucleus Shape Factor | | | ✓ | ✓ |
| Nucleus Total Intensity | | ✓ | ✓ | ✓ |
| Nucleus Avg Intensity | | | ✓ | ✓ |
| Nucleus Intensity Var. | | | ✓ | ✓ |
| Nucleus Cenroid Offset | | ✓ | ✓ | ✓ |
| Cytoplasm Area | | ✓ | ✓ | ✓ |
| Cytoplasm Eccentricity | | | ✓ | ✓ |
| Cytoplasm Perimeter | | | ✓ | ✓ |
| Cytoplasm Shape Factor | | | ✓ | ✓ |
| Cytoplasm Total Intensity | | ✓ | ✓ | ✓ |
| Cytoplasm Avg Intensity | | | ✓ | ✓ |
| Cytoplasm Intensity Var. | | | ✓ | ✓ |
| Target Area | | ✓ | ✓ | ✓ |
| Target Total Intensity | | ✓ | ✓ | ✓ |
| Target Avg Intensity | | | ✓ | ✓ |

The inventors next modeled various forms of multicolor line-scan images from typical cells and to then partition them into the "positives" and "negatives" typical of a cell assay. The problem is complicated by the several trade-off choices in the optical system and the illumination. In addition, a real assay sample will contain both positives and negatives. The cell types are on a continuum of size/shape/cell-cycle factors which causes a heterogeneous distribution of line-scan images. The exact position of cells in the Z-focus is a complicating factor for all imaging methods (although it is minimized for a confocal detector). The traditional way to approach these problems, all of which are also encountered in CCD imaging, is to set up data filters and thresholds that eliminate ambiguous data. The inventors used the same approach, however the algorithms and filters will be unique to line-scan imaging (e.g., both imaging intracellularly and/or gross imaging of the entire cell to determine the presence of one or more fluorescent markers). The metrics of success are partitioning confidence factor (for example, the Students T test) and the sampling efficiency (as measured in time per assay). For a simple binary (yes/no) assay the number of discriminating (qualified) objects is theoretically as few as 50-100 objects (Taylor, D. L., Haskins, et al., High Content Screening, Humana Press, Totowa N.J. 2007). Therefore since many thousand events per second can often be processed, it is possible to "throw away" a large number of the events and still end up with a fast high-confidence assay.

The inventors addressed this problem with a combination of empirical modeling and data reduction from data libraries and from specifically acquired 2-D and 1-D images. The inventors used large databases of CCD images at BU and MIT. The inventors also construct and characterize a line-scan imager (Example 3, below). This date was then compared to actual data as acquired on real live and fixed-cell samples (data not shown) to confirm the models and, conversely, the models depend on optics choices. There are a number of hardware adjustables in the specific embodiment of the line-scan module developed and configured in Example 3 (e.g. embodiments with different resolution, filter choices, illumination etc.); each embodiment being tested with the model guiding the adjustment of hardware and the measured performance of the hardware guiding the refined model.

Example 2.2

"Structured" Illumination: In line-scan imaging, there is one scanned dimension per image; there can still be many choices in the transverse shape of the illumination pattern that is scanned through the cell. It is also possible to analyze a phase pattern, which can lead to phase contrast (e.g., DIC).

For one dimension, the one perpendicular to the scan, the inventors used the order of 1-2 micrometers in order to resolve the protein localization currently used in high-content assays. If the (Y) dimension of illumination perpendicular to the scan is extended, then more fluid volume is sampled per scan. The available brightness of the source (expressed as signal-to-noise ratio, S/N) will create an optimal Y ellipticity. The fill factor of the objective and the confocal slit width affect the sampling volume in the Z direction. In general it may be preferred to restrict Z to several microns. In one embodiment of the hardware iteration (below), the inventors used a single-cathode PMTs for each color channel. Therefore this first detector would not use the potential intensity and phase information that is available in the Y dimension. In different embodiments, these sensors could be replaced with multi-cathode PMTs (or linear avalanche photodiode arrays (APDs), so as to gather this intensity or phase information in the Y direction. For a typical 10-µm-diameter cell and 1- or 2-µm resolution such an array detector would provide 4-10 Y pixels. However, patterned illumination with linear extension into the Y direction is also encompassed in some embodiments, as well as possibly with 4-10 Y pixels at the sensor. In some embodiments, a 2-D line imaging system can be used. This degree of 2-dimensionality in the line-scan images does not contradict the previous arguments about the advantages of line-scan imaging over wide field microscopy (smaller data files).

Example 2.3

Stimulated Emission or Non-linear Imaging: In some embodiments, pulsed (e.g., femtosecond) sources can be used in the multi-source module as disclosed herein (Example 3). In some embodiments, line-scan imaging can implement sub-diffraction methods such as stimulated emission imaging or multiphoton imaging. This is of high scientific interest, however higher resolution may not be important to achieve productive cell assays. The inventors used an embodiment with the 0.5-NA Optem objective (below) to achieve diffraction-limited spatial resolution near 0.5-µm (Rayleigh), which is a comfortable factor beyond the stated 1-μm goal, before exploring non-linear methods.

Example 2.4

Time-Encoded 2-D Line-Scan Imaging: In one embodiment, the inventors use a detection system with low-complexity 2-D image in line scanning is illustrated in FIG. 8. In such an embodiment, instead of a single-source, in this embodiment an independently modulated linear-array (e.g., Intense LTD, INSlam) is scanned perpendicular to the flow direction (array axis parallel to the flow direction). Each source in the array is given a unique temporal code. For each color channel, the signals are collected on a single detector, and are de-multiplexed (as for fiber communications) according to their temporal codes. The 2-D image is reconstructed by assigning each source (Y in the image) and scan-clock (X in the image).

Since the typical signal integration time for each X point will typically be ~10-100 μs/cell-image, the encoding modulation should ideally be at MHz frequencies. However this is not a problem as print heads employ independent-channel modulation at 200-300 MHz. The detailed methods of spatial encoding signals can be borrowed from the many approaches used in communications (Agarwal, G. P., Fiber-Optic Communication Systems, Wiley-Interscience, 2002; Wada, N. and Kitayama, K. *J. Lightwave Technol.* 17, 1758-1763, 1999). In some embodiments, one option would be use of time-encoded imaging for adding (unscanned) imaging to a commercial single-channel cytometer (see Example 3.3).

As described in a section below, the inventors assessed time-multiplexed imaging at the minimum complexity of a 22-emitter array, 630-650 nm wavelength. (INSlam-GWI, Intense Corp. Glasgow, Scotland or similar). This array is available on 20-μm centers, so the inventors de-magnified it by 10× to achieve a 2-μm resolution in the direction perpendicular to flow (Y), (see Example 3) to achieve a nominal 5×5 pixel image for a 10-μm dia. cell.

Therefore, the inventors demonstrate one embodiment of the line-scan module which uses simple 2-D images at the complexity of 5×5 images. This results in a file size that does not clog data buffering or storage. The inventors demonstrated using BU and MIT library images for the exercise and simulate images and test simple 2-D image-classification algorithms. The inventors assessed if the efficiency of phenotype classification was significantly improved for a 5×5 2-D image relative to a 5×1 1-D image (data not shown), and if it is worth the additional complexity to implement 2-D line scanning over single-source 1-D line scanning (data not shown).

Example 2.5

Sample Heterogeneity: In a typical real case the absolute magnitude of expression level in two fusion proteins used as markers varies over a large factor. The protein localization patterns are also highly varied in the positive sample, and there is significant noise in the images on the scale of features of interest. In a flow system there is less complexity due to the serial presentation of cells (nearly no overlapping of images), although there is also get less information. The line-scan imaging modules models were optimized on real samples over the range of culture conditions specific to each experiment. The inventors demonstrate some experiments using the line-scan image module on primary cells from mouse carcinomas. (The reduced sample size required on a PMC versus a FACS is a big advantage for such cases (Mckenna B K, et al., *Lab on a Chip* 9, 305-310, 2009). With good specific markers it is certainly possible to construct a good assay. However, each cell type and experiment is likely to require adjustment of data filters and the adjustable parameters of each algorithm. The inventors developed an line-scan module which can be easily adjusted with different embodiments, such as template filters and use with different algorithms, to make these customizable with a minimum number of adjustments, and to develop standard operating procedures to find the optimum parameters to plug into the new filters.

Example 2.6

Real-Time Algorithms: Microscope (2-D) image data is typically post-processed without specific time pressure. For the PMC, the inventors sorted cells in the flow with a parallel MEMS switch. Since the cell of interest will only remain in a well-known volume for a short period (ms) the image recognition and algorithm needs to complete a decision in microseconds. Ideally line-scan algorithms would be retrofitable to sorting on a conventional flow cytometer (e.g., a Beckton-Dickinson instrument).

Example 2.7

Difference between 2-D and 1-D image algorithms: The inventors have previously developed 2-D image algorithms for HCS. However, 1-D algorithms as fundamentally different due to the following: (i) directed 2-D algorithms start by drawing boundaries around "primary and secondary objects" (also called "segmentation"). In a 1-D system the inventors set the resolution in hardware (the optical system), to an intermediate range (1-3 μm dia.), and eliminated boundary drawing by accepting any resolution element as an "object". (2) The inventors performed careful quantitate fluorescence (see below, first prototype will have an embodiment with 10 image channels, and much more effective bit depth than a wide-field image due to confocal rejection). For 2-D algorithms the computational and "judgment" aspects of drawing object boundaries is a big source of assay variability, and is considered the "most challenging" step. The new algorithms will make more use of color-ratio and texture in the 1-D scan. This aspect makes clear the reasons for selecting a large enough resolution element to do good signal averaging, but a small enough one to subdivide the 1-D cell image. Specifically, maximum resolution is not desired as this implies a weak signal and lower signal-to-noise ratio in the color channels. In a separate comparison, the inventors have already shown (see e.g., Mckenna B K, et al., *Lab on a Chip* 9, 305-310, 2009, which is incorporated herein in its entirety by reference) that a much higher signal-to-noise ratio in a PMC as compared to a FACS. Therefore the optical system should be tuned for intermediate spatial resolution, high signal-to-noise, and phenotypes will be inferred from careful channel-ratioing and texture. In some embodiments, the inventors purposely reduced the number of distinct image types (in the hardware) to make this process time efficient, and for most part to avoid the need for boundary drawing (segmentation).

Example 2.8

Development Tools for Image Analysis. Development tools for image analysis are MatLab, MetaMorph, ImagePro and Axiovision. Alternatively, image analysis can be performed using shareware 2-D image analysis software including Image)/NIH and CellProfiler.

Example 2.9

Hardware Characterizations needed for Algorithm Trials

Example 2.9.1

First characterize the optical system using beads (multi-color):

The first step is to characterize the optical system, which has adjustable elements in both the illumination and the fluorescence return optical path (Example 3 below). The best way to do this is with sub-resolution fluorescent beads. The inventors varied the telescope parameters on the input lasers, the confocal slit, and the focus conditions. The inventors also used the "knife-edge" test (Born and Wolfe, 2002) and reflected light with a chrome photomask as an effective image analysis tool. The end results in in-focus (point spread function) and out-of-focus bead images. This information becomes the starting point needed to develop deconvolution. The latter techniques then can be modeled after deconvolution in 2-D microscopy, however they will be simplified in the 1-D cases.

To collect the point spread focus series, the inventors used 200-nm-diameter fluorescent beads on a glass slide (unbonded 0.7-mm-thick plate@PMC channel focus). This slide will be moved in 100-nm increments in X,Y, Z using a small piezoelectric stage and single-bead images will be acquired and analyzed.

Example 2.9.2

Simulated expected line-scan images from Cellomics 2-D images. Design and iteratively test new line-scan image metrics: With the input of the system point spread functions at different optics settings, the inventors then simulates expected 1-D line scan images using empirical images off of a Cellomics or similar microscope system. Cellomics was used to provide the raw files that are needed for this. Simulation becomes a powerful tool for decisions on the adjustment of the optics. The Cellomics images from the specific samples (yeast and mammalian cells), which can be used to simulate 1-D spectral profiles and test/grade experimental 1-D algorithms in their efficiency to correctly separate phenotypes. Images will then be collected on the 1-D scanner using the same cell samples, and the algorithm design process will be iterated.

Example 2.10

Line-Scan Trials. Image-based sample partitioning on *S. cerevisiae* and mammalian cells to show protein localization in live and fixed cells: The inventors conducted experiments at 3-4 μm resolution from a single 384-well plate (α-Syn/GFP in *S. cerevisiae*, fixed cells). Even within a single 384-well plate, the inventors demonstrate see reproducible differences between wells (depending on modifier conditions). Using the improved software (Example sections 3.1-3.9), the inventors can gather data from 4-6 plates (per iteration), each plate cultured separately in order to understand the overall statistical robustness of the assay. This analysis enables validation of specific image algorithms within the statistical noise of within-run and between-run variation.

Finally, the inventors challenged the productivity of the overall assay by taking time-course and dose-response measurements with live cells. Detection variability is determined by calculating coefficient of variation for sampling of identical (fixed) samples. Assay reproducibility is determined by measuring the overlay accuracy of time-coarse plots, and by calculating the coefficient of variation between IC50 dose points from multiples out of a 384-well plate. The last metric that is needed is the sampling number that is required for statistical significance. This is estimated by two-way analysis of variance with stimulated and un-stimulated cell samples.

Full validation will consist modified forms of a "3-day Plate Uniformity study" and a "Replicate-Experiment study" (http://www.ncgc.nih.gov/guidance). The standard "Inter-leaved-Signal" plate study will be customized by superimposing an Interleaved-Channel Study (to test across the multilane microfluidic) with similar pass criteria to those published at the NIH Chemical Genomics Center web site (see web site for parameter definitions and detail):

Acceptance Criteria. The overall requirement is that the raw signals are sufficiently tight and that there is sufficient separation between the max and min signals to conduct screening. Calculations and acceptance criteria are:

(1) The outliers (identified with modified Tukey's rule) should be "obvious", and the rate of outliers should be less than 2 percent.

(2) Compute the mean (AVG), SD, and CV (of the mean) for each signal (max, mid, min) on each plate. The acceptance criterion are that the CV's of each signal be less than or equal to 20%, except for the min signal is $SD_{min} \leq$ both $SD_{mid}$ and $SD_{max}$. All plates should pass all signal criteria (i.e., all Max and Mid signals should have CV's less than 20% and all Min signals should either pass the CV criteria or all Min signals should pass the SD criteria).

(3) For each of the mid-signal wells, compute a percent activity for agonist or stimulation assay relative to the means of the max and min signals on that plate. For inhibition assays compute percent inhibition for each mid-signal well, where % Inhibition=100−% Activity.

(4) Compute the mean and SD for the mid-signal percent activity values on each plate. The acceptance criterion is SDmid ≤20 on all plates.

(4) Compute a Signal Window (SW) or Z' factor (Z') for each plate, as described below. The acceptance criterion SW≥2 or Z'≥0.4 on all plates (either all SW's≥2 or all Z'≥0.4).

(5) Intra-plate (and Intra-Channel) Tests: Each plate/channel should have a $CV_{max}$ and $CV_{mid} \leq 20\%$, $CV_{min} \leq 20\%$ or $SD_{min} \leq_{min}(SD_{mid}, SD_{max})$, Normalized $SD_{mid} \leq 20$, SW≥2 or Z'≥0.4.

(5) No material edge, drift or other spatial effects.

(6) Inter-plate and Inter-Day Tests: The normalized average mid-signal should not translate into a fold shift >2 within days, >2 across any two days.

Example 3

In Example 3, the inventors demonstrate preliminary line-scan imaging with a modification of the DNA sequencing detector. This detector was designed for column detection (originally a 30-μm-laser spot), reduced to 3.5 μm for Example 3, but is not sufficient for a real test of line-scan imaging. Thus, the inventors rebuilt the sensor for the cytometry application.

Example 3.1

Scanning detector: A parallel-channel optical scanning optical system with the following performance:

(1) five-color detection, for each of 2-laser excitation wavelengths (expandable to 8-color detection, 4-lasers). Adjustable to cascade architecture with a dynamic range of 1 million. (2) chromatic correction, 1 micron Rayleigh Resolution, slit-confocal stray-light rejection (3) suitable for 32 parallel fluidic lanes, and desktop size.

Such a "scalable" module can be a building block for multichannel (384-lane) imaging cytometry and also for the high-dynamic range expression analysis (Ueberfeld J, et al., *Analytical Chemistry*, 80, 7430-7436 (2008); Ueberfeld, J. and Ehrlich, D. J. *Electrophoresis*, (in Press 2009)) on retained fractions.

Figure 9:
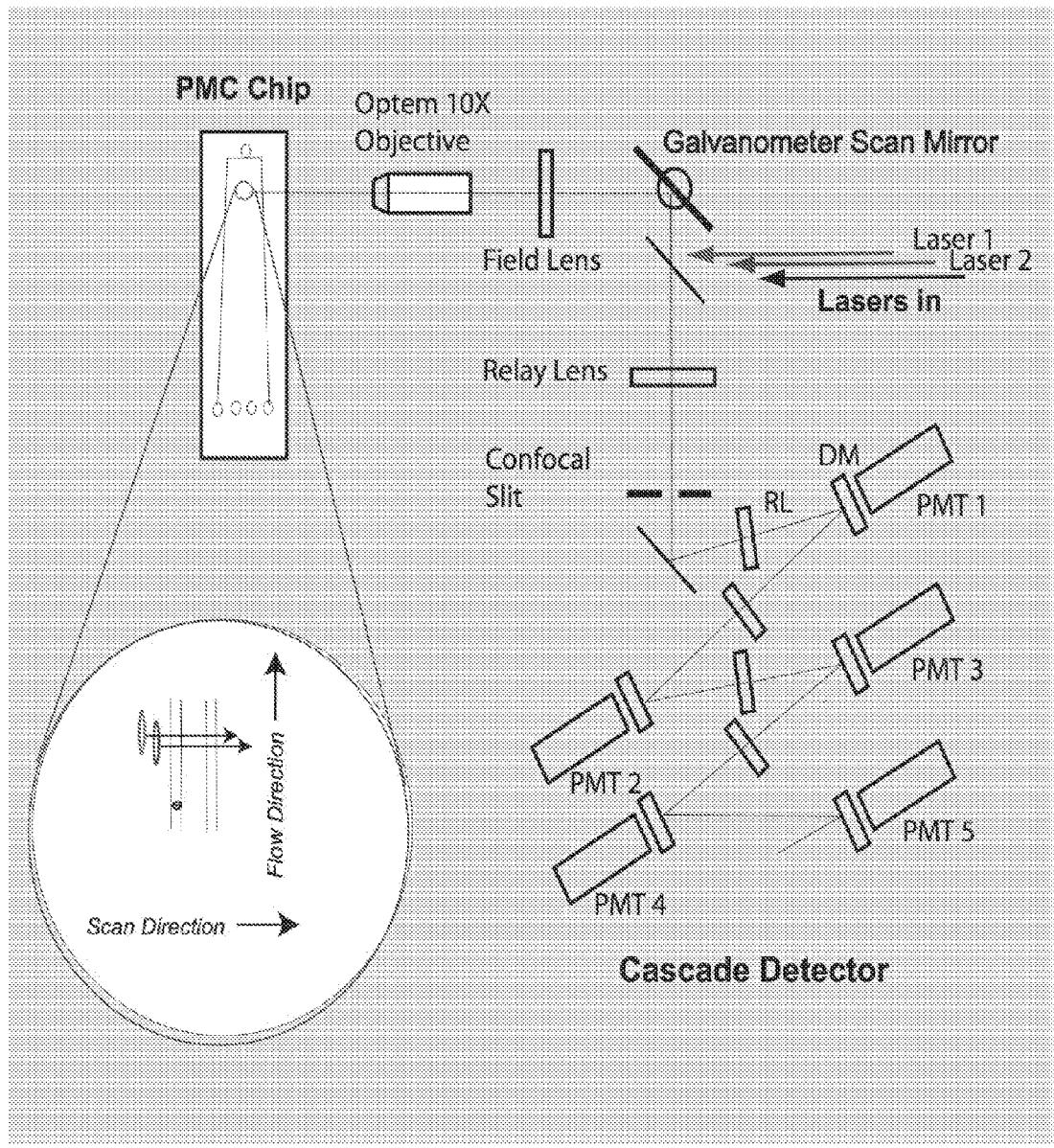
FIG. 9 is a schematic image of one embodiment showing a scalable test line scan image module for development of line-scan imaging. Shown in this embodiment is a line scan image module for single-point photomultiplier (PMT) 1-D imaging; however the PMTs can be replaced by linear-array detectors or multi-cathode PMTs to achieve low-complexity 2-D line-scan imaging, still with confocal slit rejection. Dichroic mirrors (DM) and relay lenses (RL) are used in a cascade. The embodiment can be configured to connect this line scan image module for 32-channel microfluidics (see FIG. 11). In some embodiments, additional lasers, color channels and fluidic channels can be added without changing the architecture of this embodiment of the module. The Optem 10× objective can also be replaced with specialized (e.g. Nomarski) objectives.

A fusion of the LIF detectors that we have built for previous NIH and the NIJ column instruments is illustrated in FIG. 9. This detector used in the Example 5 was built to scan mesoscale Sanger sequencing plates (FIGS. 1A and 1B), (El-Difrawy S A, et al., *Rev Sci Instrum* 76(7):074301 (2005)) and is limited by a molded aspheric objective, and by obsolete digitizing electronics (in our prototype 16 kHz digitization, circa 1998). Another (galvanometer-based) scanner was developed for the NIJ, is now fielded widely for DNA forensics (Network BioSystems Inc.), and was also used in the RTPCR application for high-dynamic-range expression analysis from less than 10 cells (Ueberfeld J, et al., *Analytical Chemistry*, 80, 7430-7436 (2008); Ueberfeld, J. and Ehrlich, D. J. *Electrophoresis*, (in Press 2009)). This second detector has a highly corrected objective. Therefore, the inventors used it as a starting point (FIG. 9) with multi-laser excitation on an expandable photomultiplier (PMT) cascade and modern digitizing electronics.

The inventors added a slit-confocal stray light rejection and recorded color-channel images on (initially) five PMTs for each of two lasers (red and green) that are scanned with a short time delay (~10 ms) over 32 flow channels. The output is therefore multiplexed on a minimum number (five) PMTs, but is time multiplexed so that each "event" (i.e. cell) produces 10 line-scan images. These 10 images can then be used to construct phenotype signatures. The inventors have previously demonstrated 10-pM fluorescein sensitivity in comparable systems (Goedecke N, et al., *Electrophoresis* 25(10-11): 1678-1686 (2004)). Mainframe commercial FACS machines typically duplicate the entire PMT system for each additional laser. In some embodiments, the invention herein is more economical in parts, should become desktop size, and can be expanded to more sources and sensors as needed. Details are given below (see Examples 3.1.1-3.1.9):

Example 3.1.1

Astigmatic focus: The inventors used astigmatic telescopes on each laser source to extend the laser source to an adjustable aspect ratio between 3/1 and 30/1. This is possible without compromising the narrow (1-µm) spot dimension. (Extreme examples of this, e.g., line-generators used in grocery store scanners achieve nearly 1000/1 aspect ratio.) An elongated spot shape allows an increased flow (count) rate without much penalty in 1-D resolution.

Example 3.1.2

Galvanometer Scanner: The inventors used a one-dimensional galvanometer scanner (General Scanning, CRS and M-Series) for open-loop and closed-loop scanning perpendicular to the flow direction. The inventors have previously used these devices in two commercial semiconductor instruments. The relay optics to create stationary images in the back focus of the objective and at the slit can be taken from the NU design.

Example 3.1.3

Time multiplexing of laser scan: Two (or more) laser beams are introduced as separated spots (FIG. 10) but sufficiently adjacent so that both spots will sequentially scan though individual cells. At typical scan velocities the time delay will be on the order of 10 us and the cell will move several microns or less between laser spots. The spots can be vertically (Y-dimension) displaced to compensate for movement, or with elongated laser spots (FIG. 10), no displacement is necessary.

In another variant of time multiplexing a temporally separated series of (ideally) identical multi-color ("strobe") images can be created by sending several reflections of a single-laser wavelength through the scanner. This is most easily done by using a parallel stack of partial reflectors. For example to get an off-set series of 4 images from a 488-nm laser two microscope slides are used in reflection at 45 degrees in the illumination path (FIG. 10). The four images from the four scanned beams can then be used to produce an "averaged" as opposed to "integrated" image. This is a standard way to separate background structure in noisy images.

Example 3.1.4

Objective lens: As an initial compromise in numerical aperture, working distance and field size the inventors used a well-corrected Optem Inc. 10×, 0.5 NA long-working-distance microscope objective.

Example 3.1.5

Laser Wavelengths: In one embodiment, the inventors use lasers at 488-nm and 405-nm and 633-nm in order to be optimized for GFP, the Cellomics nuclear translocation kit, and Luminex beads. The inventors can used additional lasers in different embodiments for excitation at 543-nm, and the deep-UV.

Example 3.1.6

Color Channels: The cascade detector channels (FIG. 9) are easily customized by changing out the dichroic beam splitters and band-pass filters. Two channels will be optimized as "backscatter" (whole-cell) signals at the two laser wavelengths; two additional channels will be initially optimized at the GFP and nuclear-stain channels. A transmitted-light (forward scatter) channel can be added with out great difficulty.

Example 3.1.7

Figure 11:
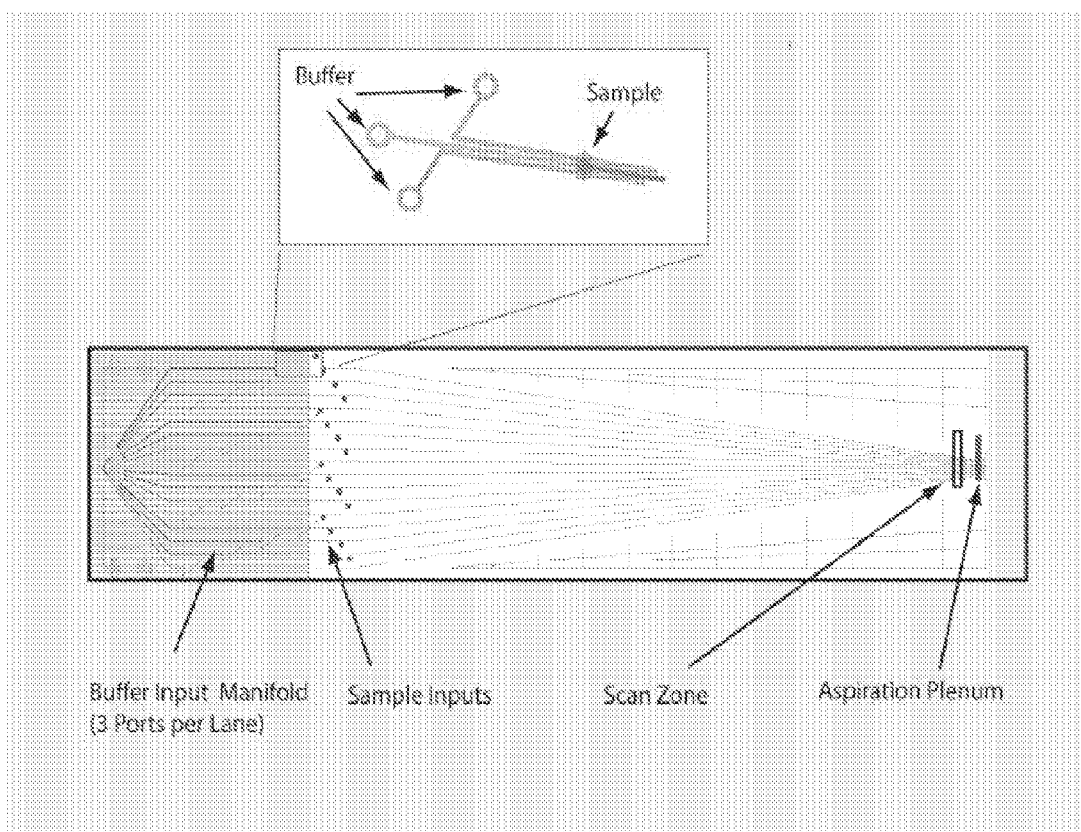
FIG. 11 shows one embodiment of the microfluidic device design. In this embodiment, overall dimensions are 25×100×1.4 mm, (note, half of 32 lanes are not shown for clarity). A layered symmetric sheath flow (blue) compresses a sample stream (orange, 16 middle inputs). Previous experiments show that Sigre-Silberman flow effects (due to the finite cell diameter, (Segre, G. and Silberberg, A. J. *Fluid Mech.* 14, 136-157, 1962)) cause centering of cells into a constant velocity stream in the center of each channel (Lin A, Hosoi A, and Ehrlich D J *Biomicrofluidics* 3, 014101-014112, 2009).The sheath flow and an iodated-gradient-density buoyancy additive are used to prevent cell settling (Selim A, et al., *J Bone Miner Res* 20 (suppl 1):S183 (2005)). The sample-well input array is set at 4.5-mm center-to-center spacing to be compatible with the pipetting robot. A positive displacement syringe pump attaches at the "aspiration plenum" to drive fluid flow toward the right. Elastomers (such as PDMS) are avoided except as gaskets, due to low maintainability and low rigidity.

Microfluidic Device: In one embodiment, the inventors implement the simple design illustrated in FIG. 11. This line-scan imaging device is conservative, adding only flow focusing (Lin A, et al., *Biomicrofluidics* 3, 014101-014112, 2009) to a previous PMC 32-lane design (See Example 5). This embodiment is compatible with automated pipettors for sample transfer (i.e. sample transfer to inlet sample wells or sample transfer from outlet sample wells (i.e. negative and positive sample wells)) of the microfluidic device. The inventors have developed a three-dimensional micromachining method (mechanically machined base/laminated cyclic polyolefin window, M. Cartas, PhD thesis, which is incorporated herein by reference) that can be used for sample transfer in a second-generation chip with stronger flow focusing. A significant advantage of this method is that it allows reversible bonding of devices with a optical window thin enough to match a cover slip (i.e., compatible with high-NA objectives).

Example 3.1.8

Channel Count: Determination of optimum fluidic channel count for a PMC.

In it's simplest form, the line-scan imager module as disclosed herein will stream its data (no matter how it is collected) through an analog-to-digital converter (ADC). The electronic data rate will most probably be limited by this subsystem and, in this limit, greater fluidic channel count does not increase data rate for the PMC (thus, the inventors can increase the flow rate in fewer channels). However, a bottleneck often occurs earlier in the system, and, importantly, a certain amount of parallelism is needed to get the benefits of (i) sample synchronism for kinetics, (ii) channel redundancy for replicate data (several lanes are used for each sample).

For small PMC channel count, the time budget of the pipettor is the most frequent bottleneck that comes into play to reduce throughput. For example, the load/purge/reload cycle needed by the pipettor can be on the order of a minute. For 384 samples, this would add 384 minutes to the operation of a single-lane chip. Therefore a minimum lane count of a 32 or 48, where a 32-tip or 48-tip automated pipettor can be put to good use, is generally needed for a reasonable match to the ADC-limited throughput. Most of the data in Examples 5 and 6 (Mckenna B K, et al., Lab on a Chip 9, 305-310, 2009) was collected on 384-lane chips with a 96-tip pipettor. This put this system close to the ADC-limited rate, since the pipettor cycle was a few minutes total for 384 lanes (total load/purge/reload cycle). For prototyping purposes, the inventors choose an embodiment of a simple 3 2-lane device that was less expensive to fabricate and which will still demonstrate the characteristics of a PMC. However, the device can be scaled up to include 384 lanes to be compatible with the 384-lane chips with a 96-tip pipettor and the parallel flow cytometer as disclosed in Example 5.

Example 3.1.9

Operating Conditions: Throughput, Scan Rate, and Sample Requirements

One embodiment of the line-scan image module has the following operating conditions:

Scanner: 10 Mhz Texas Instruments 1610 ADC (80 pixels/microfludic-channel),

1-D-Resolution/1 μm(X), Scan-rate/10-200 Hz,

Microdevice; 32 lanes, 100- to 200-μm wide, Sample-volume-per-scan/0.1 mL

Flow: Flow-rate-per-channel/1.2 μl-per-minute@200 Hz

Sample Requirement of Sensor: 2-μL/Sample@1000 cells/μL

The raw throughput is calculated to be 22 ea. 384 lane plates per hour for a binary assay, including the time required for the pipettor refresh cycle (30 s) and scanner turn-around time (20%). A calculation of the throughput limit determined by the 1610 ADC board is provided in Table 2. This only a guide, however our DNA sequencer (although with a now obsolete board) operates within 25% of the analogous limits that are projected in table 2.

TABLE 2

Trial operating parameters and throughput for the HCS PMC.

| Operating Parameters for PMC | 384 chip | 96 chip | 32 chip |
|---|---|---|---|
| Sampling-volume/channel/scan (μl) | 0.0001 | 0.0001 | 0.0001 |
| Cell Density (cells/μl) | 1000 | 1000 | 1000 |
| Scan Rate (scans/sec.) (Electronics Limited) | 16.3 | 65 | 195 |
| Cells/sec/microfluidic-channel | 1.63 | 6.5 | 19.5 |
| Flow Rate (μl/min/channel) | 0.0978 | 0.39 | 1.17 |
| Time required to get 1000 pts/channel (min.) | 10 | 3 | 1 |
| Sample volume needed for 1000 pts (μl) | 1 | 1 | 1 |
| Time required to get 200 pts/lane (min.) | 2.0 | 0.5 | 0.2 |
| Sample volume needed for 200 pts. (μl) | 0.2 | 0.2 | 0.2 |
| Number of Lanes | 384 | 96 | 32 |
| Wells per Hour | 2253 | 2246 | 2246 |
| 384-well Plates per Hour (1000 cells per sample) | 5.87 | 5.85 | 5.85 |
| 384-well Plates per Hour (200 cells per sample) | 29.3 | 29.3 | 29.3 |

A 10 Mhz TI 1610 ADC is used on each color channel, 80 pixels dedicated to each microfluidic channel, 100-μm-wide channel. The laser spot is 1 μm × 30 μm. These numbers are a guide only, used to plan the pipettor and scanner as well as the chip.

The inventors used a scanning (instead of fixed) detector as it reduced the requirements on flow uniformity. The scan velocity becomes mechanically controlled and is extremely reproducible, as opposed to being position-dependent in a Gaussian (pressure-driven flow) profile. However, the flow rates and cell density were adjusted so that a sufficiently high count-rate is achieved without many double-count (rejected) events. Hydrodynamic focusing was used for consistency of flow rate, to increase reproducibility of the time delay between laser-triggered fluorescence (FIG. 10). The inventors have previously demonstrated with both vertical and horizontal flow focusing with chips having up to eight lanes (Lin A, et al., *Biomicrofluidics* 3, 014101-014112, 2009). Lane-to-lane and laser-to-laser cross talk can lead to artifacts in the line-scan images. Thus, the inventors used a confocal slit which rejects the lane-to-lane artifacts efficiently. Additionally, laser-to-laser cross talk can be addressed by increasing the spatial separation of the laser spots, however, if this is done, it would also eventually require reduced flow rate. Commercial FACS machines generally reproduce the whole photomultiplier and objective optics when adding more than one laser (exact overlap of laser spots (x,y,z) would be required for a staring detector). By scanning in one dimension and time multiplexing we reduce these requirements, and avoid an expensive replication of hardware. However individual telescopes will be needed on each laser to adjust the collimation and for shaping the laser spot. Elongation increases count rate but reduces some line-scan image information and needs experimental testing.

Example 3.2

Line-Scan imaging device prototype Time-Encoded 2-D Line-Scan Imaging (FIG. 8): The inventors achieved 2-D line scan imaging by replacing the traditional PMTS in FIG. 9 with multicathode PMTs or avalanche photodiode arrays. In one embodiment of the line-scan imaging device, the inventors also used independently modulated source arrays of 4-22 elements for high-end office printing applications. The inventors demonstrated use of a 22-element array at 635-nm wavelength (single-mode sources, 10-mW per source, 20-μm centers) (Intense Corp., Glasgow) which was set up on an optical test bed for time-encoded imaging; 8- to 10-X de-magnification, single-color detection. This was tested initially on a single flow channel, fixed optics, for 1-D imaging (scanning provided by the fluid flow). As mentioned herein, it is also possible to retrofit (1-D) line scanning onto a commercial single-channel flow cytometer. The inventors also tested 2-D imaging using scanning transverse to flow on a multi-channel PMC device, and then to a line-scan imaging device with expanded optics which include the 5-color cascade detector as shown in FIG. 9.

While the emitter arrays suitable for time-encoded imaging can be purchased of the shelf, the inventor optimized driver circuits for use in the line-scan imaging device. Small-pitch arrays of high power can be purchased off the shelf. At the smallest array spacing there will be cross talk between adjacent elements in the array. Intense LTD specifies ~5% modulation crosstalk between closest elements in their 20-µm-pitch arrays. This much pixel-to-pixel blurring (5% pixel "overlap") would seem acceptable. In order to minimize optical or modulation crosstalk, one can design compensating encoding patterns that minimize emitter-to-emitter modulator crosstalk. In an alternative embodiment, one can tilt the source array relative to the scan direction (the effective source-density doubles if the array axis is 30 degrees rather than 90 degrees to the scan axis. This should reduce next-neighbor crosstalk to 0.0025, which should be entirely acceptable.)

Example 3.3

Modifying commercial Single-Channel Cytometer (FACS) for Line-Scan Imaging:

In one embodiment the inventors "retrofit" installation of line-scan imaging onto commercial single-channel cytometers. As discussed herein, there are numerous advantages for a PMC, (multi-sample throughput, time synchronism, and on-system downstream expression analysis), however, there is a large installed base of commercial single-channel cytometers. With the exception of the CCD-based Amnis system, all systems are presently designed to only allow unresolved fluorescence. Thus, the inventors have designed an imaging detector for a conventional (PMT-based) single-channel instrument by using a reduced (1 µm) spot, small field (100 µm), and fast sensor. The collection optics of conventional cytometers are already of a sufficiently high NA, however current flow uniformity may not be sufficient.

The inventors have designed a highest performance detection module with either a fixed spot, scanner or using a mixed multi-cathode PMT, other fast array detector (e.g., APD array), or emitter array and time/phase multiplexing.

Example 4

In Example 4, the inventors demonstrate the ability of line-scan imaging as a means to partition (i.e. cell sorting) real cell samples according to image phenotype (thus cell sorting based on cell phenotype). The inventors choose two model systems that span a range of typical cytometry problems.

Example 4.1

Demonstration of protein localization assay for non-adherent cells in solution (S.a cerevisiae) and a 30× improvement in sample throughput over current microscopes and imaging flow cytometers.

Figure 12:
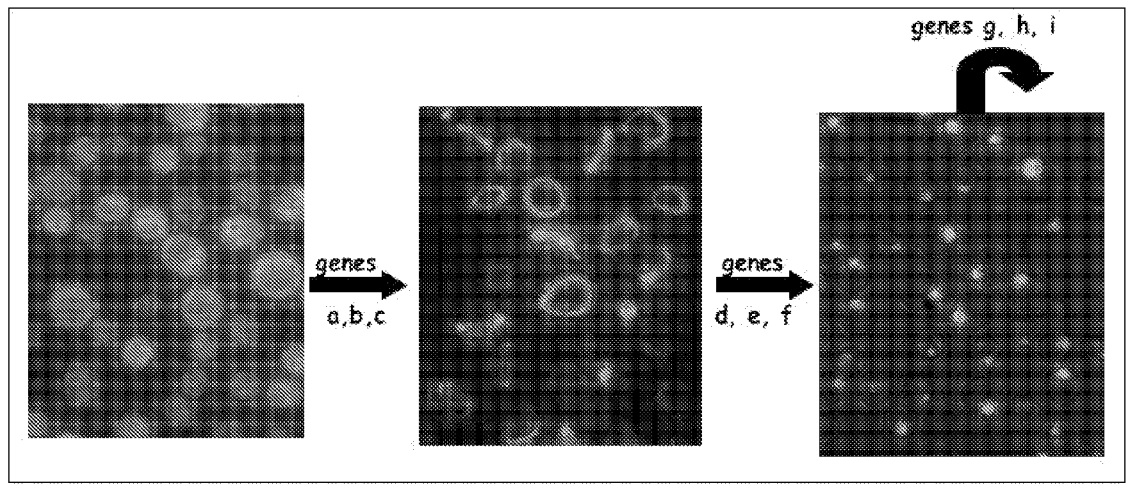
FIG. 12 shows images of the use of the image-line module for a high-content screen in yeast.

Amyloid proteins are fundamental players in neurodegenerative disease, e.g. Parkinson's disease; furthermore, much of the homeostasis of several of these molecules is conserved from the much simpler and easily cultured systems of yeast, such as S cerevisiae. A series of re-arrangements of the amyloid proteins in yeast can be done (Krishnan, R., and S. L. Lindquist. *Nature*. 435:765-72, 2005; Shorter, J. and Lindquist, S. L., *Nature Rev. Genet.*, 2005) (FIG. 12), which is marked by highly distinct condensate patterns (terminating in inheritable prions), and has created inducible reporter-labeled strains that inexpensively produce large, nearly homogeneous, samples of specific phenotypes. The missing element is a good automated method of reading out the protein localization. The inventors can use the line-scan imaging device as disclosed herein for combinatorial biology, drug discovery, and time-course experiments, which could never been achieved manually.

The organism *S. cerevisiae* is typical of non-adherent systems that are infrequently addressed with HCS because, since cells do not settle easily to the bottom of culture dishes, they present an ambiguity in optical focusing. Focusing even, in the best of cases, is usually the longest step in the time budget for HCS using a microscope. Furthermore the organism is a little on the small size for normal HCS, ~3-6 µm diameter. Although relatively few HCS studies use yeast, there are some virtues to these organisms including, relatively easy expansion, and genomic simplicity (6000 genes) in a model with much conserved biological mechanism common to mammalian cells (Krishnan, R., and S. L. Lindquist. *Nature*. 435:765-72, 2005; Shorter, J. and Lindquist, S. L., *Nature Rev. Genet.*, 2005).

Example 4.1.0

Development of a parallel flow HCS assay for amyloid aggregation in *S. cerevisiae*

The positive phenotype shows one or several GFP focal condensates of 0.2 to 1 µm dimensions in a cell of characteristic 5 µm diameter. The induced "negative" shows an even distribution of the GFP marker on the cell wall or in the cytoplasm. The method was first simulated using a geometrical model. The laser focus, a shape of adjustable dimension, was intersected with model phenotypes to generate theoretical Scan Types. The laser scan was stepped vertically by small (1 µm) increments and the cell was rotated through 360° to generate simulation data that represented random two-color scans on the PMT detector. After some exploration, four high-content features were selected: (1) green symmetrical with red (Sym), (2) green assymetrical with red (Asym), (3) red only (RO), and (4) red overlapping green (R=G). The simulation then counted the number of scans that fell into these Scan Types for various settings of the laser dimensions.

Several aspects became immediately apparent. First, even for the small (5.5 µm) diameter cell that represented *S. cerevisiae*, it was possible to efficiently distinguish the model positive and negative phenotypes with a relatively large laser focal diameter of 3-4 µm. In fact, somewhat surprisingly, the efficiency of the PMC detector in generation the most diagnostic Scan TYpes (Asym, and RO) actually increased as the diameter of a laser spot is increased from 1 µm to 4 µm. This is because the larger laser spot senses a larger fraction of the cells in the sample. The spatial information from a 3- to 4-µm laser spot is still sufficient to obtain the high-content information needed to distinguish the feature (assymetry). The feature Asym, which is uniquely ascribed to the positive genotype is generated with a relatively high absolute efficiency (31% of all possible scans through a positive sample at 50% seeding density in the flow channel, 4 µm laser spot). The generation of the Asym Scan Type increases further, as would be expected if the laser spot is elongated in the direction perpendicular to the scan.

While these simulation results were an encouraging prediction of an efficient HCS with 1-D images, the geometrical model applied arbitrary thresholding of the Scan Type boundaries and might not adequately represent the noise of a real sample set. To test the method further, the inventors then acquired a set of real 2-D images of S. cerevisiae αSyn/GFP samples on a Cellomics ArrayScan HCS system. Cells identied as positives in the full 2-D image were isolated as a data set, then reprocessed into randomly located 1-D line scans.

This approach reproduced realistic noise on a large array of positive and negative phenotypes. As expected, the more realistic simulation reduced the bin counts in the Scan Types that were previously useful for identifying positives—typically by a factor of ~2 relative the idealized geometrical model. There was also a shift toward higher relative efficacy in production of the most diagnostic Scan Types for the smaller 1-2 μm laser spot sizes. However, the 3-4 μm optical resolution remained effective in separating the positives from the negatives. Using the extracted Cellomics data, the model predicted that 18% of the total PMC detector scans would uniquely identify positives even with a 3-4 μm optical resolution, round spot and 50% column seeding. An 8×1 μm spot increased this number to 27%.

Based on this simulation, an optical scanner was developed and set to an effective optical resoluation of 4.3 μm (Gaussian width, circular spot). S. cerevisiae αSynuclean/GFP (αSyn/GFP) mutants were injected into the PMC and were drawn at a rate of 20 μL/hr/lane past the scanning detector, at a digitizing interval of 1 μm per data point, 3 scans/s.

Data reduction from 1-D images In the first step of data reduction, cell events were extracted, replicated into (i) raw, (ii) three-point-smoothed, and (iii) Gaussian-fit line-scans, then processed as a two-color pair. A total of 82 feature calculations (e.g., max signal strength, max signal position, FWHM, center, total signal area and perimeter, green-signal-area/red-signal-area, green-FWHM/red-FWHM, etc.) were made on each cell event using the raw, smoothed, and fitted signals from isolated and combined color channels. Data sets of 500 cell events using negative (un-induced) and positive (condensate-induced) samples were compared. As a fairly rigorous test, the experiments used relatively weakly induced positives.

Two modified versions of multiparameter phenotypic profiling were applied to analyze this feature data according to (a) identified single-cell profiles and (b) group statistical profiles.

For the single cell profiling, the same algorithms used in optical modeling (Asym, Sym, R=G, RO) were used to classify cell signatures by scan type. For group statistical analysis, the inventors first identified and removed cell events with insufficient green signal (i.e., red only scans). This reduced the dataset from the original 500 objects. The inventors then equalized the data sets to the number of objects in control or sample data set, whichever was smaller (380 to 420 events). The inventors evaluated the 82 feature values in negative-to-negative and negative-to-positive samples using the Kolmogorv-Smirnov test (K-S test). Using Matlab and the k-means function ktest2, the inventors created a program that looked at one test sample and one control sample and calculated the K-S value and p-value for each of the 82 features. 7 symmetry-related features were identified from this broader set: three that should remain constant for all (positive and negative) samples and four that should vary between positive and negative samples:

Control features (should be similar in positives and negatives): (i) F60 red total intensity ratio around the maximum signal point, (ii) F64 red intensity perimeter around the maximum signal point, and (iii) F65 red intensity perimeter around the calculated object center. The differentiating features: (i) F63 green intensity area around calculated red object center, (ii) F67 ratio of green perimeter before and after the calculated red object center, (iii) F71 ratio of F67/F65, and (iv) F81 green P2A/red P2A (P2a=perimeter$^2$/2*pi*area).

The inventors created a K-S heat map of the selected features for each sample. The inventors generated the central distribution function used by the K-S means test for the reference and test sample and then calculated the difference over F(x) by subtracting the two cumulative distribution functions (CDF's) for each sample (absolute values for easier visualization).

The group-statistical results for the same three unique positive and three unique negative samples was performed. The heat map indicates similarity among the various negatives and various positives, and difference between negatives and positives. The test was further reduced to test the F67 (indicating positive) and F65 (control) features only.

Example 4.1.1

Figure 7:
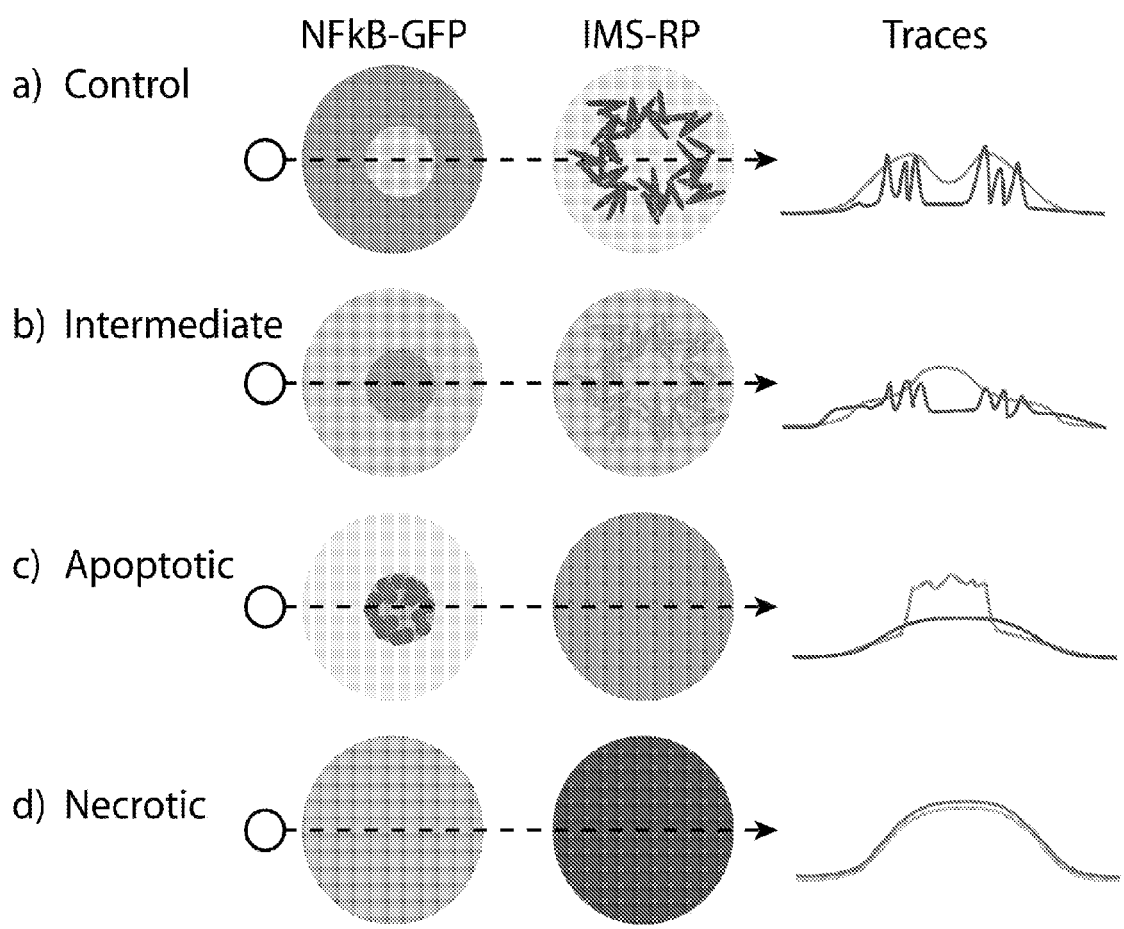
FIG. 7 is a schematic image showing the predicted distributions of fluorescent signals from the localization reporters and distinguishable line-scan traces (right).

Optimize cascade detector for S cerevisiae/Sup35-GFP phenotypes: The inventors optimized the line-scan imaging device with straightforward adjustment of fluorescence partition in the detector followed by training of the software filters to identify yeast with Sup35-GFP expression. For a feasibility study the inventors began by modifying one of the prototype PMC systems to reduce the spot size of the scanner to the extent possible (from 30-μm to 3.5-μm). The signal processing hardware was programmed to collect 100 points at 1-μm spacing across the channel (FIG. 3). However, the current hardware had the limitation of processing pixels at a maximum 8,000 per second. To get around this restraint the range of the scanner was limited to 320 data points at 1-μm resolution and 20 Hz. The inventors utilized S. cerevisiae mutants engineered by the Lindquist Lab (Whitehead Institute, (Goedecke N, et al., Electrophoresis 25(10-11):1678-1686 (2004); Callewaert N, Electrophoresis) to overexpress the amyloid protein αSyn-GFP. Under induction, the protein condenses from a uniform distribution in cytoplasm to one or several focal conjugates per cell of 1-2 μm dia. (FIG. 6). Cells were fixed and fluorescently labeled with a red whole cell dye. A post-scan algorithm used various comparative color-channel algorithms to categorize images and identify cell meta-data (FIG. 7). Data were filtered to select a target diameter (red FWHM) of 4-6 μm, then an algorithm modelled after (two-dimensional) "roundness" was applied to the red and green channels. This separated the positive and negative pools. Alternatively, when analysed with a small-width threshold (red FWHM 2 μm after deconvolution of the laser spot), line-scans often skirt the αSyn-GFP focal conjugates entirely. These events are highly distinguishing between positives and negatives.

Protein-localization HCS assays (such as nuclear and membrane translocation) are extraordinarily powerful assays, but no current instrument has sufficient cost and throughput metrics. The existing instruments are automated microscopes and CCD based single-channel cytometers (Cellomics, Accumen, Amnis) with throughputs of no more than one 384-well plate per hour. The inventors demonstrate high-content screening (HCS) in parallel flow at a rate approaching 10× the throughput of existing instruments. The target applications are those current impractical in environmental health, genome-wide research and drug discovery, where HCS is generally too slow on a microscope or CCD-based cytometry system. As a focus, the inventors use the parallel flow line-scan imaging device as disclosed herein to monitor the redistribution of the NFkB-GFP and IMS-RFP reporters, stably expressed in HeLa cells, when exposed to combinations of extrinsic factors.

Protein interaction maps provide network topology but the outcome, in terms of cell fate, of different combinations of inputs into the system remains to be fully elucidated. A major reason for slow progress is the gap in assay performance that exists between low-sample-throughput FACS, high-throughput low-content plate readers, and high-content low-throughput 2D imaging-based assays. Cell-level measurement is required because cells have different resting levels of reactants, which cause them to respond to inputs asynchronously or in some cases not respond at all. Thus, population-level measurements often mask the timing of events that can be measured at the cell-level using HCS. However, HCS requires sophisticated algorithms and expensive infrastructure to cope with the large volume (multi-terabytes) of raw images and rich meta-data. Though critical for downstream follow-up assays, traditional HCS is out-performed by high throughput screening (HTS; population-level non-imaging platforms) in terms of sample throughput per dollar per day. The inventors demonstrate herein the line-scan imaging PMC approach provides higher content than conventional HTS with higher throughput that imaging-based HCA but without a concomitant increase in data volume. This combination of attributes enables the design of large-scale multiplexed cell-level screens at relatively low cost.

The NFkB transcription factor recruitment from the cytoplasm to the nucleus is a well-established indicator of a cell's response to stress. Intrinsic factors such as UV-induced DNA damage and oxidative protein damage as well as extrinsic factors such as TNFα-TRAIL and IL-1 lead to ubiquination of IkBa, which subsequently unbinds NFkB allowing it to relocate to the nucleus and promote transcription. Proteosome inhibitors such as the E3-ligase inhibitor RO106-9920 (Boufounos P, et al., *Journal of the Franklin Institute* 341(1-2):23-36 (2004)) A small molecule ubiquitination inhibitor blocks NFkB-dependent cytokine expression in cells and prevents import of NFkB by inhibiting ubiquination and degradation of IkB☐. In fact, hundreds of NFkB inhibitors have been reported but the signaling pathway itself remains poorly understood in different tissues and disease states.

Recently, a monomeric RFP-based live-cell indicator comprising the first 147 by of Smac-1 (IMS-RP) has been used to measure the differences in the response to cells in a population given an extrinsic death ligand such as TRAIL. This indicator provides a measurement of mitochondrial outer membrane permeability (MOMP), which signals escape of Smac and cytochrome c into the cytoplasm. Once cytoplasmic, Smac removes inhibition of caspases 3 and 7 by XIAP leading to activation of effector caspases and cell death.

Example 4.1.1.2

Demonstrate a dual color GFP/RFP relocalization assay for non-adherent cells in suspension and a 30×improvement in sample throughput over current microscopes and single-channel imaging flow cytometers.

The inventors used HeLa (transiently transfected) and CHO cells stably expressing the NFkB-GFP reporter (commercially available from ThermoScientific). This step enabled the inventors to fine tune sample preparation, experimental procedures and data analysis.

Localization reporters are well-established tools for HCS but, due to their requirement for spatial resolution, are not suited to whole-well HTS platforms Unlike transcriptional reporter systems, the localization reporter shuttles between the cytoplasm and nucleus (NFkB-GFP) or between the mitochondria and cytoplasm (IMS-RP) given the appropriate input signals, such as 50 ng/ml TRAIL for approximately 1 hour. TRAIL and other ligands are administered in the presence of cyclohexamide halting protein synthesis, which might otherwise affect survival pathways, increasing the time until death.

Example 4.3

Conduct a trial assay uUsing NFkB-GFP and IMS-RP to determine timing and dose response of TRAIL, IL-1 Treated HeLa S3 cultures to rescue with RO106-9920: The inventors conducted a pilot project with cells treated either with or without cyclohexamide, exposed to a range of TRAIL and/or IL-1 concentrations and subsequently rescued after varying times with RO106-9920. The distribution of GFP and RFP signal will be measured in living cells during the course of each experiment and data will be discretized into appropriate cell states ('healthy', 'intermediate', 'apoptotic', 'necrotic', as shown in FIG. 7) per unit time (e.g. 10 minute bins). This set of experiments provided the inventors with a sufficiently challenging number of conditions to develop scalable image analysis algorithms, test assay robustness, and prepare for a scale-up to combinatorial studies using drug libraries, RNAi and panels of cell lines with different reporters (data not shown).

Example 4.1.2

Readout a time-course induction series using live- and fixed-cell samples: Time course readout in live cells is not practical with a HCS microscope. The inventors demonstrate line-scan imaging to read out the Sup35 assay using both fixed and live cells, then ultimately read out time-course response curves.

Example 4.1.3

Cell Lines to be Used. True and Lindquist (2000) have identified 7 yeast strains that will sustain Sup35/Rnql prions and alpha-synuclein amyloids. These include 74-D694, Mat a, adel-14, trp1-289, his3-Δ200, ura3-52, leu2-3, 112 and other strains (Krishnan, R., and S. L. Lindquist. *Nature*. 435: 765-72, 2005; Shorter, J. and Lindquist, S. L., *Nature Rev. Genet.*, 2005), all of which are maintained in the Lindquist Laboratory and many of which were used by the inventors to optimize parameters and modules of the line-scan imaging device as disclosed herein.

Example 4.1.4

Methods of Induction in Yeast. The inventors use transient over-expression of the Sup35-protein, its prion region (NM) alone or the prion region (NM) fused to YLP and GFP reporters to induce [PSI$^+$] induction into yeast. All three methods are thoroughly confirmed (Krishnan, R., and S. L. Lindquist. *Nature*. 435:765-72, 2005; Shorter, J. and Lindquist, S. L., *Nature Rev. Genet.*, 2005).

Example 4.1.5

Validation Testing The eight (NIH CGC) acceptance tests for assay validity listed in Sec. D2.10 were repeated with the assay samples. Measurement of reproducibility of potency will be tested with duplicate 384-well runs using the additional NIH CGC criteria (NIH CGC web site for definitions):

The inventors compute the difference in log-potency (=first–second) between the first and second run for each compound. (This criteria employs ratios of $EC_{50}$ values (relative potencies)). The inventors computed the Mean-Ratio: This is the geometric average fold difference in potency between two runs. The inventors computed the Ratio Limits: This is the 95% confidence interval for the Mean-Ratio. Ratio limits should include the value 1. The inventors computed the Minimum Significant Ratio (MSR): This is the smallest potency ratio between two compounds that is statistically significant. Pass criterion is MSR<3. The inventors computed the Limits of Agreement: Most of the compound potency ratios (approximately 95%) should fall within these limits. For each compound compute the Ratio (=first/second) of the two potencies, and the Geometric Mean potency.

Yeast represents an aggressive system in terms of optical resolution requirements. Furthermore cultures in deep-well plates are more heterogeneous (exhibited in variable cell staining) than well-stirred bulk cultures. Therefore the real heterogeneous samples represent increased demands on statistical analysis. In live cultures, the problem is exacerbated since cultures will be varying on an hourly time scale and, at high levels of Sup35/α-synuclein expression, cells are programmed toward fatality within 12 hours. However culture conditions can be modified to assist the speed of the PMC readout and automated stirring of the cultures if necessary using an on-system 96-tip pipettor. The inventors demonstrate the ability to control culture temperature. Fixed samples should not be an issue.

Example 4.3.2

Development of a line-scan imaging assay based on nuclear translocation for non-adherent cells (and adherent cells in flow) and show a 10-fold improvement in sample throughput relative to automated microscopes and CCD-based cytometers: The relocation of transcription factors from the cytoplasm to the nucleus (NT) is a nexus in many signaling cascades including the host defense response and cell differentiation. For example, the translocation of the factor NF-κB can be induced by antigen-specific or mitogen-specific stimulation and directly results in increased expression of the pro-inflammatory cytokines TNF-α and IL-α1 Because of this place in the immune response, assays based on NF-κB translocation are among the most frequently scaled HCS assays within the pharmaceutical industry. There are well-established protocols, commercial reagent kits, and many published studies of NF-κB NT, therefore this system is an excellent choice to prove the capability of line-scan imaging for increased throughput. A 10-fold or more improvement in throughput would immediately translate into a 10-fold increase in productivity for ongoing combinatorial drug screens. There would be an immediate pull to commercialize.

Figure 13A:
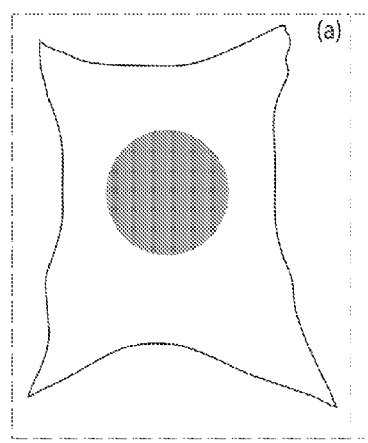
FIG. 13A-13B is a schematic image showing use of the nuclear translocation assay to characterize the ratio of a translocating marker from the cytoplasm to the nucleus.
Figure 13B:
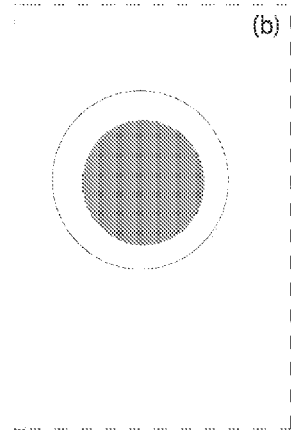

Although NT is normally restricted to adherent cells and microscope readout, this assay has been demonstrated in flow (2-D) imaging (George, T. C., et al., *J Immuno. Methods* 311, 117-129, 2006). The assay is more difficult for non-adherent cells because of the smaller cytoplasm-to-nucleus (ratio) area-projection of cells in solution (FIG. 13), however, most immune system cells are natively non-adherent, so that reduction of this method to microscope readout (adherent cells) has unknown (negative) implications. Furthermore the relatively poor background rejection of wide-field (CCD) imagers confounds the problem of flow imaging. Amnis addresses focus ambiguity by actually increasing the depth of focus (to make all images more uniform, though probably fuzzier) [27]. Line-scan imaging takes the opposite approach of sectioning a narrow depth-of-focus slice through the cell (and missing cells that are not well-centered in the center of the hydrodynamically flow). Thus, the inventors have developed a line-scan imaging system which exploits the fact that nuclear translocation assays such as NF-κB are often statistically significant with as few as 50 filtered images.

Example 4.2.1

Data reduction and Statistical Analysis for Nuclear Translocation Assay: The most straightforward starting point for reduction of NT data is linear regression analysis to extract the Pearson correlation coefficients of the stimulated and un-stimulated translocation images. The inventors used this in analysis or color channels that have been corrected for cross talk. The inventors also constructed a modified similarity-scoring algorithm suggested by George (George, T. C., et al *J Immuno. Methods* 311, 117-129, 2006) and optimized this for the 1-D NT assay. In order to understand statistical significance in samples with small differences, it is common to use refinements of the T-test such as the Mann-Whitney U rank sum test.

$$\rho = \frac{\sum_i (x_i - X)(y_i - Y)}{\sqrt{\sum_i (x_i - X)^2 \sum_j (y_j - Y)^2}}$$

Example 4.2.2

Figure 30:
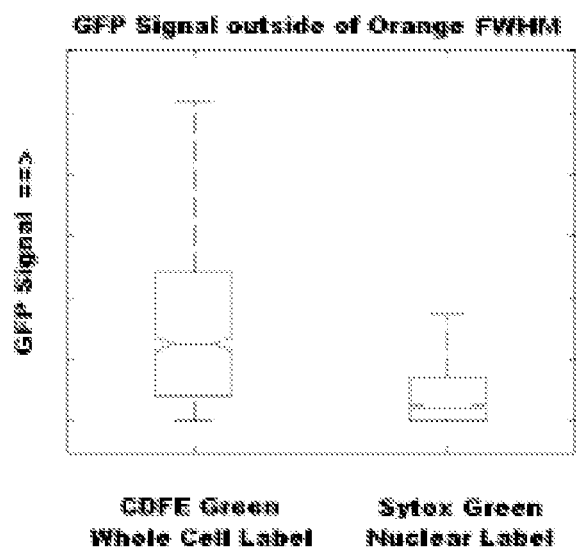
FIG. 30 shows box plots of the two samples that simulate nuclear translocation. The green signal outside the nuclear area (nuclear area defined by the orange PMT channel) is plotted on the vertical axis.
Figure 31:
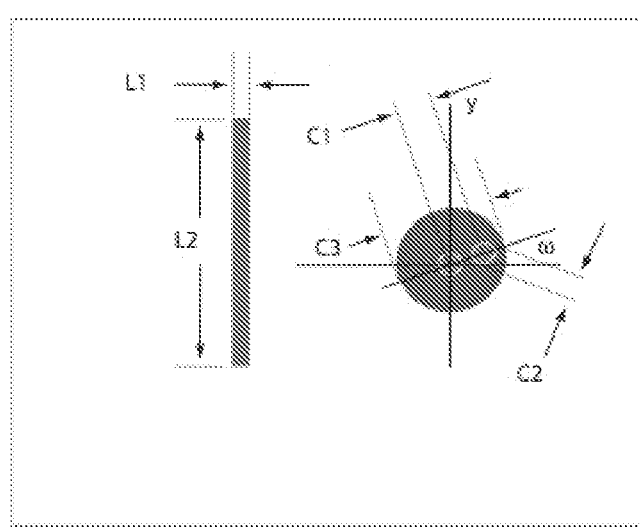
FIG. 31 shows a simulation model used to determine laser spot parameters for PMC detector. The laser spot is represented as an ellipse of dimensions L1 and L2. An S. cerevisiae cell (red, diameter C3) with two green fluorescent protein (a-Syn/GFP) condensates, (green, diameter C2, separation C1), is intersected with this laser spot to generate theoretical 2-color 1-D images similar to those shown in FIG. 1. The model increments the laser scan vertically (y) and rotates the cell for all possible angles. This model is then run with different choices of the laser spot dimensions L1 and L2, and the resultant data file of 1-D images is processed with various algorithms to determine most efficient values of L1/L2 for classification of S. cerevisiae phenotypes.
Figure 32A:
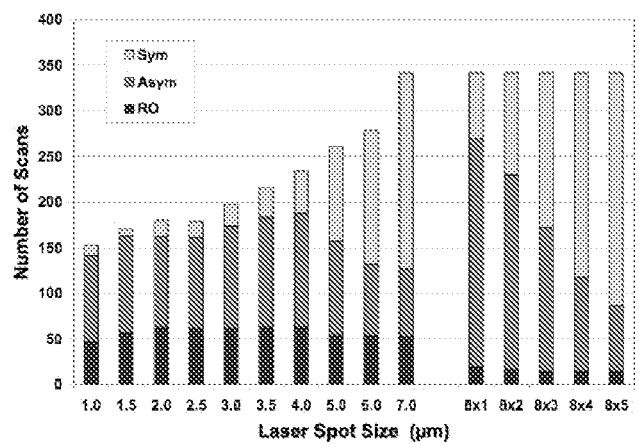
FIGS. 32A-32B show exemplary 1-D imaging simulation results.
Figure 32B:
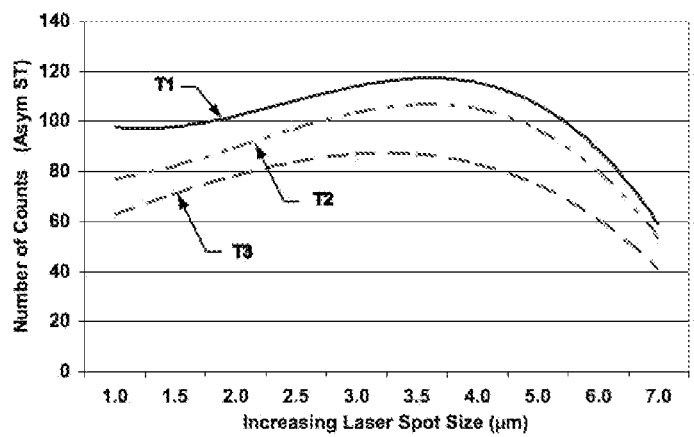
Figure 33:
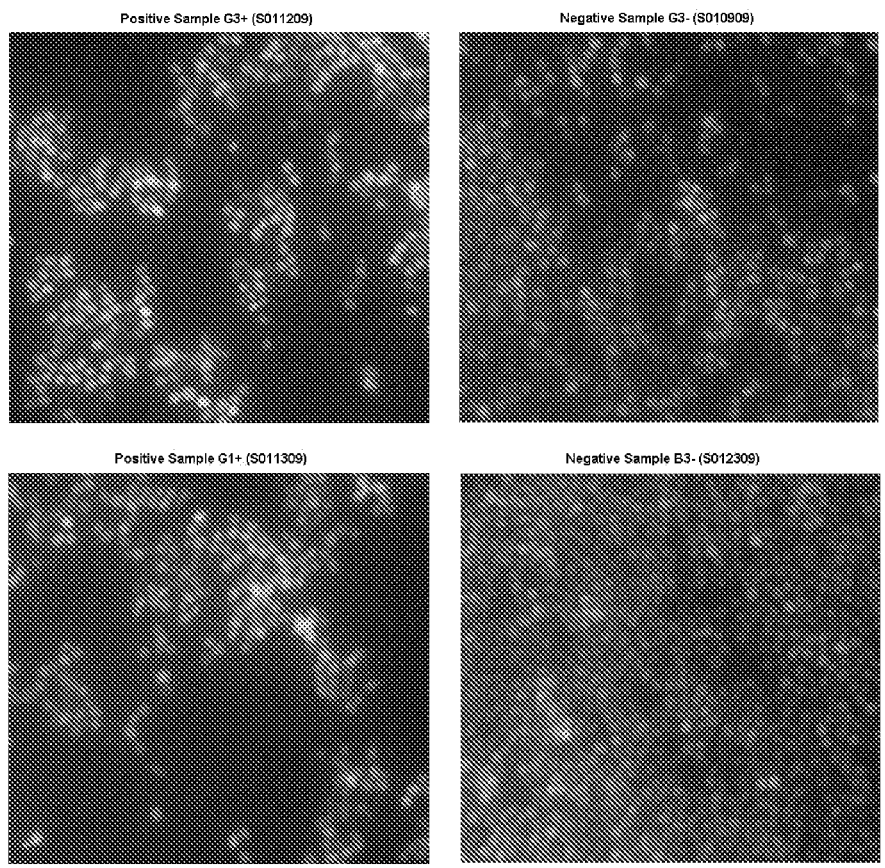
FIG. 33 shows two modified versions of multiparameter phenotypic profiling were applied to analyze this feature data according to (a) identified single-cell profiles and (b) group statistical profiles.
Figure 34:
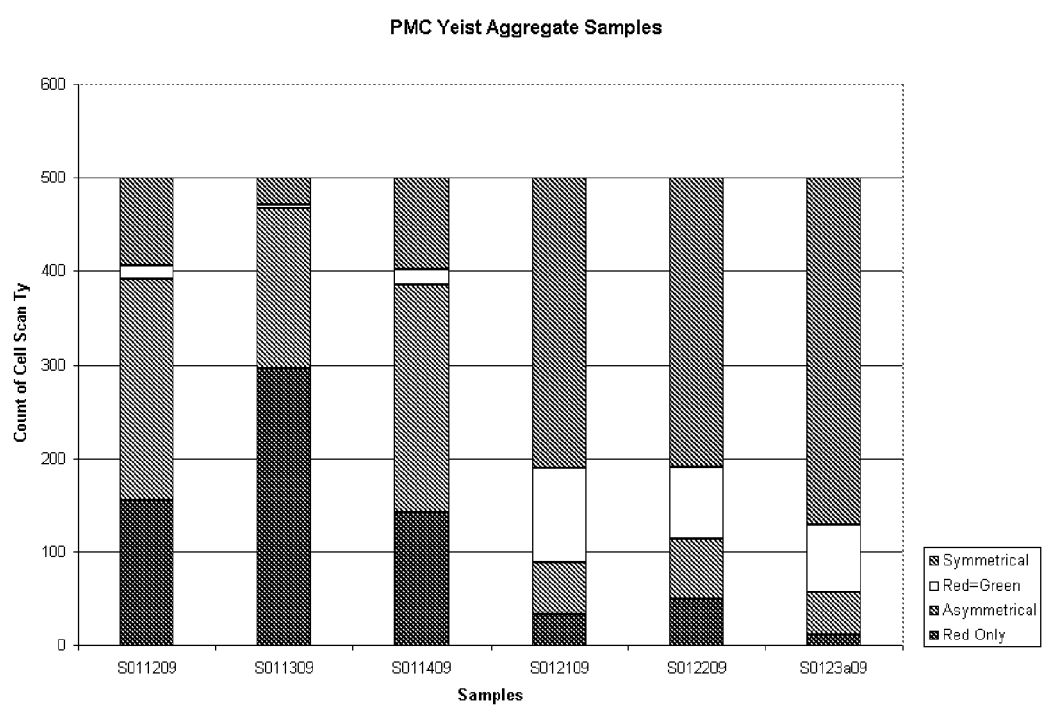
FIG. 34 shows results of three positive (left) and three negative (right) samples that have been processed by a single-cell typing algorithm. The positive samples show higher percentages of red only scans and asymmetrical scans. Each data set of 500 cell events (six unique samples) is classified according to the total count of single-cell events that are binned into four scan types. The three left-side (positive) samples contain many more scans classified as "Red Only" or "Asymmetrical" while the three right-side (negative) contain many more scans classified as "Red=Green" or "Symmetrical". This is consistent with the inventor's model that predicts that positive samples that have GFP green dye aggregated into part of the cell will scan as red only, or show the green dye as not centered throughout the cell.
Figure 35:
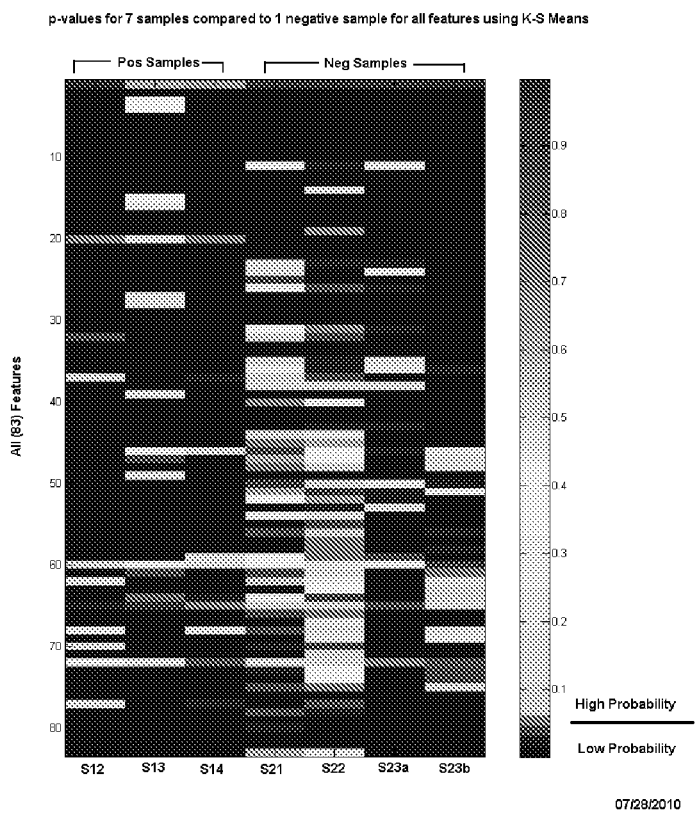
FIG. 35 shows that for three positive and four negative samples, all 84 features are compared against a negative control sample (S09) using a K-S means test. The p-value results for the seven x 84 tests are displayed as a heat map with blue designating low probability and red designating high probability. Note that some features (based on red channel) should have high probability for all samples and some features (based on green channel) should have high probability for negative samples and low probability for positive samples. Note that features above 60 are based on multi-feature/color calculations that often negate signal strength variance and are therefore more robust.

Nuclear Translocation Assay:

Proof of principle The inventors used mouse fibroblast cells (swiss-3T3) that were treated with Trypsin EDTA (Cellecgro) to make them non-adherent, and then fixed (3.7% formaldehyde) and labeled these cells with Sytox Orange nuclear stain (2.5 mM, Invitrogen). Half of this sample was dyed with a second nuclear stain, (0.5 mM Sytox Green, Invitrogen) and the other half with CDFE whole cell stain (5 mM, Invitrogen). Three singly stained, control, samples were also scanned in order to obtain PMT color correction information. As above, the cells were scanned with a first-generation PMC with a laser spot size of ~3.5 micron and an image digital capture resolution of 1-μm per time point under the lane. A post-scan algorithm identified the cells, smoothed, digitally zoomed the images, then color corrected and normalized the fluorescence levels. Two methods were used to separate the samples. The first was by comparing the object width (FWHM) of the orange and green channels (FIG. 28). A more accurate method appears to be to use the orange channel as a mask of the nucleus, and quantifying the green signal outside that mask (FIGS. 29, 30). Therefore even with 3.5-μm spot resolution, 1-D line scans can resolve nuclear vs. cytoplasmic location of the green marker. A next-generation optical scanner with 1-μm resolution (rather than 3.5-μm) and updated digitizing electronics, will greatly increase the number of color channels, allow 1-D and 2-D line scanning, and enable data collection at increased speed.

NF-κB nuclear translocation assay The inventors next developed a line-scan imaging version of the NF-κB nuclear translocation assay and apply it to mammalian cells. The standard protocol often uses a combination of Hoechst and Texas Red labeling. The NF-κB p65 subunit is sensitive to several known stimulants, for example, altered interleukin ILa1 or tumor necrosis factor (TNFα). The translocation to the nucleus is required to induce gene expression.

Example 4.2.3

Specific Verification Experiments: The inventors also demonstrate algorithm development. The spatial resolution of the optical scanners can also be adjusted through the system telescopes. The first significant test of the NT methods will be a collaboration on hematopoietic stem (rare, and non-adherent) cells as well as on 3T3 cultures (see Example 2).

Example 4.2.4

Cell Lines: The inventors also maintained two cell lines for use as standards [both of (a) IC-21 (Type—Mouse peritoneal macrophage; SV40 transformed) ATCC® Number: TIB-186 (available on the world wide web at atcc.org), and (b) 3T3 (Type—Mouse embryonic fibroblast) ATCC® Number: CCL-163.2 (available on the world wide web at atcc.org)] using equipment and protocols already in use in the larger lab.

Example 4.2.5

Assay Protocols for NF-kB: Cells were be prepared using available kits (NF-kB Activation HCS Reagent Kit, Cellomics Inc., catalog #K01-0000-1, available on the world wide web at cellomics.com), which contain fluorescent reagents and protocols for optimized sample, purification, or filtration steps. After fixation, the plates are stable for extended periods when stored at 4° C. The NF-kB is normally present in the cytoplasm and can be stimulated to transfer to the nucleus by various known inducers, including ILa1. The NF-κB assay using line-scan imaging device as disclosed herein was validated using a fluorescent microscope in parallel with the commercial NF-κB assay detection. (data no shown)

Example 4.2.6

Apply NT Assay to hematopoietic stem cells (<100 Cells Per Culture): The unsolved assay problem with non-adherent and rare cells neatly fits the strengths of microfluidic cytometry. A near homogenous hematopoietic stem cell (HSC) population of mouse bone marrow Lin (−) CD150 (+) CD48 (−) CD41 (−) cells, will be isolated by flow cytometry (FACS). At most 100 (ideally fewer) cells were plated into each well of a 384 well plate, and each will be infected by a type of RNAi retrovirus. These cells were cultured conventionally in our optimized medium for 3-7 days in 384-well plates (data no shown). Antibody cocktails, for example, of anti-CD3-FITC, anti-B220-PE, anti-Mac1/Grl-PE/CY5.5, and anti-Ter119-PE/CY7 were added to stain these cells in each well for the purpose of detection of HSC differentiation into major lymphoid and myeloid lineages (data no shown). Alternatively, antibody cocktail of anti-Lineage-PE, Sca-1-F1TC, IGF2-hFC followed by anti-hFc-PE/CY5.5, and anti-CD62L-PE (based on our preliminary data showing the phenotype of cultured HSCs) was used for the purpose of detecting HSC proliferation. The cells were then applied to the line-scan imager to detect fluorescence (data no shown). The RNAi candidates that significantly affect HSC differentiation or proliferation can then be identified based on the results (data no shown).

The major advantages of the line-scan imager are: (1) The inventors can only obtain very limited numbers of HSCs from mice; here ~100 cells will be in each well, which are not enough for analysis by conventional flow cytometry. Note that operating parameters for our PMC (Table 2) are consistent with 1-µL volumes and cell counts <100 cells. (2) The machine can detect multiple fluorescent markers in imaging mode, which is critical for characterizing the status of HSC differentiation or proliferation.

Example 4.2.7

Cell Culture/Marker Method: The extraction/infection/culture of the stem cells and antibody staining was performed by established methods known by one of ordinary skill in the art. Cells in 20-µL suspensions were scanned in parallel on the 32-channel chip to get fluorescence ratios (data no shown). The inventors indicate the line-scan imaging device can be used to expand the study to measure MAP kinase and NF-kB localization in the imaging mode (data no shown), which is a practical way to greatly scale a limited study published by Pouton and (Pouton, C. W. and Haynesem J. M., Nature Reviews, 6, 605-617, 2007).

Example 4.2.8

Outcome of tests on Hematopoietic cells: The inventors adjusted the sensor and algorithm parameters for hematopoietic stem cells (mouse), then conducted a test using a small panel 100 test RNAi's (data no shown).

Example 4.3

Trial assay using 10 Modifier genes and monitoring Sup35-GFP: The Lindquist Laboratory has identified a set of modifier genes that are of interest for combinatorial studies of amyloid homeostasis. The inventors conducted a training set using 10 genes from this set as a trial system for of the new assay. The inventors developed the image analysis algorithms, test the robustness, and prepare for a scale-up to combinatorial studies.

Assay reproducibility will be determined by measuring the overlay accuracy of time-coarse plots, and by calculating the coefficient of variation between IC50 dose points from multiples out of a 384-well plate. The last metric that is needed is the sampling number that is required for statistical significance. This is estimated by two-way analysis of variance with stimulated and un-stimulated cell samples. Full validation will consist modified forms of a "3-day Plate Uniformity study" and a "Replicate-Experiment study" (http://www.ncgc.nih.gov/guidance). The standard "Interleaved-Signal" plate study will be customized by superimposing an Interleaved-Channel Study (to test across the multilane microfluidic) with the pass criteria published at the NIH Chemical Genomics Center web site ("ncgc.nih.gov").

4.3.1 Cell Lines to be Used: True and Lindquist (2000) have identified 7 yeast strains that will sustain Sup35/Rnql prions and alpha-synuclein amyloids. These include 74-D694, Mat a, adel-14, trp1-289, his3-Δ200, ura3-52, leu2-3, 112 and other strains. The inventors will use transient over-expression of the Sup35-protein, its prion region (NM) alone or the prion region (NM) fused to YLP and GFP reporters to induce [PSI$^+$] induction into yeast.

Example 5

High content Analysis Screen modules:

Example 5.1

FACs Module or Parallel microfluidic cytometer (PMC) module: PMC Rare Cell Assay: expression-cloning screen for the carboxy-terminal parathyroid hormone receptor (CPTHR)

Figure 2A:
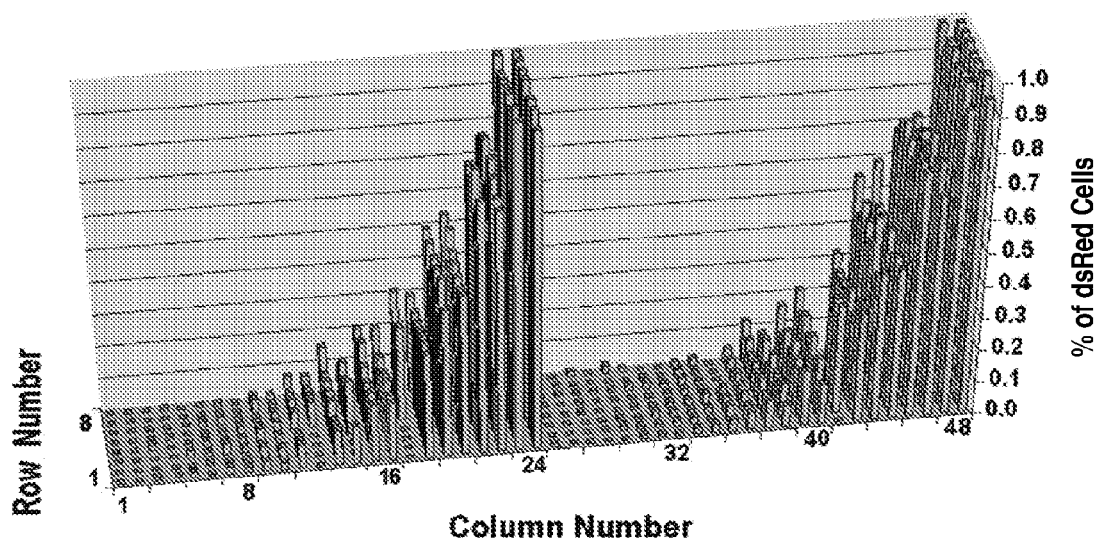
FIGS. 2A-2B show examples of results for a 384-channel run.
Figure 2B:
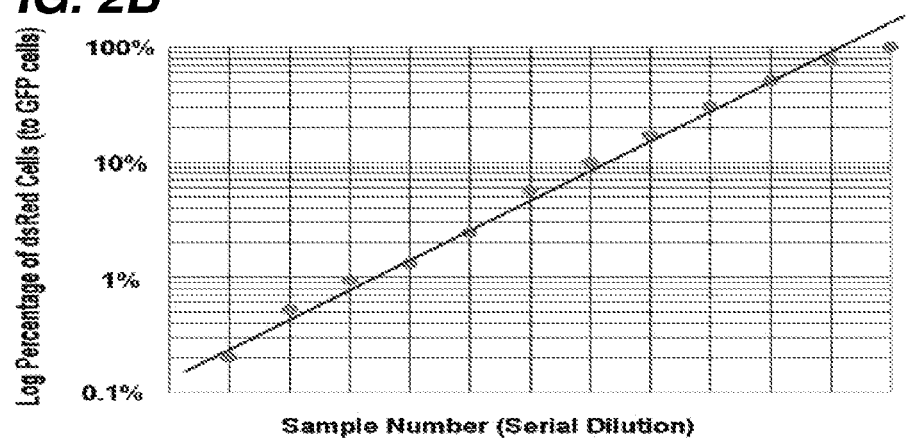

In Mckenna B K, et al., (*Lab on a Chip* 9, 305-310, 2009; herein incorporated by reference in its entirety), the inventors previously demonstrated a 384-channel parallel microfluidic cytometer (PMC) (FIGS. 1 and 2). The multichannel architecture allows 384 unique samples for a cell-based screen to be read out in approximately 6-10 minutes, about 30-times the speed of a conventional fluorescence-activated cytometer (FACS) system. This architecture also allows the signal integration time to be varied over a larger range than is practical in single-channel FACS and is suitable for detection of rare cells in a high background of negatives. The signal-to-noise advantages have been confirmed by using the system to count rare clonal osteocytes in the most difficult early stages of an expression-cloning screen for the carboxy-terminal parathyroid hormone receptor (CPTHR) (Mckenna B K, et al., *Lab on a Chip* 9, 305-310, 2009; Selim A, et al., *Bone Miner Res* 20 (suppl 1):S183 (2005)). This problem requires finding several dozen positive cells in a background of one million negatives. The system is automated around a scanning laser confocal detector and a 96-tip robotic pipettor and can maintain in vitro cultures on-system in 384-well plates. It is therefore directly practical for biology applications using existing high-throughput culture facilities.

Clonal osteocytic cells, expressing a high level of CPTHRs, were derived from fetuses in which most exons encoding the PTH1R had been ablated by gene targeting. A cDNA library was constructed using both random and oligo dT primers to synthesize the first-strand DNA. The cDNA library, average insert size 2 kb, was divided into 100 pools of 10,000 PFUs/each and single pools were transiently transfected into COS-7. It was calculated that a 200-µL sample (1,000 cells/µL) would produce 20-40 positive events in a positive pool. To reduce the false-positive count the inventors used a simplified labeling protocol and evaluated the results using the image-processing algorithm above. Osteocyte cells without fluorescently labeled ligand were used as a negative control.

The initial screen included nine sample pools and one control, all of which were run in redundant microfluidic channels. All samples showed a few positive cells with a median count of 4 cells and a standard deviation of 12.58. The inventors calculated the boundary for outliers, median plus two sigma, to be 28 cells. One pool was an outlier with 39 positives, and when tested again produced 35 positives. The outlier was subdivided into twenty sub-pools and each was tested twice. A count of positives produced a median of 5.5 cells, a sample deviation of 12.47 and an outlier boundary of 47. One sub-pool showed 95 and 98 positive cells. This process was repeated for two more subdivisions until a sample was produced that was overwhelmingly positive (>10,000 cells on the PMC). Finally, the inventors isolated a candidate cDNA, which was sequenced by capillary electrophoresis and found to include a seven-transmembrane domain belonging to a family of g-protein coupled receptors.

Example 5.2

Multiplex Qpcr module. Multiplexed High-Content Expression analysis from less than 10 transcripts: Demonstration neutrophil engulfment of fungi: The gold standard for quantitative analysis of nucleic acids is real-time quantitative PCR (qPCR), which is implemented as monoplex or low-order (2-4 multiplex) reactions using multi-well (96- to 384-well) fluorometer readout. A principle limitation is that this method becomes excessive in reagent cost and sample requirement when scaled to multi-gene analysis. The inventors have previously demonstrated (see e.g., Ueberfeld, J. and Ehrlich, D. J. *Electrophoresis*, (in Press 2009). Ueberfeld J, et al., (in press, Humana Press 2009), which are each incorporated herein by reference in their entirety) an approach that is reads out parallel microfluidics and which extends a much higher degree of multiplexing to qPCR, ultimately 20-50 genes per reaction, while maintaining the high-dynamic range and sensitivity that is the signature of the method.

The novel "whole-multiplex" standard curve method was termed "Reaction Mapping". The inventors demonstrated accurate quantitative expression measurements with a few as 10 transcripts over a dynamic range of six orders of magnitude using a high-dynamic range detector. The method becomes very efficient when scaled to an expression study with many unique samples (Ueberfeld J, et al., (in press, Humana Press 2009)). Importantly, it can be integrated onto the same automation and detection system that is used in the FACs module, such as a PMC module as disclosed herein for flow cytometry.

To demonstrate this, the inventors constructed a panel of 12 primer pairs to investigate gene expression changes during neutrophil engulfment of fungi. Neutrophils were cultured with *Candida albicans* that was preopsonized with human serum. Total RNA was extracted, reverse transcribed and used as a template in the 12 plex PCR. Total RNA of neutrophils cultured alone served as a control sample. Total RNA was prepared following the TR1 reagent protocol. cDNA was created using the Retroscript kit (Ambion, Austin, Tex.) on a Perkin Elmer GeneAmp PCR System 9600 following the manufacturer protocol. 300 ng total RNA served as template for the reverse transcription, random decamers were used as primers. Primer design for the multiplex PCR was guided by the goals of spreading amplicons across the optimum 100- to 400-bp region using the three fluorophores carboxyfluorescein, 6-carboxy-4',5'-dichloro-2',7'-dimethoxyfluorescein (6-JOE), and tetramethylrhodamine (TMR). Primers were designed with the Primer3 software around gene exon boundaries with a PCR product range of 100 to 400 bp. To map the multiplex, we collected electropherograms at 2-cycle intervals (cycle numbers 12, 14, 16, 18, and 20) on a MJ Research 225 Tetrad thermal cycler. The inventors recorded all on-scale peaks from a custom detector. All on-scale data were reduced together by first normalizing them against the spectral-response matrix and known sensitivity ratios, and then against the doped ladder and the ACTB gene. The same procedure was applied to neutrophils cultured with *Candida*. Fold induction was calculated as the ratio of expression from neutrophils cultured with *Candida* over a neutrophil alone control. Quantitative RT-PCR was done using TaqMan Gene Expression Assays (Applied Biosystems) and 7500 Real Time PCR system (Applied Biosystems), and was used as a direct comparison to demonstrate a good overlay of data between the two methods, but with an absolute internal calibration for Reaction Mapping and nearly a factor of 100× reduction of reagent cost.

Example 6

Configuring the Line-scan image module to connect to a HSC analysis module, such as a HSC multiplex QPCR module or Sequencer module. The inventors have previously demonstrated development of a fully automated 768-Lane BioMEMS DNA sequencer for long-read (i.e., Sanger) sequencing. This 768-Lane BioMEMS DNA sequencer exceeds the long-range read length by nearly 40% (it achieves 1100 bp PHRED 20) and extends the throughput of the ABI-3730-generation sequencers by about 8×, thus allowing to >5 Mbp/day of DNA to be sequenced. This 768-Lane BioMES DNA sequencer was configured to allow DNA from a DNA sequencing chips, where ~10 picogram amounts of DNA was reproducibly injected into DNA sequencing chips using a novel solid support transfer method that circumvents the volume limitations of pipettors. The inventors used polymeric beads as a solid support to capture DNA extension products from Sanger sequencing reactions by a protocol similar to the Solid Phase Reversible Immobilization technique (SPRI) (Ueberfeld J, et al., *Anal. Chem.* 78, 3632-3627, 2006). The beads were captured with a magnetic needle, thereby preconcentrating the DNA. The protocol then uses the same magnetic needle as an electrode for the electrokinetic injection of a microelectrophoretic sequencing chip (Ueberfeld J, et al., *Anal. Chem.* 78, 3632-3627, 2006). Other methods in the developing the 768-Lane BioMEMS DNA sequencer included, but are not limited to: fabricate large (25 cm×50 cm) glass microdevices with zero bonding defects (30 kV voltage, 300 PSI internal pressure) (Aborn J H, et al., *Lab on a Chip* 6:669-674, 2005; Koutny L, et al., *Anal Chem* 72(14):3388-3391 (2000); Schmalzing D, et al., *Electrophoresis* 20(15-16):3066-3077 (1999); Schmalzing D, et al., *Analytical Chem* 70(11):2303-2310 (1998)); (2) Develop all methods for integrating complex electrodes, sample wells, and high-pressure seals onto glass chips under corrosive, saline, highly basic, and electrolytically active conditions (Aborn J H, et al., *Lab on a Chip* 6:669-674, 2005; Koutny L, et al., *Anal Chem* 72(14):3388-3391 (2000); Schmalzing D, et al., *Electrophoresis* 20(15-16):3066-3077 (1999); Schmalzing D, et al., *Analytical Chem* 70(11):2303-2310 (1998); Mitnik L, et al., *Electrophoresis* 23(5):719-726 (2002); D. Ehrlich, A. et al., *Proc. Micro Total Analysis Systems* 2001 (microTAS 2001), Monterey Calif. 2001); (3) Synthesize polymer matrix (LPA) materials, buffers, wall coatings and protocols specific to long-channel chips (Vazquez M, et al., *Analytical Chem* 74(9):1952-1961 (2002); Vazquez M, et al., *J Chromatogr B* 779(2):163-171 (2002); Vazquez M, et al., *Anal Biochem* 73(13): 3035-3044 (2001)); (4) Develop a four-color detector capable of sensing (two) 384-lane chip devices with suitable sampling rate for long-read sequencing under fast-run conditions (10 pM fluorescein LOD) (El-Difrawy S A, et al., *Rev Sci Instrum* 76(7):074301 (2005)); (5) Develop custom low-noise electronics for the detector subsystems suitable for streaming data from 384 channels simultaneously under high-speed collection conditions; (6) Provide simple and practical handling of 384-well plates to permit automatic electrophoretic regeneration, sample and matrix loading, and continuous unattended operation out of 384-well plates (Aborn J H, et al., *Lab on a Chip* 6:669-674, 2005).

Example 7

Exemplary Operating Methods

Differences between operating methods and sample preparation for PMC applications compared to flow cytometry and microscopy applications are summarized in the paragraphs below.

Also provided herein are specific protocols used to prepare the samples used in the demonstrations described in Example 8 below.

Microdevice Maintenance All flow cytometers require certain routine operating procedures and maintenance. Similarly, PMC also requires routing operating procedures and maintenance. A 1%-concentration of bovine serum albumin in PBS buffer is periodically pumped through the microdevice to reduce protein adhesion (not more than once a week even with heavy use). As with single-channel cytometers, cell suspensions are treated with established cytometry prefiltration methods (Shapiro, Practical Flow Cytometry Wiley-Liss 4th Ed. (2003)). An iodixanol (OptiPrep®, Sigma Aldrich) gradient-medium buoyancy-agent is typically added to the samples to assist buoyancy of the suspended cells. After about 100 hours of use, the microdevices are usually cleaned with chlorine bleach, however there are no extraordinary difficulties with channel fouling or clogging. With careful handling, devices appear to be reusable for an indefinite number of cycles.

Sample loading onto the microdevice is with the automated pipettor out of 96-well or 384-well plates. To counteract settling, the pipettor is also used to periodically mix the sample suspensions by returning at an interval of ~10 minutes to each well, aspirating, then re-loading a portion of each well volume on the microfluidic device.

Sample Preparation

1. Samples for the Primary-Cell (Lymphoma Model) Dilution Studies

For the sensitivity trials described in Example 8, EBm-BRD2-/GFP large B-cell lymphoma cells were obtained from the spleens of female 20-week-old FVB mice (Greenwald et al., *Blood* 103(4):1475-84 (2004)). Unstained splenocytes (negatives) were obtained from female 16-week-old FVB mice. Fresh cells were frozen in freezing media (50% complete-10 RPMI-based medium, 40% FBS, 10% DMSO), then thawed in small batches as needed, diluted to calibrated ratios in PBS buffer and scanned on the PMC.

2. Cell Line for CPTHR Screen

For the large-scale screen described in Example 8, clonal osteocytic cells, expressing a high level of the carboxy-terminal region of parathyroid hormone receptor (CPTHR), were derived from fetuses in which the majority of exons encoding PTH1R had been ablated by gene targeting. These clonal osteocytic (OC) cell lines expressed 1,900,000 to 3,400,000 CPTHR binding sites per cell, a level 6- to 10-fold higher than observed on osteoblastic cells obtained from the same fetal calvarial bones and at least 5-fold higher than in ROS 17/2.8 cells. Biotinylated [Tyr 34 [ human PTH (24-84) was synthesized at the Massachusetts General Hospital Peptide and Oligonucleotide Core Laboratory (Boston, Mass.).

3. The cDNA Library for CPTHR Screen

The cDNA library described in Example 8 was constructed using both random and oligo dT primers to synthesize the first strand DNA. This approach enriches the library with the 5' portions of large cDNAs compared to cDNA libraries prepared using oligo dT primers only. Inserts were cloned in Lambda Zap pCMV-script expression vector (Stratagene). Since insert size represented in the library is crucial for the successful expression cloning, the insert size was examined in single colonies from different pools of the library. For this purpose, a PCR analysis approach was used which utilized T3 and T7 primers and cDNA preps from the single colonies. An average size of 2 kb was obtained. The library was divided into 100 pools of 10,000 PFUs/each and single pools were transiently transfected into COS-7 cells using Fugene 6 (Roche) according to the manufacture's protocol.

The cDNA library, average insert size 2 kb, was divided into 100 pools of 10,000 PFUs/each and single pools were transiently transfected into COS-7. It was calculated that a 200-µL sample (1,000 cells/µL) would produce 20-40 positive events in a positive pool. To reduce the false-positive count a simplified labeling protocol was used and the results were evaluated using the image-processing algorithm described herein. Osteocyte cells without fluorescently labeled ligand were used as a negative control.

Example 8

Exemplary Results Using the Methods and Devices Described Herein

1. Sensitivity Trials on Primary B-Cell Lymphoma Cells

Two of the strengths of the PMC described herein are (1) rare cell measurements and, (2) measurements on primary cells or on cultures where available sample is limited. Below are shown results for a simple dilution study using murine B-cell lymphoma cells. The study was undertaken to prepare for larger studies that use, in one case, human clinical samples and, in a second, murine blood samples for active monitoring of cancer treatment and regression in mouse models. Blood samples from an existing transgenic mouse model that constitutively expresses a double bromodomain-containing 2 (Brd2) GFP fusion were used (Greenwald, supra).

Figure 15B:
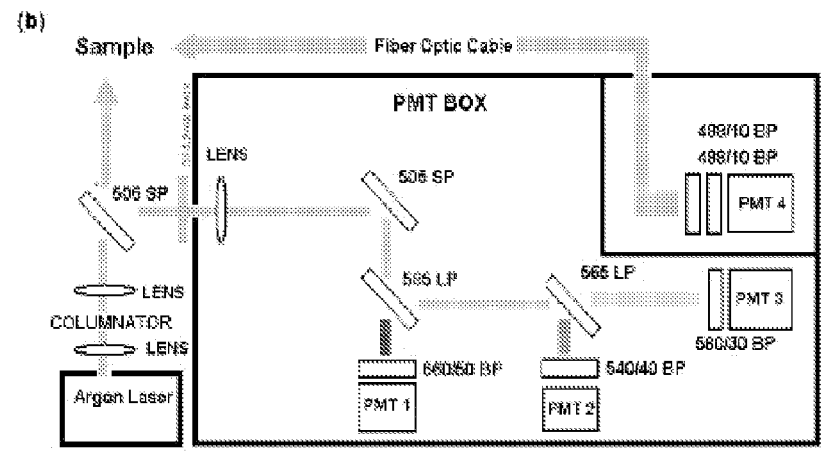
Figure 16:
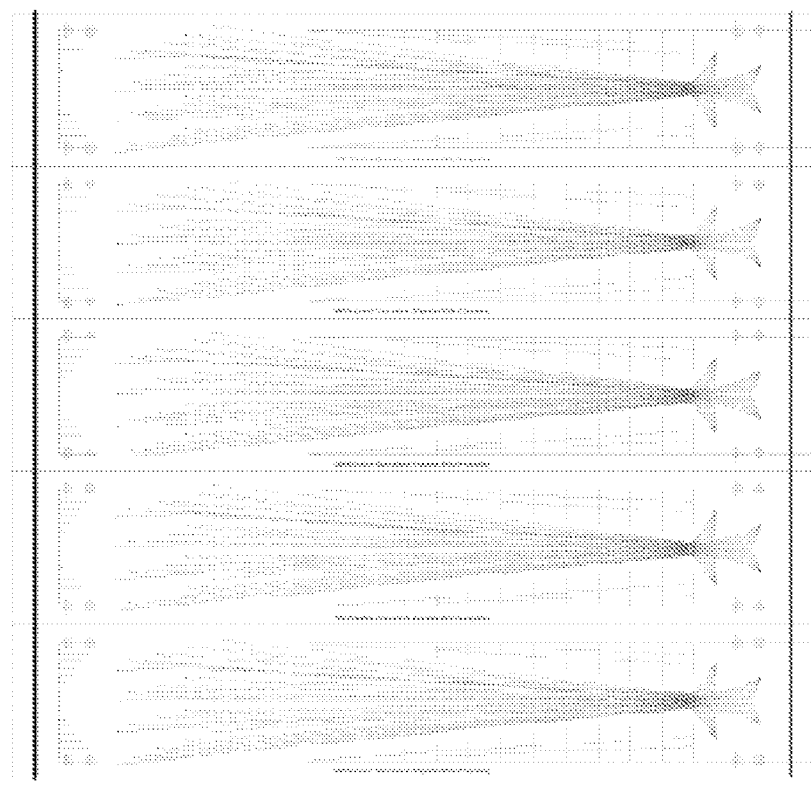
FIG. 16 depicts a plate of 32-channel PMC microdevices at the lithography stage of fabrication. Five devices can be fabricated simultaneously on a 250×250 mm alumina silicate glass plate. There are economies of scale from batch fabrication, particularly yielding improvements at the bonding stage. As a last step individual devices are separated by diamond sawing.
Figure 17:
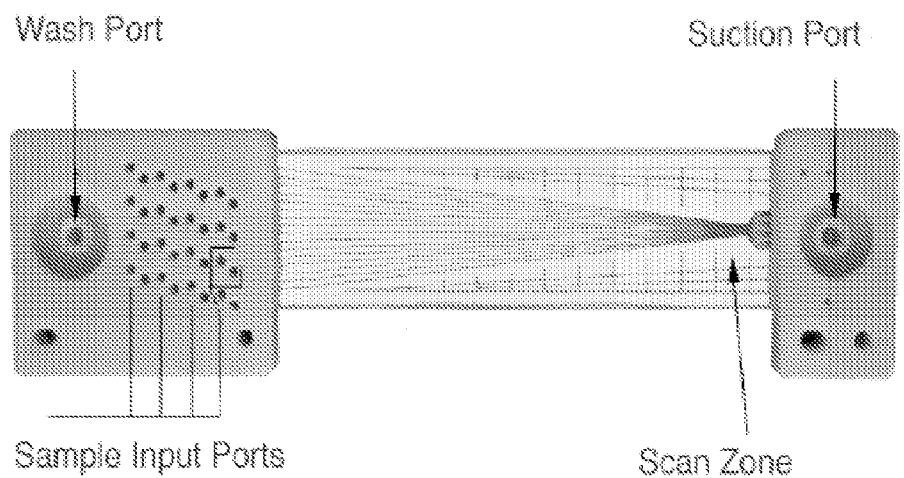
FIG. 17 shows an exemplary finished PMC microdevice similar to those shown in FIG. 15 but after attachment of G-10 fiberglass pumping block and fluid reservoirs. The suction port and wash port are threaded to receive standard 10-32 HPLC fittings. The 32 open sample ports are 2-mm diameter and 10 mm deep, on 9 mm centers (other designs can use 4.5 mm centers) and are compatible with a standard multi-tip pipettor.
Figure 18:
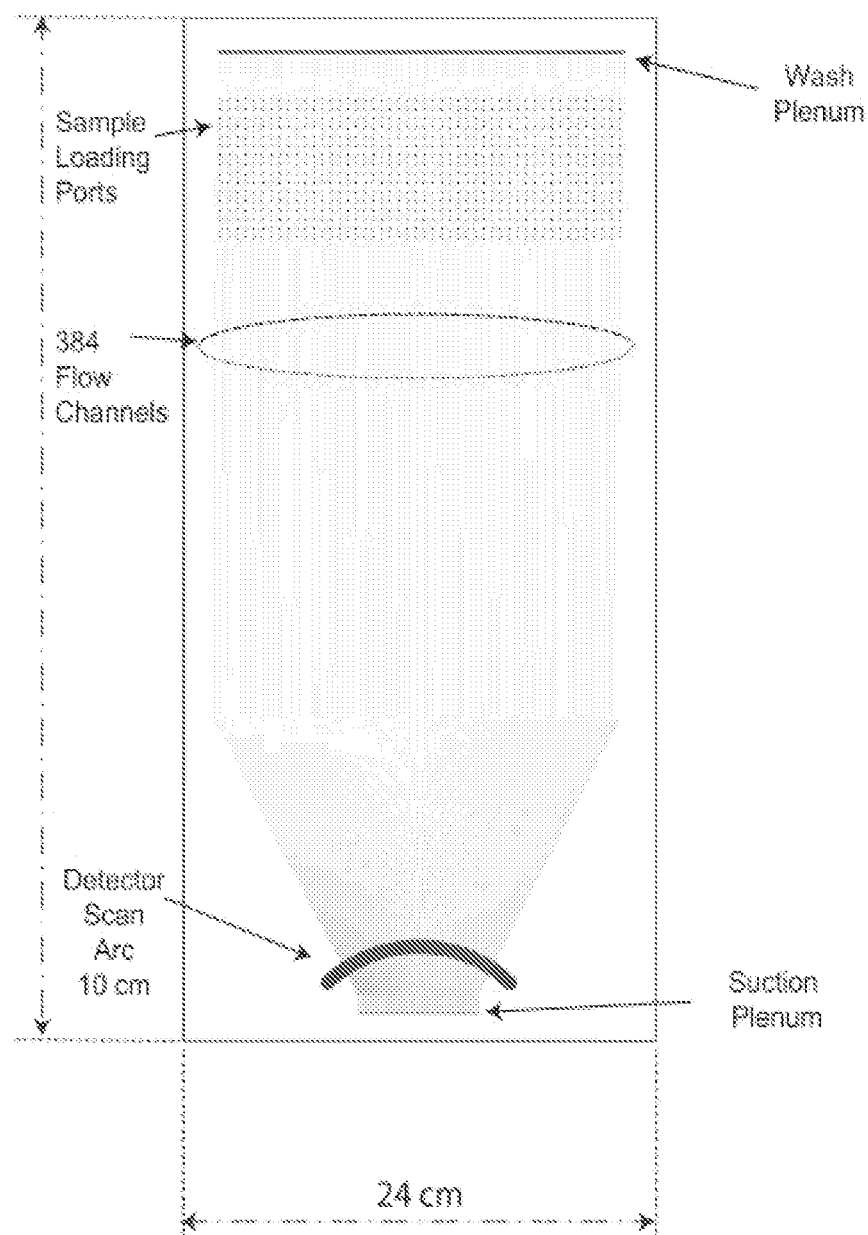
FIG. 18 shows an exemplary 384-channel PMC microdevice plate at mask stage, finished device shown in FIG. 1G. The flow channels fan out on the "loading" (top) end to allow room for the sample-well array that must match the 4.5 mm spacing of the robotic pipettor. At the "scan" end the flow channels converge to a maximum density allowed by the boding process (e.g., 5 channels per mm). The channel cross-section is hemispherical with a 60 µm radius. This channel structure is etched into the glass plate (flat-panel display glass), the access holes are laser drilled, conical shape terminating with a 80 µm diameter at the etched channel, then the plate is sealed by high-temperature fusion bonding.

Samples were prepared by quantitative dilution from cell stocks, then presented to the PMC at a flow rate of ~200 μm/s using the detection arrangement of FIG. 15B. Frozen extracts were used, which presented a more difficult case in terms of signal-to-noise (weaker GFP marker) relative to fresh clinical samples.

2. Dilution Study on Clonal Osteocytes

A second dilution-curve study is shown in FIG. 2 in preparation for a large-scale screen of clonal osteocytic cells. Positive dsRed-expressing cells were serially diluted in a background of GFP-expressing cells. FIG. 2 plots all microfluidic channels for a 384-lane microdevice, but uses eight channels redundantly to collect data for each dilution. This procedure makes use of one of the inherent attributes of the PMC, namely high channel count, to average out flow non-uniformities. The results are much as for the primary cell study above, but with different scan settings. The high concentration saturation artifact of FIG. 25 is not seen up to concentrations well over 50% positives.

3. GENOME-Wide cDNA Screen

The longer integration times of a PMC permit an increase in rare-cell selectivity and thereby allow increased pool sizes for early-stages of large screens. This has major implications for a genome-wide screen where the target must be found in an initial pool of many negatives and where the number of positive cells may number in the single digits per microliter. An on-going genome-wide cDNA screen for the carboxy-terminal parathyroid hormone receptor (CPTHR) was chosen as a test (McKenna et al., 2009). The classical way to approach a screen of this kind is to, (a) separate the several million potential target sequences into a manageable number of initial pools (usually about 10-100 pools), (b) to identify the pool containing the positive sequence then to (c) subdivide this pool. This process is repeated until the positive pool is enriched to the level of a single candidate. The most demanding part of the screen occurs in the initial stage-since it requires finding as few as several-dozen positives (antibody-stained clonal oesteocytes) in a background of a million negatives.

Clonal osteocytes were incubated with 0.5 mM EGTA for 20 minutes at 4° C. Cells were then centrifuged for 3 minutes at 3000 rpm at room temperature and re-suspended in binding buffer. Cell suspensions were incubated with $10^6$ M biotinylated hPTH (24-84) and streptavidin Texas red for one hour at 4° C. Cells were then washed by centrifugation for 3 minutes at 3000 rpm at 4° C., then were re-suspended in binding buffer.

Cells in a 200-μl buffer volume were loaded into multiple sample wells and pulled through the detection zone of the PMC at a flow rate of 10-20 uL/Hr per channel. This corresponds to a flow velocity of several hundred μm/s. The laser spot (nominal diameter ~30 μm) was adjusted to traverse the biological cell at a much faster scan rate of 10-40 mm/s (0.8-3 ms nominal dwell). Each sample was sampled in 4 to 10 duplicate channels in our experiments. To partially automate data reduction, we developed a post scan data process using Matlab. First, the raw data signal of the red PMT (4) is subtracted from the green PMT (2) (FIG. 1B) to compensate for auto-fluorescence. The channel locations are then overlaid to segment the data into individual-channel time sequences—about 15 pixels wide by the total number of scans (~50,000 pixels) long. Each channel segment is searched for scans that contain signal above a noise threshold. These scans are then automatically "cut-and-pasted" to a new image that represents the objects in one channel (accumulated for the run), and the number of events are determined by a software counting algorithm.

Final bright cell counts were entered into a spreadsheet and compared across samples in order to determine run-group statistics median, average and standard deviation. These values were used to determine the probability that a given pool was negative. Those pools that were above the median plus two standard deviation were retested, and if still contained outliers, were designated for further expansion.

Figure 27:
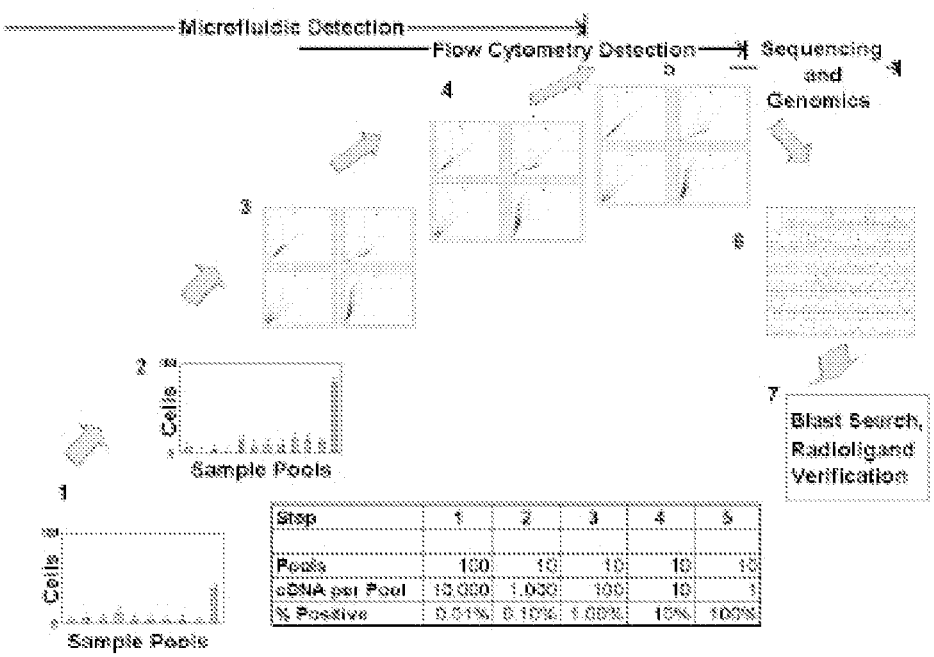
FIG. 27 is a schematic representation of a cDNA expression cloning study that identified a new target for the CPTHR receptor. The most difficult first two stages were completed on the PMC using the rare-cell detection advantages of the variable integration detector.

The workflow of the screen is shown in FIG. 27. The initial stage included nine sample pools and one control, all of which were run in redundant microfluidic channels. All samples showed a few positive cells with a median count of 4 and a standard deviation of 12.58. The boundary for outliers was calculated using the median plus two sigma and determined to be 28. One pool was an outlier with 39 positives, and when tested again produced 35 positives. The outlier was subdivided into twenty subpools and each was tested twice. A count of positives produced a median of 5.5, a sample deviation of 12.47 and an outlier boundary of 47. One sub-pool showed 95, then on recount 98, positive cells. This process was repeated for two more subdivisions until a sample was produced that was overwhelmingly positive (>10,000 on the PMC). Levels 3-5, which had much higher abundances of positives, were conducted in parallel on the PMC and on a conventional single-channel cytometer (FACS-Caliber™, BD Biosciences). Finally a candidate cDNA was isolated, which was sequenced by capillary electrophoresis and found to include seven-transmembrane domain belonging to a family of G-protein coupled receptors (GPCRs). The sequence was run against the BLAST database and found to be a novel candidate. The end result is that the PMC was able to rapidly perform a full genome-wide cDNA-screening assay with statistically significant results on positive counts of only several dozen cells in background of several million negatives and with sample pools of 200 μl.

Example 9

Advantages and Applications of PMC Devices

Four key aspects of the PMC architecture are (i) parallelism from the microfluidics, (ii) high-sensitivity from an optical scanner with variable integration time, (iii) Parallel flow imaging with a high-speed analog detector (rather than CCD), (iv) a small-sample capability from the microfluidics.

The 384-channel parallelism, most importantly improves sample-throughput, but also sidesteps the time biasing between samples due to sample changeover in a single-channel. The elimination of time biasing addresses issues with unstable samples or degrading markers and, importantly, allows rigorously time synchronized comparative assays, e.g., for biological process with fast kinetics. The scanner permits practical adjustment of integration time, including lengthened signal averaging, which greatly improves performance in rare-cell analyses. The microfluidic flow allows efficient handling of very small and rare cell samples, e.g. a few microliters of primary cells. Single-channel cytometers continue to be improved in some of these features (e.g., Goddard et al. 2007, Haynes et al., 2009), however none combines these features. An increased detection sensitivity relative to conventional flow cytometers, as seen in our dilution studies, is reasonable given simple signal-to-noise (S/N) arguments. The PMC and single-channel cytometers utilize nearly the same spectral separation and PMT-based photodetection, both operate in the high signal (rather than photon-counting) regime, both have a dominant noise contribution from the shot noise, and both systems can be operated near photobleaching. This implies a comparable number of signal photons for the two detectors. In the experiments above the inventors have varied the integration time between 0.8 and 60 ms, up to 3-4 orders of magnitude longer than is typically used in a single-channel cytometer. This permits a 3-4 order-of-magnitude smaller amplification bandwidth and, for a Poisson distribution of noise, an advantage of 1.5 to 2 orders of magnitude in the S/N for our detector. Moreover the integration time of the PMC is an elective setting in the system; it is set by the scanner velocity and is independent of minimum flow requirements. On the high-count-rate end both PMC and single-channel cytometers (FACS) are ultimately limited by essentially the same digitizing electronics; therefore the PMC, when it is run at high flow velocity, can achieve approximately the same total count rates as a high-end FACS. In some initial trials, the PMC was adjusted for rare cell capability and high sample-number throughput. This is the optimization for early stages of a genome-wide screen. The inventors confirm the improved performance in this domain of optimization.

For a binary assay, closer to a classical flow-cytometer assay, i.e., abundance of "positives" ~0.1% or higher, the PMC can be operated at an integration time closer to that used in FACS. A realistic sample throughput for a binary assay on the PMC with this tuning is 384 unique samples in six minutes (384-ea. 1 µL samples, 103 cells/µL). This might compare with a maximum of approximately ten unique samples in six minutes for a typical commercial single-channel FACS. However the 384-well-plate automation that permits the PMC to be integrated with existing high-throughput cell culture is important in order to realize these advantages.

In the imaging application, the PMC has demonstrated an unexpected proficiency in separating samples with highly economical 1-D images. Even with a 3.5-µm resolution on a relatively small (5-6 µm) yeast cell, condensation of a GFP marker can be seen, and on mammalian cells, the classical nuclear translocation assay has also been simulated. 1-D imaging on the PMC can be used as a means to add "high-content" to FACS.

The sample throughput of the PMC already exceeds FACS, and it is likely that in the future the PMC will also exceed FACS in absolute (single-sample) count rate. The inventors anticipate an improvement of ten or more over the current state. This will push flow cytometry into the domain near two 384-plates per minute for a binary assay, which is useful for drug discovery.

A PMC device having good independent logic controllers on each channel and with isolated-well fraction collection will permit cell-resolved studies of kinetics in a massively c parallel way, which to date has not been possible to do (especially statistically significant studies of many aspects of biological kinetics with high time response).

It is contemplated herein that the PMC system is adapted to perform high content imaging on a high throughput system. The system described herein offers a significant advantage over automated microscopy—by moving cells in multiple lanes over our unique laser imager the need to focus is eliminated, thus saving the significant mechanical overhead penalty incurred by automated microscopes. Microtiter plate reading automated microscopy systems work by robotically moving the plate well over the microscope (or moving the microscope to the well), "Z" focusing on the bottom of the well, and for each color channel serially illuminating the large field and then digitally capturing an image of the cells. This process is typically done several times for each well (sample) and then repeated for each well in the plate (usually 96 or 384). For a PMC system, all samples of the microtiter plate can be loaded into the chip and cells drawn over the imaging device at the same time, eliminating the overhead of moving from well to well. Such a system has two chip reading areas, so one chip is loaded with sample while the other is recording. The small height of the channels added by hydrodynamic focusing, eliminates the need for "Z" focusing. The smaller illumination field (laser spot) allows for a much higher concentration of laser power, reducing illumination times, and the PMT's independent gain control allow for parallel color channel detection.

In addition, systems as described herein can permit the use of a range of spot sizes upper bounded to more or less the cell size. An advantage would be that a larger spot size would also increase system throughput. A fundamental way to benchmark the throughput potential of a high content screening platform is information per pixel and integration time per pixel. Most imaging systems, are rate limited by data acquisition hardware. For a PMC system (with upgraded A/D) the PMT data acquisition hardware is rate limited to 3µ seconds per pixel. But if one needed to scan only 10 pixels per object and spend 1% of the time actually scanning a cell, such a system can scan 384 samples in 4 minutes (0.000003×0.01=0.003 or 333 objects per second or 1 sample of 200 objects every 0.6 seconds for 384 samples in 230 seconds). The key factor in this equation is the efficiency rate, which is targeted at 1%. Three types of inefficiencies can exist: the time the scanner spends from the end of one scan to beginning the next scan, the percentage of time the scanner is scanning between the lanes and not the lanes, the density of cells in the solution and the volume of sample imaged per pixel. With an expandable spot size (and potentially a variable digital linear resolution size, i.e. microns per pixel) computer simulation and experimentation can be used to determine an optimum setting that maximizes throughput without sacrificing data reliability.

The invention claimed is:

1. A line-scan imaging device for rapid image analysis of particles or biological cells in at least one sample of interest, comprising:
   a. a microfluidic device comprising a plurality of microchannels, wherein each microchannel has an inlet and at least one outlet;
   b. a scanning-imaging detector configured to produce one dimensional (1-D) or low complexity two dimensional (2-D) line images of sufficient resolution for running the image through a cell-type algorithm and also configured to record emitted fluorescence from a particle or biological cell within each of the plurality of microchannels of the microfluidic device; and
   c. an output device configured to receive data input from the scanning-imaging detector, wherein the data input from the 1-D or 2-D line images run through the cell-type algorithm produces 1-D or sparse 2-D images of sufficient resolution to identify cell features, and wherein the output device comprises a storage device and/or a data analysis system that permits cell phenotype determination from the emitted fluorescence detected in step (b).

2. The line-scan imaging device of claim 1, wherein the scanning detector is selected from the group consisting of: a 1-D image detector, a sparse 2-D image detector, a laser-induced florescence (LIF) detector, an avalanche photodiode, or a plurality of photomultipliers (PMTS) and/or photodiode detectors.

3. The line-scan imaging device of claim 1, wherein each microchannel of the plurality of microchannels is at least 30 µm wide in diameter.

4. The line-scan imaging device of claim 1, wherein the scanning-imaging detector records emitted fluorescence at 6 µm intervals or less across the diameter of each microchannel of the plurality of microchannels.

5. The line-scan imaging device of claim 1, wherein the scanning-imaging detector has (a) a detection diameter of between 1-5 µm parallel to the microchannel, (b) a detection diameter of less than one microchannel diameter parallel to the microchannel, or (c) a detection diameter of less than 6 µm in a dimension parallel to the microchannel.

6. The line-scan imaging device of claim 1, wherein the inlet of each of the plurality of microchannels fluidly connects to a plurality of sample wells for sample input into each microchannel.

7. The line-scan imaging device of claim 1, wherein the each microchannel has at least one positive outlet and at least one negative outlet to permit sorting of cells between positive and negative states.

8. The line-scan imaging device of claim 6, wherein the sample well receives samples from the output of a plurality of microfluidic channels from a parallel microfluidic cytometer.

9. The line-scan imaging device of claim 1, wherein each microchannel of the plurality of microchannels on the microfluidic device is configured for vertical hydrodynamic focusing.

10. The line-scan image device of claim 1, wherein the reference point indicating a cell phenotype is a reference line-scan image of cell phenotype.

11. The line-scan image device of claim 10, wherein the reference point indicating a cell phenotype is a value from an algorithm indicating a cell phenotype.

12. The line-scan imaging device of claim 1, wherein the device comprises at least 16 microchannels.

13. The line-scan imaging device of claim 1, wherein the scanning-imaging detector determines information about the intracellular location of the emitted fluorescence within the biological cell.

14. A line-scan imaging device for rapid image analysis of biological cells or particles in at least one sample of interest, comprising:
   a. a microfluidic device comprising at least one microchannel, wherein the microchannel has an inlet and at least one outlet;
   b. a scanning-imaging detector configured to produce one dimensional (1-D) or low complexity two dimensional (2-D) line images of sufficient resolution for running the image through a cell-type algorithm and also configured to record emitted fluorescence from a biological cell or particle within the microchannel of the microfluidic device, wherein the scanning-imaging detector detects the emitted fluorescence from specific compartments of the biological cell or particle; and
   c. an output device configured to receive data input from the scanning-imaging detector, wherein the data input from the 1-D or 2-D line images run through the cell-type algorithm produces 1-D or sparse 2-D images of sufficient resolution to identify specific compartments of the biological cell or particle, and wherein the output device comprises a storage device and/or a data analysis system that permits analysis of the 1-D or 2-D images of sufficient resolution to identify specific compartments of the biological cell or particle.

15. The line-scan imaging device of claim 14, comprising a plurality of microchannels.

16. The line-scan imaging device of claim 14, wherein the scanning-imaging detector has a detection diameter of less than 6 micrometers in a dimension parallel to the microchannel.

17. The line-scan imaging device of claim 14, comprising a plurality of microchannels, and wherein the detector has a detection diameter of less than 6 micrometers in a dimension parallel to the microchannel.

18. The line-scan imaging device of claim 14, wherein the scanning-imaging detector scans transverse to fluid flow in the microchannel.

19. The line-scan imaging device of claim 14, wherein a microchannel has at least one positive outlet and at least one negative outlet to permit sorting of cells between positive and negative states.

20. The line-scan imaging device of claim 1, wherein the particle is a biological cell.

21. The line-scan imaging device of claim 1, wherein the scanning-imaging detector comprises a astigmatic telescope.

22. The line-scan imaging device of claim 1, wherein the scanning-imaging detector comprises an optical encoder.

23. The line-scan imaging device of claim 1, wherein the scanning-imaging detector comprises dichronic mirrors (DM) and relay lenses (RL) in a cascade with photomultipliers (PMTs).

24. The line-scan imaging device of claim 1, wherein the scanning-imaging detector comprises a photomultiplier (PMT) per color channel.

25. The line-scan imaging device of claim 1 or 24, wherein the scanning-imaging detector comprises at least 4 photomultipliers (PMTs).

26. The line-scan imaging device of claim 1, further comprising at least one excitation laser, wherein the excitation laser is configured for strobe laser illumination.

27. The line-scan imaging device of claim 26, further comprising multiplex excitation lasers, wherein each excitation laser is configured for laser illumination on a time delay with respect to the other excitation lasers in the multiplex excitation laser.

28. The line-scan imaging device of claim 27, wherein each excitation laser is configured on an expandable photomultiplier (PMT) cascade.

* * * * *